(12) United States Patent
Persing et al.

(10) Patent No.: US 10,329,629 B2
(45) Date of Patent: Jun. 25, 2019

(54) METHODS OF DETECTING CHLAMYDIA AND GONORRHEA AND OF SCREENING FOR INFECTION/INFLAMMATION BASED ON GENOMIC COPY NUMBER

(71) Applicant: Cepheid, Sunnyvale, CA (US)

(72) Inventors: David Persing, Sunnyvale, CA (US); William E. Murray, Sunnyvale, CA (US)

(73) Assignee: CEPHEID, Sunnyvale, CA (US)

( * ) Notice: Subject to any disclaimer, the term of this patent is extended or adjusted under 35 U.S.C. 154(b) by 388 days.

(21) Appl. No.: 14/907,541

(22) PCT Filed: Jul. 25, 2014

(86) PCT No.: PCT/US2014/048295
§ 371 (c)(1),
(2) Date: Jan. 25, 2016

(87) PCT Pub. No.: WO2015/013676
PCT Pub. Date: Jan. 29, 2015

(65) Prior Publication Data
US 2016/0257998 A1    Sep. 8, 2016

Related U.S. Application Data

(60) Provisional application No. 61/859,067, filed on Jul. 26, 2013.

(51) Int. Cl.
| | | |
|---|---|---|
| C12Q 1/68 | (2018.01) | |
| C12Q 1/689 | (2018.01) | |
| C12Q 1/6883 | (2018.01) | |
| C12Q 1/6886 | (2018.01) | |
| C12Q 1/6895 | (2018.01) | |

(52) U.S. Cl.
CPC ........... *C12Q 1/689* (2013.01); *C12Q 1/6883* (2013.01); *C12Q 1/6886* (2013.01); *C12Q 1/6895* (2013.01); *C12Q 2600/156* (2013.01); *C12Q 2600/158* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | |
|---|---|---|
| 6,582,908 B2 | 6/2003 | Fodor et al. |
| 2008/0299567 A1 | 12/2008 | Marshall et al. |
| 2015/0376683 A1 | 12/2015 | Weir et al. |

FOREIGN PATENT DOCUMENTS

| | | |
|---|---|---|
| EP | 0 630 971 A2 | 12/1994 |
| EP | 0 915 170 A1 | 5/1999 |
| EP | 0 630 971 B1 | 4/2001 |
| JP | A2008-515423 | 5/2008 |
| WO | WO 2013/177329 | 11/2013 |
| WO | WO 2015/013676 | 1/2015 |

OTHER PUBLICATIONS

PCT International Search Report and Written Opinion dated Sep. 13, 2013 issued in PCT/US2013/042300.
PCT International Preliminary Report on Patentability dated Nov. 25, 2014 issued in PCT/US2013/042300.
PCT International Search Report and Written Opinion dated Nov. 3, 2014 issued in PCT/US2014/048295.
PCT International Preliminary Report on Patentability dated Jan. 26, 2016 issued in PCT/US2014/048295.
EP Extended Search Report dated Dec. 4, 2015 issued in EP13793093. 9-1404.
JP Office Action dated Apr. 24, 2017 issued in JP2015-514165.
Chung, et al.(Sep. 9, 2009) "Neisseria gonorrhoeae NCCP11945, complete genome," *GenBank, Accession:CP001050*, 2 pages.
Hollox, et al. (Jan. 2008) "Psoriasis is associated with increased [beta]-defensin genomic copy number" *Nature Genetics—Brief Communications*, 40(1): 23-25.
Moreira, et al. (2009) "Elevated transrenal DNA (cell-free urine DNA) in patients with urinary tract infection compared to healthy controls," *Clinical biochemistry*, 42(7-8): 729-731.
NCBI, GenBank accession No. CP001050.1 (Sep. 9, 2009) "Complete genome sequence of Neisseria gonorrhoeae NCCP11945" *J. Bacteriol*. 190(17): 6035-6036, 122 pages.
NCBI, GenBank accession No. FM872308.1 (Sep. 10, 2009) "Co-evolution of genomes and plasmids within Chlamydia trachomatis and the emergence in Sweden of a new variant strain" *BMC Genomics* 10, 239, 189 pages.
NEB Catalog (1998/1999), pp. 121 and 284 (2 pages).
Roberts, et al. (Jul. 24, 2008) "Critical evaluation of HPV16 gene copy number quantification by SYBR green PCR" *BMC Biotechnology*, 8(57): 1-14.

(Continued)

*Primary Examiner* — Jehanne S Sitton
(74) *Attorney, Agent, or Firm* — Emily M. Haliday; Weaver Austin Villeneuve & Sampson LLP

(57) ABSTRACT

Compositions and methods for detecting *Chlamydia trachomatis* (CT) and *Neisseria gonorrhoeae* (NG) are provided. The present invention also provides methods and compositions for screening for infection/inflammation based on genomic copy number. Described herein is a method that entails assaying a sample obtained from the urogenital tract of the mammal for an indicator of genomic copy number, wherein a genomic copy number level that is higher than a control genomic copy number level is indicative of the presence of infection or inflammation of the urogenital tract. Also described in a kit of the invention that includes a primer and/or probe for detecting or sequencing an indicator of genomic copy number, wherein the indicator of genomic copy number comprises a nucleic acid sequence that is expected to be present in the genome of the mammal in one or two copies; and a primer and/or probe for detecting or sequencing a nucleic acid sequence that is indicative of a pathogen that infects the urogenital tract or a miRNA correlated with inflammation.

15 Claims, 13 Drawing Sheets

Figure 1A:
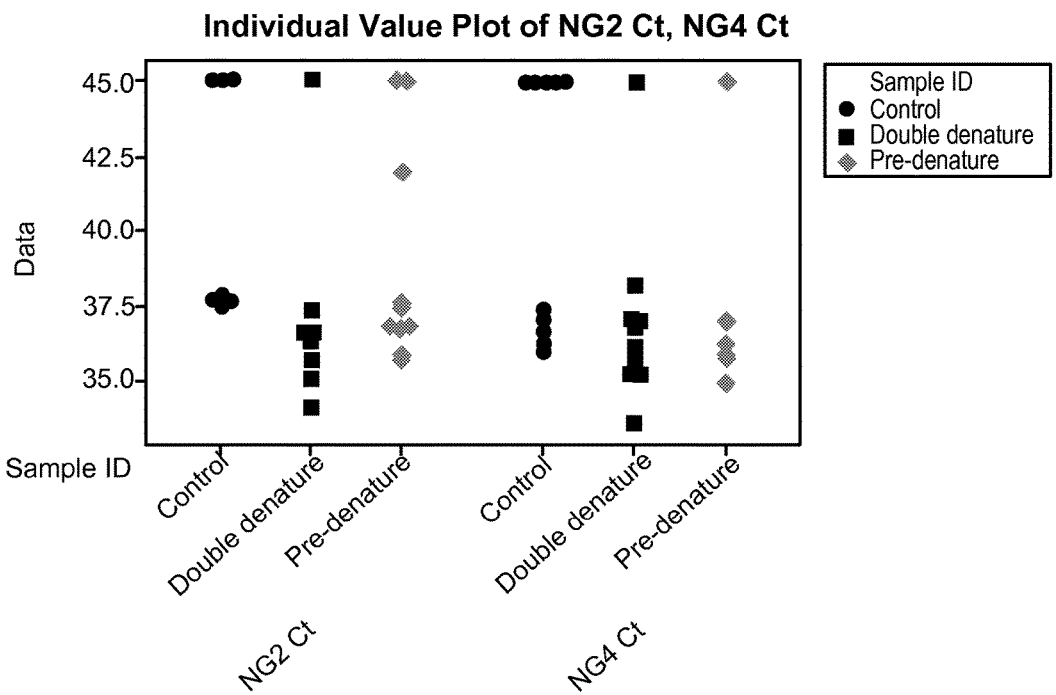

Specification includes a Sequence Listing.

(56) References Cited

OTHER PUBLICATIONS

Seth-Smith, et al. (Sep. 10, 2009) "Chlamydia trachomatis B/Jali20/0T, complete genome," *GenBank, Accession:FM872308*, 2 pages.

Swan, et al. (1999) "Human papillomavirus (HPV) DNA copy number is dependent on grade of cervical disease and HPV type," *J Clin Microbiol.*, 37(4): 1030-34.

Voortman, et al. (Jul. 20, 2010) "Array comparative genomic hybridization-based characterization of genetic alterations in pulmonary neuroendocrine tumors" *PNAS*, 107(29): 13040-13045.

EP Office Action dated Nov. 22, 2018 issued in EP13793093.9.

| | GP Swab | POS | POS | POS | EQ | EQ | EQ | NEG* | NEG | NEG |
|---|---|---|---|---|---|---|---|---|---|---|
| | GP Urine | POS | EQ | NEG | POS | EQ | NEG | POS* | EQ | NEG |
| BD Swab | BD Urine | | | | | | | | | |
| POS | POS | — | — | — | — | NI | NI | — | NI | NI |
| POS | EQ | — | — | — | NI | NI | — | NI | NI | NI |
| POS | NEG | — | — | — | NI | NI | — | NI | NI | NI |
| EQ | POS | — | — | — | NI | NI | — | NI | NI | NI |
| EQ | EQ | NI | NI | NI | NI | EQ | NI | NI | NI | NI |
| EQ | NEG | NI | NI | NI | NI | NI | NI | NI | NI | NI |
| NEG* | POS* | — | — | — | NI | NI | — | NI | NI | NI |
| NEG | EQ | NI | NI | NI | NI | NI | NI | NI | NI | NI |
| NEG | NEG | NI | NI | NI | NI | NI | NI | NI | NI | NI |

*Fig. 2*

| CT | Sensitivity | | | | | |
|---|---|---|---|---|---|---|
| | BD ProbeTec Qx | Gen-Probe APTIMA | Roche Amplicor | Roche cobas CT/NG | Abbott Realtime CT/NG | Xpert CT/NG Assay |
| VS Female | 96.5% | 96.6% | | 93.9% | 93.6% | 99.5% |
| ES Female | 91.3% | 93.1% | 90.9% | | | 96.0% |
| Urine Female | 93.0% | 94.7% | 87.1% | | 94.2% | 98.1% |
| Urine Male | 98.0% | 97.9% | 89.8% | 97.6% | 97.6% | 98.5% |

*Fig. 3A*

| CT | Specificity | | | | | |
|---|---|---|---|---|---|---|
| | BD ProbeTec Qx | Gen-Probe APTIMA | Roche Amplicor | Roche cobas CT/NG | Abbott Realtime CT/NG | Xpert CT/NG Assay |
| VS Female | 99.2% | 96.8% | | 99.7% | 99.4% | 99.1% |
| ES Female | 98.3% | 98.5% | 98.6% | | | 99.6% |
| Urine Female | 99.2% | 98.9% | 98.4% | | 99.4% | 99.8% |
| Urine Male | 98.1% | 98.5% | 93.8% | 99.5% | 99.7% | 99.8% |

*Fig. 3B*

| NG | Sensitivity | | | | | |
|---|---|---|---|---|---|---|
| | BD ProbeTec Qx | Gen-Probe APTIMA | Roche Amplicor | Roche cobas CT/NG | Abbott Realtime CT/NG | Xpert CT/NG Assay |
| VS Female | 100.0% | 96.10% | | 97.0% | 98.1% | 100.0% |
| ES Female | 98.5% | 96.9% | 95.9% | | 88.0% | 100.0% |
| Urine Female | 96.9% | 91.3% | | | 88.2% | 94.4% |
| Urine Male | 100.0% | 98.5% | 96.5% | 100.0% | 99.4% | 98.3% |

*Fig. 3C*

| NG | Specificity | | | | | |
|---|---|---|---|---|---|---|
| | BD ProbeTec Qx | Gen-Probe APTIMA | Roche Amplicor | Roche cobas CT/NG | Abbott Realtime CT/NG | Xpert CT/NG Assay |
| VS Female | 99.1% | 99.2% | | 100.0% | 99.9% | 99.9% |
| ES Female | 99.7% | 99.6% | 98.7% | | 99.8% | 100.0% |
| Urine Female | 99.5% | 99.3% | | | 99.6% | 100.0% |
| Urine Male | 98.9% | 99.6% | 97.3% | 99.7% | 99.6% | 99.9% |

*Fig. 3D*

METHODS OF DETECTING CHLAMYDIA AND GONORRHEA AND OF SCREENING FOR INFECTION/INFLAMMATION BASED ON GENOMIC COPY NUMBER

1. CROSS-REFERENCE TO RELATED APPLICATIONS

This application claims the benefit of U.S. provisional application No. 61/859,067, filed Jul. 26, 2013, which is hereby incorporated by reference in its entirety.

2. STATEMENT AS TO RIGHTS TO INVENTIONS MADE UNDER FEDERALLY SPONSORED RESEARCH AND DEVELOPMENT

Not applicable.

3. FIELD OF THE INVENTION

The present invention relates to generally to the area of molecular diagnostics. Compositions and methods for detecting *Chlamydia trachomatis* (CT) and *Neisseria gonorrhoeae* (NG) are provided. In particular, CT and NG markers and panels of markers useful in the detection of CT and NG are provided. In addition, the invention relates to methods and compositions for screening for infection/inflammation based on genomic copy number.

4. BACKGROUND OF THE INVENTION

*Chlamydia trachomatis* (CT) is one of three species in the *Chlamydia* family of gram-negative bacteria. CT is an obligate intracellular pathogen, which can only reproduce inside its host cell. CT includes at least two biovars, trachoma and lymphogranuloma venereum (LGV). The trachoma biovar includes at least 14 serovars whose infection is primarily in epithelial cells of mucous membranes. LGV includes at least four serovars that can invade lymphatic tissue. There are an estimated 3 million CT infections annually, most of which are asymptomatic. In the United States, the national rate of CT infection in 2006 was about 348 cases per 100,000 people, which was a 5.6% increase from 2005.

*Neisseria gonorrhoeae* (NG) is a gram-negative oxidase-positive diplococcus bacterium. There are an estimated 700,000 NG infections annually. The NG infection rate in the United States also increased by over 5% from 2005 to 2006, to about 121 cases per 100,000 people. Symptoms of NG infection differ according to the site of infection, although a majority of infected women and a significant proportion of infected men are asymptomatic.

If left untreated, both CT and NG infections can lead to pelvic inflammatory disease and infertility in women, and urethritis in men. The Centers for Disease Control (CDC) currently recommends annual CT screening for all sexually active women under 26.

Many current CT/NG tests are complex assays requiring several different apparatuses and are therefore run in batch format. Batch format tests are not run on demand, and results are therefore typically not received for several days, during which time an infection can be spread. In addition, the leading tests detect CT genes located on a plasmid. While those sequences are present in higher copy, they are also more easily lost, as demonstrated by the emergence and rapid spread of a variant CT strain in Sweden that escaped detection because it had a plasmid deletion. See, e.g., Seth-Smith et al., *BMC Genomics*, 10:239 (2009). In addition, because species in the *Neisseria* family are closely related, some current tests have a high rate of false positives for NG.

Genomic copy number analysis usually refers to the process of analyzing data produced by assays for DNA copy number variation at specific genomic loci in a subject's sample. Such analysis helps detect copy number variation at specific loci that may cause, increase risk of, or be correlated with diseases, such as cancer. Copy number variation can be detected with various types of tests such as fluorescent in situ hybridization, comparative genomic hybridization and with high-resolution array-based tests based on array comparative genomic hybridization (aCGH) and SNP array technologies. Array-based methods have been accepted as the most efficient in terms of their resolution and high-throughput nature.

5. SUMMARY OF THE INVENTION

Methods of detecting *Chlamydia trachomatis* (CT) and/or *Neisseria gonorrhoeae* (NG) in a sample from a subject are provided. In some embodiments, the methods comprise detecting the presence of a first gene comprising the sequence of SEQ ID NO: 2, detecting the presence a second gene comprising the sequence of SEQ ID NO: 4, and detecting the presence of a third gene selected from a gene comprising the sequence of SEQ ID NO: 7 and a gene comprising the sequence of SEQ ID NO: 8 in the sample. In some embodiments, the presence of the first gene and the second gene indicates that the sample contains NG. In some embodiments, the presence of the third gene indicates that the sample contains CT. In some embodiments, the third gene comprises the sequence of SEQ ID NO: 7. In some embodiments, the method comprises detecting an endogenous control. In some embodiments, the endogenous control comprises a nucleic acid sequence that comprises a HMBS, GAPDH, beta-actin, and/or beta-globin nucleic acid sequence. In some embodiments, the endogenous control comprises a HMBS nucleic acid sequence. In some embodiments, the method comprises detecting an exogenous control. In some embodiments, the exogenous control comprises a bacterial DNA sequence.

In some embodiments, the detecting method comprises nucleic acid amplification. Suitable non-limiting exemplary amplification methods can include polymerase chain reaction (PCR), reverse-transcriptase PCR, real-time PCR, nested PCR, multiplex PCR, quantitative PCR (Q-PCR), nucleic acid sequence based amplification (NASBA), transcription mediated amplification (TMA), ligase chain reaction (LCR), rolling circle amplification (RCA), and strand displacement amplification (SDA).

In some embodiments the amplification method comprises an initial denaturation at about 90° C. to about 100° C. for about 1 to about 10 minutes, followed by cycling that comprises denaturation at about 90° C. to about 100° C. for about 1 to about 30 seconds, annealing at about 55° C. to about 75° C. for about 1 to about 30 seconds, and extension at about 55° C. to about 75° C. for about 5 to about 60 seconds. In some embodiments, for the first cycle following the initial denaturation, the cycle denaturation step is omitted. The particular time and temperature will depend on the particular nucleic acid sequence being amplified and can readily be determined by a person of ordinary skill in the art.

In some embodiments, detecting the presence of the genes comprises real time PCR. In some embodiments, the method comprises contacting DNA from the sample with a first primer pair for detecting the first gene, a second primer pair for detecting the second gene, and a third primer pair for detecting the third gene. In some embodiments, the first primer pair comprises a primer having the sequence of SEQ ID NO: 32 and a primer having the sequence of SEQ ID NO: 33. In some embodiments, the second primer pair comprises a primer having the sequence of SEQ ID NO: 47 and a primer having the sequence of SEQ ID NO: 48. In some embodiments, the third primer pair comprises a primer having the sequence of SEQ ID NO: 71 and a primer having the sequence of SEQ ID NO: 72. In some embodiments, the method comprises contacting DNA from the sample with a fourth primer pair for detecting an endogenous control. In some embodiments, the fourth primer pair is for detecting HMBS. In some embodiments, the fourth primer pair comprises a primer having the sequence of SEQ ID NO: 113 and a primer having the sequence of SEQ ID NO: 114. In some embodiments, the method comprises contacting DNA from the sample with a fifth primer pair for detecting an exogenous control. In some embodiments, the exogenous control comprises a bacterial DNA sequence.

In some embodiments, the method comprises contacting DNA from the sample with a first probe for detecting an amplicon from the first gene, a second probe for detecting an amplicon from the second gene, and a third probe for detecting an amplicon from the third gene. In some embodiments, the first probe has the sequence of SEQ ID NO: 34. In some embodiments, the second probe has the sequence of SEQ ID NO: 49. In some embodiments, the third probe has the sequence of SEQ ID NO: 73. In some embodiments, each probe comprises a dye. In some embodiments, each dye is detectably different from other said dyes. In some embodiments, each probe comprises a fluorescent dye and a quencher molecule. In some embodiments, the method comprises contacting DNA from the sample with a fourth probe for detecting an amplicon from an endogenous control. In some embodiments, the endogenous control comprises a nucleic acid sequence that comprises a HMBS, GAPDH, beta-actin, and/or beta-globin nucleic acid sequence. In some embodiments, the endogenous control comprises a HMBS nucleic acid sequence. In some embodiments, the fourth probe has the sequence of SEQ ID NO: 115. In some embodiments, the fourth probe comprises a dye that is detectably different from the dyes of the first, second, and third probes. In some embodiments, the fourth probe comprises a fluorescent dye and a quencher molecule. In some embodiments, the method comprises contacting DNA from the sample with a fifth probe for detecting an amplicon from an exogenous control. In some embodiments, the exogenous control comprises a bacterial DNA sequence.

In some embodiments, the first, second, and third genes are detected in a single multiplex reaction. In some embodiments, an endogenous control is detected in the same multiplex reaction with the first, second, and third genes. In some embodiments, an exogenous control is detected in the same multiplex reaction with the first, second, and third genes.

In some embodiments, the sample comprises a urine sample, a urethral swab sample, a vaginal swab sample, an endocervical swab sample, an oropharyngeal swab sample, a rectal swab sample, or an eye swab sample. In some embodiments, the sample comprises a urine sample, a urethral swab sample, a vaginal swab sample, or an endocervical swab sample. In some embodiments, the subject has a history of sexually transmitted infection.

In some embodiments, the detecting comprises real-time PCR, and wherein DNA from the sample is subjected to a first denaturation step before the DNA is contacted with primers. In some embodiments, DNA from the sample is subjected to a second denaturation step after the DNA is contacted with primers.

In some embodiments, a composition comprising a set of primer pairs is provided. In some some embodiments, the set of primer pairs comprises a first primer pair for detecting a first gene comprising the sequence of SEQ ID NO: 2, a second primer pair for detecting a second gene comprising the sequence of SEQ ID NO: 4, and a third primer pair for detecting a third gene selected from a gene comprising the sequence of SEQ ID NO: 7 and a gene comprising the sequence of SEQ ID NO: 8. In some embodiments, the third gene comprises the sequence of SEQ ID NO: 7. In some embodiments, the first primer pair comprises a primer having the sequence of SEQ ID NO: 32 and a primer having the sequence of SEQ ID NO: 33. In some embodiments, the second primer pair comprises a primer having the sequence of SEQ ID NO: 47 and a primer having the sequence of SEQ ID NO: 48. In some embodiments, the third primer pair comprises a primer having the sequence of SEQ ID NO: 71 and a primer having the sequence of SEQ ID NO: 72.

In some embodiments, the composition comprises a set of probes. In some embodiments, the set of probes comprises a first probe for detecting an amplicon from the first gene, a second probe for detecting an amplicon from the second gene, and a third probe for detecting an amplicon from the third gene. In some embodiments, the first probe has the sequence of SEQ ID NO: 34. In some embodiments, the second probe has the sequence of SEQ ID NO: 49. In some embodiments, the third probe has the sequence of SEQ ID NO: 73. In some embodiments, each probe comprises a dye, and wherein each dye is detectably different from other said dyes. In some embodiments, each probe comprises a fluorescent dye and a quencher molecule.

In some embodiments, the composition comprises a fourth probe for detecting an amplicon from the endogenous control. In some embodiments, the endogenous control comprises a nucleic acid sequence that comprises a HMBS, GAPDH, beta-actin, and/or beta-globin nucleic acid sequence. In some embodiments, the endogenous control comprises a HMBS nucleic acid sequence. In some embodiments, the probe has the sequence of SEQ ID NO: 115. In some embodiments, the fourth probe comprises a dye that is detectably different from the dyes of the first, second, and third probes. In some embodiments, the fourth probe comprises a fluorescent dye and a quencher molecule.

In some embodiments, the composition is a lyophilized composition. In some embodiments, the composition is a solution. In some embodiments, the composition further comprises DNA from a sample from a subject being tested for CT and NG. In some embodiments the composition is in bead form.

Another aspect of the invention includes a method of screening a mammal for infection or inflammation of the urogenital tract. The method entails assaying a sample obtained from the urogenital tract of the mammal for an indicator of genomic copy number, wherein a genomic copy number level that is higher than a control genomic copy number level is indicative of the presence of infection or inflammation of the urogenital tract. In some embodiments, the method includes assaying the sample for a plurality of indicators of genomic copy number. In some embodiments, the indicator of genomic copy number includes a nucleic acid sequence that is expected to be present in the genome of the mammal in one or two copies. Illustrative indicators of genomic copy number include nucleic acid sequences such as a hydroxymethylbilane synthase (HMBS), glyceraldehyde 3-phosphate dehydrogenase (GAPDH), beta-actin, and beta-globin nucleic acid sequence.

In some embodiments of the screening method, the assay employed includes nucleic acid amplification, nucleic acid hybridization, and/or nucleic acid sequencing. In some embodiments, the assay includes nucleic acid amplification, e.g., real-time PCR. In some embodiments, the indicator of genomic copy number includes an HBMS sequence, which is amplified using primers including SEQ ID NO:113 and SEQ ID NO:114. In some embodiments, an amplicon amplified by the primers is detected using a probe. Where the indicator of genomic copy number includes a HBMS nucleic acid sequence, an illustrative probe includes SEQ ID NO:115.

In some embodiments of the screening method, the assay includes hybridizing, under stringent conditions, sample nucleic acid with at least one probe. In some embodiments, the probe is immobilized on a substrate.

In some embodiments of the screening method, the assay includes nucleic acid sequencing, e.g., high-throughput DNA sequencing.

In some embodiments, the mammal subjected to the screening method is human. In some embodiments, the mammal subjected to the screening method is either male or female. In some embodiments, the mammal can have at least one clinical symptom of urogenital infection or inflammation. In some embodiments, the mammal can be one that has had a prior sexually transmitted disease.

In some embodiments, the mammal is a human male who has been tested for prostate-specific antigen (PSA) as an indicator of prostate cancer and has been found to have a sufficiently elevated PSA level to be a candidate for a biopsy. In some embodiments involving elevated PSA levels where the genomic copy number level in the sample is higher than a control genomic copy number level, the method additionally entails identifying the human male as one in which the elevated PSA may be due to infection, rather than cancer. In variations of some embodiments, the method additionally entails deferring biopsy until after infection is ruled out or resolved. In some embodiments, the method additionally entails performing a second assay of a sample obtained from the urogenital tract of the human male for an indicator of genomic copy number or causing the additional assay to be performed. In some embodiments, the method additionally entails treating the human male for infection. In some embodiments, if, in the initial assay, the genomic copy number level in the sample was higher than a control genomic copy number level, and in the second assay, the genomic copy number level in the sample is less than or equal to a control genomic copy number level, the method additionally includes performing a second PSA test.

In some embodiments of the screening method, the sample includes a sample selected from the group consisting of a urine sample, a urethral swab sample, a vaginal swab sample, and an endocervical swab sample.

In some embodiments of the screening method, the method additionally entails assaying a sample from the mammal for the presence of a protein, peptide, or nucleic acid sequence that is indicative of a pathogen, e.g., *Chlamydia trachomatis* (CT) *Neisseria gonorrhoeae* (NG), *Mycoplasma genitalium* (MG), *Ureaplasma, Trichomonas, Leptotrichia*, and/or *Sneathia*. In some embodiments, the method can additionally entail assaying a sample from the mammal for the presence and/or level of a microRNA (miRNA) that is correlated with inflammation. In some embodiments, the same sample can be assayed simultaneously for a nucleic acid sequence that is expected to be present in the genome of the mammal in one or two copies and/or the nucleic acid sequence that is indicative of a pathogen or the miRNA, respectively. Such an assay can be carried out, e.g., using multiplex real-time PCR.

In some embodiments of the screening method, if the genomic copy number level in the sample is higher than a control genomic copy number level, the method additionally includes identifying the mammal as one who may have infection or inflammation of the urogenital tract. In embodiments in which the sample has been assayed for a pathogen and found to be positive, if the genomic copy number level in the sample is higher than a control genomic copy number level, the mammal is, in some embodiments, identified as one who is infected with the pathogen. However, if the sample is positive for the pathogen, but the genomic copy number level in the sample is not higher than a control genomic copy number level, the mammal is identified as one who may be an asymptomatic carrier of the pathogen. In some embodiments, such a mammal is retested for the pathogen. Alternatively, if the sample is negative for the pathogen, and if the genomic copy number level in the sample is higher than a control genomic copy number level, the mammal is, in some embodiments, identified as one who may be infected with a different pathogen or may have inflammation of the urogenital tract that is not due to infection.

For example, in embodiments in which the sample has been assayed for *Chlamydia trachomatis* (CT) and/or *Neisseria gonorrhoeae* (NG) and found to be positive, if the genomic copy number level in the sample is higher than a control genomic copy number level, the mammal is, in some embodiments, identified as one who is infected with CT or NG, respectively. However, if the sample is positive for *Chlamydia trachomatis* (CT) and/or *Neisseria gonorrhoeae* (NG), but the genomic copy number level in the sample is not higher than a control genomic copy number level, the mammal is identified as one who may not be infected with CT or NG, respectively. In some embodiments, such a mammal is retested for *Chlamydia trachomatis* (CT) and/or *Neisseria gonorrhoeae* (NG). Alternatively, if the sample is negative for *Chlamydia trachomatis* (CT) and *Neisseria gonorrhoeae* (NG), and if the genomic copy number level in the sample is higher than a control genomic copy number level, the mammal is, in some embodiments, identified as one who may be infected with a different pathogen or may have inflammation of the urogenital tract that is not due to infection.

In some embodiments, the screening method additionally entails recording the assay result, and/or a diagnosis based at least in part on the assay result, in a patient medical record. In some embodiments, the assay result or diagnosis is recorded in a computer-readable medium. The patient medical record may be, in some embodiments, maintained by a laboratory, physician's office, a hospital, a health maintenance organization, an insurance company, or a personal medical record website.

In some embodiments, the method additionally entails performing one or more additional assay(s) or examination(s) or causing one or more additional assay(s) or examination(s) to be performed. Where the genomic copy number level in the sample is higher than a control genomic copy number level, the additional assay can include an assay of the same, or a different, sample from the mammal for a pathogen, such as, e.g., *Chlamydia trachomatis* (CT), *Neis-* seria gonorrhoeae (NG), *Mycoplasma, Ureaplasma, Trichomonas, Leptotrichia,* and/or *Sneathia*. In some embodiments, where the sample is negative for a first pathogen and the genomic copy number level in the sample is higher than a control genomic copy number level, and the additional assay comprises an assay of the same, or a different, sample from the mammal for a second, different pathogen. The second, different pathogen can be e.g. a bacterium, a fungus or a virus. In some embodiments, where the genomic copy number level in the sample is higher than a control genomic copy number level, the additional assay can include an assay of the same, or a different, sample from the mammal for a condition selected from the group consisting of autoimmune urethritis, prostatitis, bladder cancer, prostate cancer, kidney cancer, or an examination of the mammal for said condition. In some embodiments, at least two additional assays are performed to monitor for any change in the genomic copy number level over time. For example, in some embodiments, at least two additional assays are performed to monitor for the appearance of, or any change in, one or more clinical symptom(s) over time.

A further aspect of the invention includes a method of treating a mammal for infection or inflammation of the urogenital tract, the method including: receiving results from the screening method; and initiating and/or altering therapy for infection or inflammation of the urogenital tract or causing therapy to be initiated and/or altered. In some embodiments, the results are employed in making a differential diagnosis with respect to type of infection or inflammation of the urogenital tract.

Another aspect of the invention includes a kit useful for a method of screening a mammal for infection or inflammation of the urogenital tract based on assaying genomic copy number. In some embodiments, the kit includes: a primer and/or probe for detecting or sequencing an indicator of genomic copy number, wherein the indicator of genomic copy number includes a nucleic acid sequence that is expected to be present in the genome of the mammal in one or two copies; and a primer and/or probe for detecting or sequencing a nucleic acid sequence that is indicative of a pathogen that infects the urogenital tract or a miRNA correlated with inflammation. In some embodiments, the kit includes a primer and/or a probe for detecting or sequencing each of a plurality of indicators of genomic copy number. In some embodiments, the indicator of genomic copy number includes a nucleic acid sequence selected from the group consisting of a hydroxymethylbilane synthase (HMBS), glyceraldehyde 3-phosphate dehydrogenase (GAPDH), beta-actin, and beta-globin nucleic acid sequence. In some embodiments, the indicator of genomic copy number includes an HBMS sequence, and the kit includes primers including SEQ ID NO:113 and SEQ ID NO:114. In some embodiments, where the indicator of genomic copy number includes a HBMS nucleic acid sequence, the kit can include a probe including SEQ ID NO:115.

In some embodiments, the kit for performing the screening method includes a plurality of probes immobilized on a substrate.

In some embodiments, the kit includes a primer and/or probe for detecting or sequencing a nucleic acid sequence that is indicative of a pathogen that infects the urogenital tract. In some embodiments, the pathogen is *Chlamydia trachomatis* (CT) and/or *Neisseria gonorrhoeae* (NG). In some embodiments, the kit can include a primer and/or probe for detecting or sequencing a miRNA correlated with inflammation.

In some embodiments, the kit can include a receptacle for a urine sample or a swab for collecting a urethral swab sample, a vaginal swab sample, or an endocervical swab sample.

Some embodiments and details of the inventions are described below.

6. BRIEF DESCRIPTION OF THE DRAWINGS

Figure 1B:
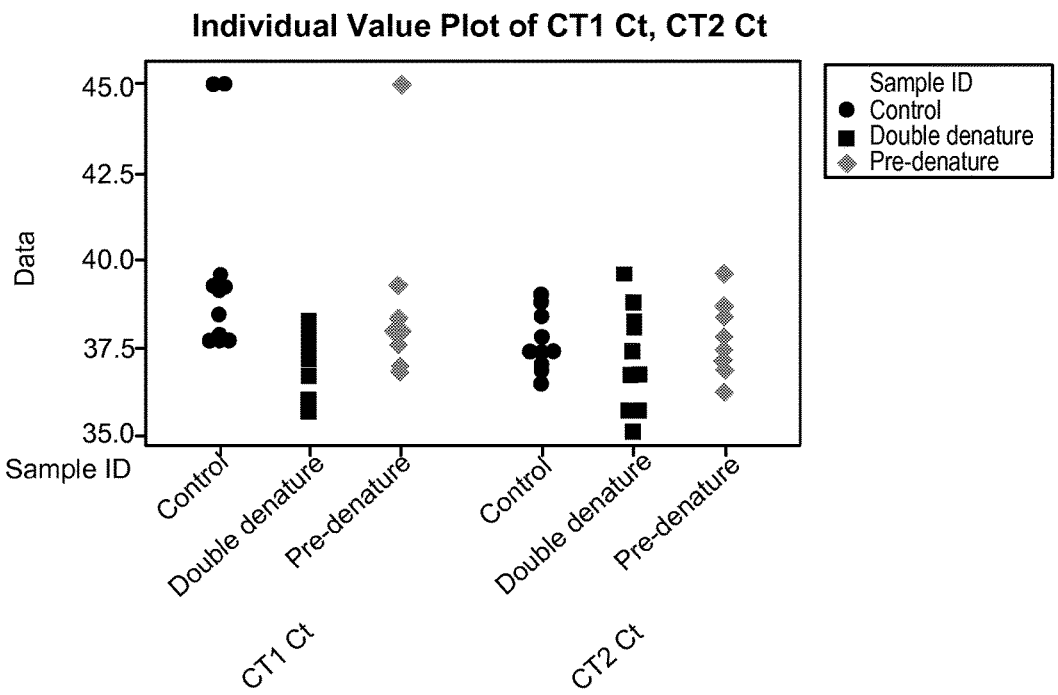
Figure 4A:
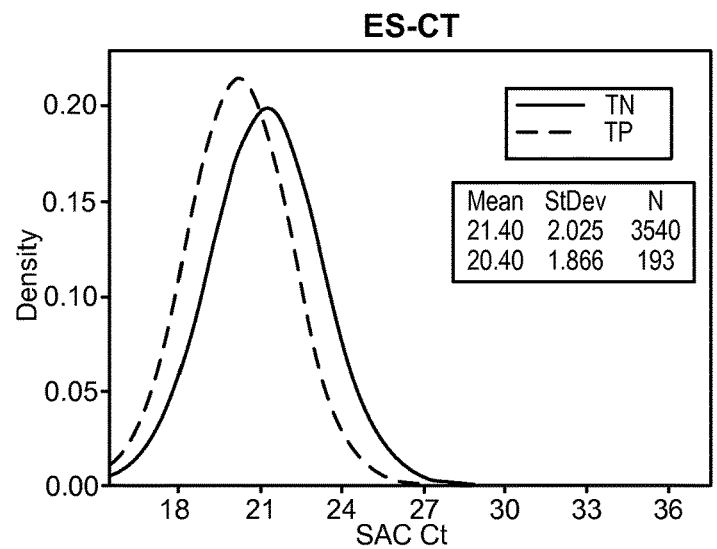
Figure 4B:
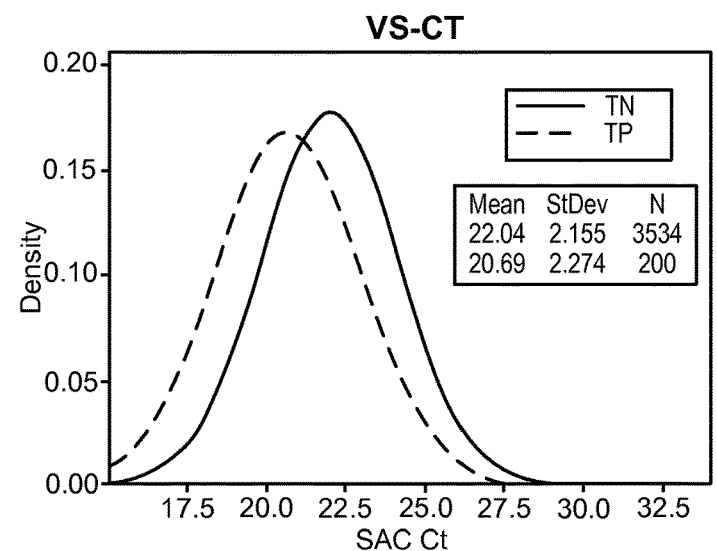
Figure 4C:
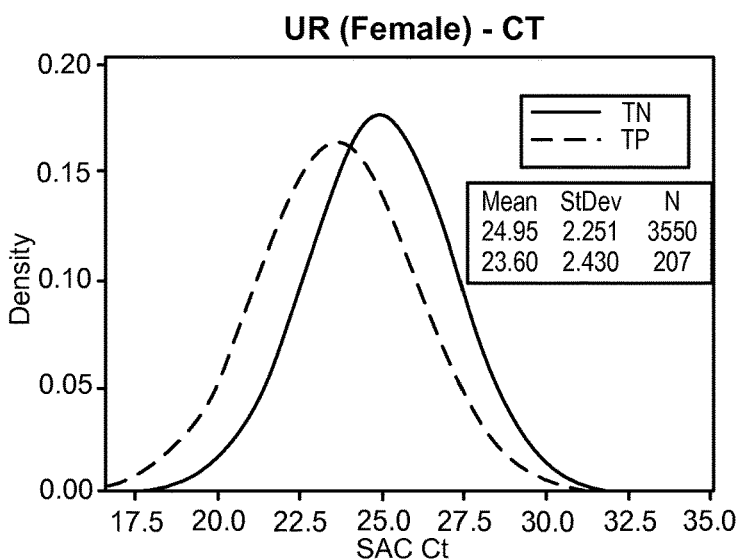
Figure 4D:
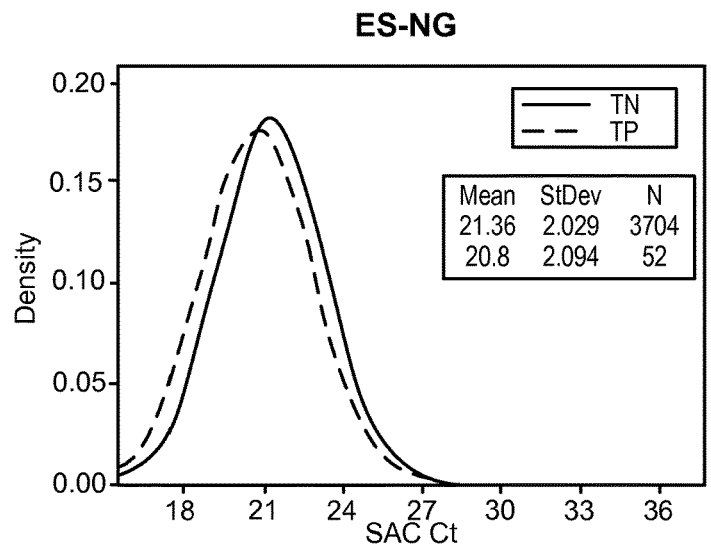
Figure 4E:
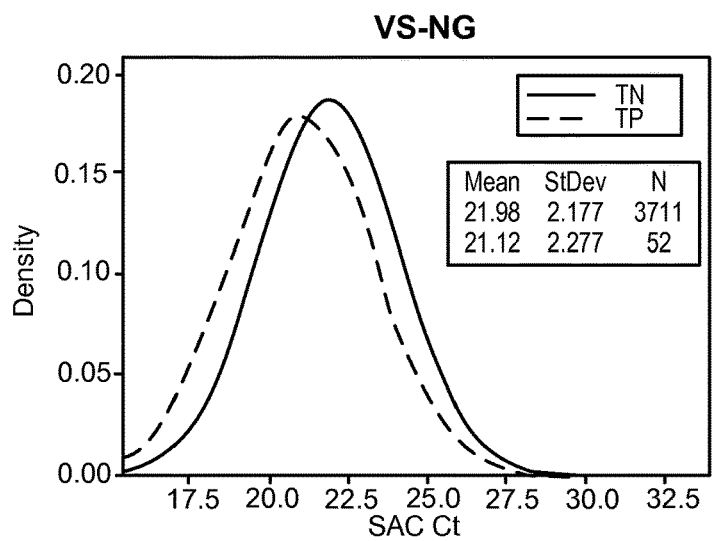
Figure 4F:
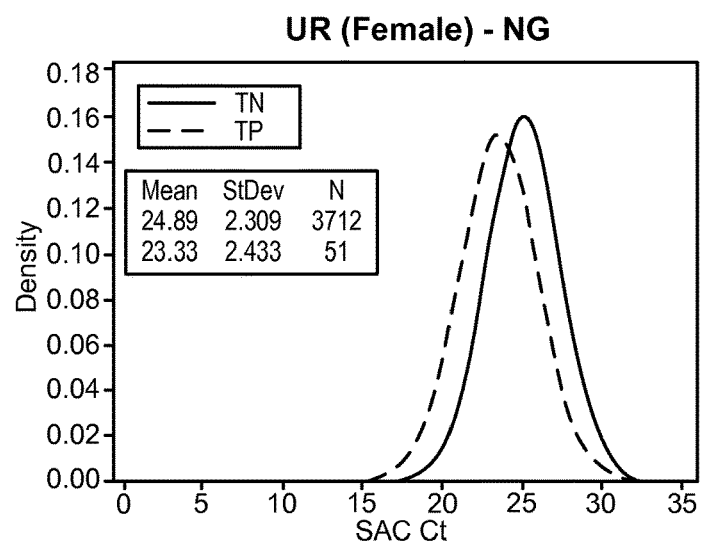
Figure 4G:
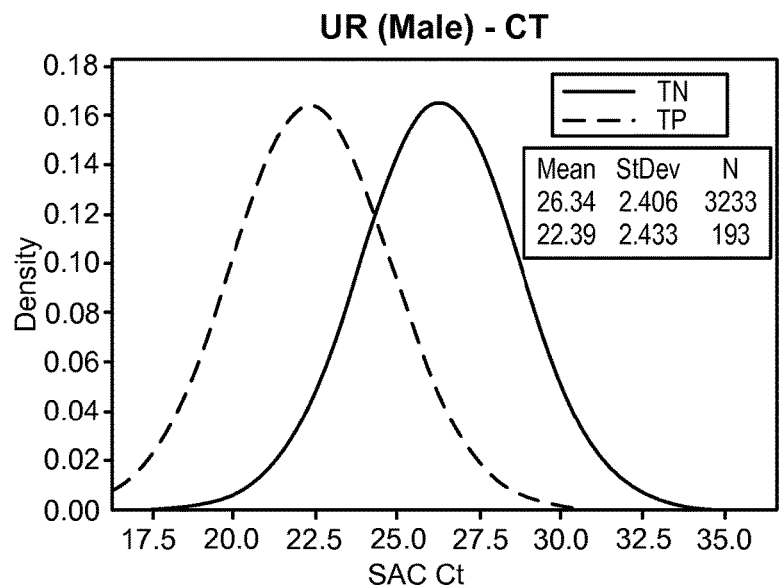
Figure 4H:
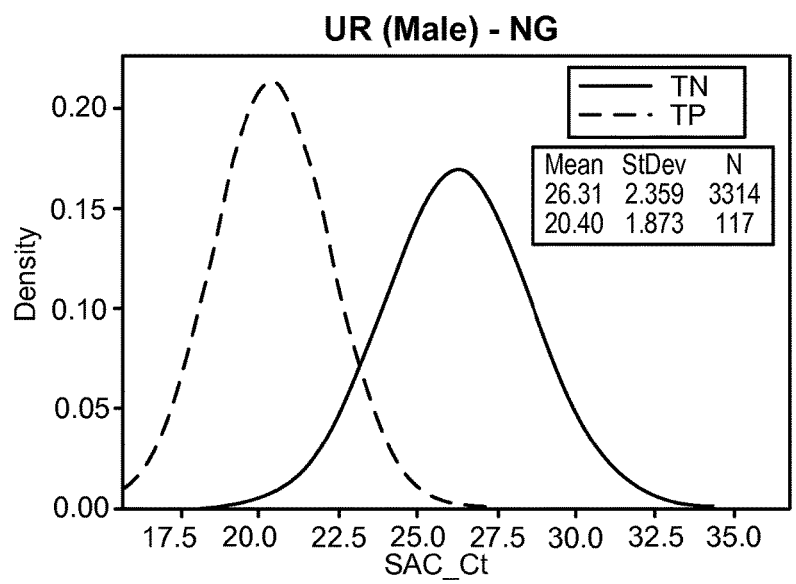

FIG. 1A-B shows (A) Ct values for NG2 and NG4 detection and (B) Ct values for CT1 and CT2 detection, using three different real time PCR conditions, as described in Example 2.

FIG. 2 shows the patient infected status grid, as discussed in Example 4. For female subjects, where swab results from both comparator assays were negative and urine results for both competitor assays were positive, infected status was determined separately for the two sample types. In such cases, the patient infected status for the swab sample was considered to be negative and the patient infected status for the urine sample was considered to be positive.

FIGS. 3A-D shows the (A) sensitivity and (B) specificity of CT detection by five currently available assays and the assay described herein ("Xpert CT/NG Assay"), and the (C) sensitivity and (D) specificity of NG detection by five currently available assays and the assay described herein ("Xpert CT/NG Assay"). VS=vaginal swab; ES=endocervical swab.

FIG. 4A-H shows results from the study discussed in Example 5, in which patient samples assayed in the Xpert CT/NG Assay were also screened for elevated genomic copy number on the GeneXpert®. The term "SAC" is used to refer to HMBS, which was assayed as the indicator of genomic copy number. In each panel, "TN" refers to "True Negatives," and "TP" refers to "True Positives." (A) Endocervical Sample (ES)-SAC results for samples testing negative or positive for CT; (B) Vaginal Sample (VS)-SAC results for samples testing negative or positive for CT; (C) Female urine samples-SAC results for samples testing negative or positive for CT; (D) Endocervical Sample (ES)-SAC results for samples testing negative or positive for NG; (E) Vaginal Sample (VS)-SAC results for samples testing negative or positive for NG; (F) Female urine samples-SAC results for samples testing negative or positive for NG; (G) Male urine samples-SAC results for samples testing negative or positive for CT; and (H) Male urine samples-SAC results for samples testing negative or positive for NG.

Figure 5:
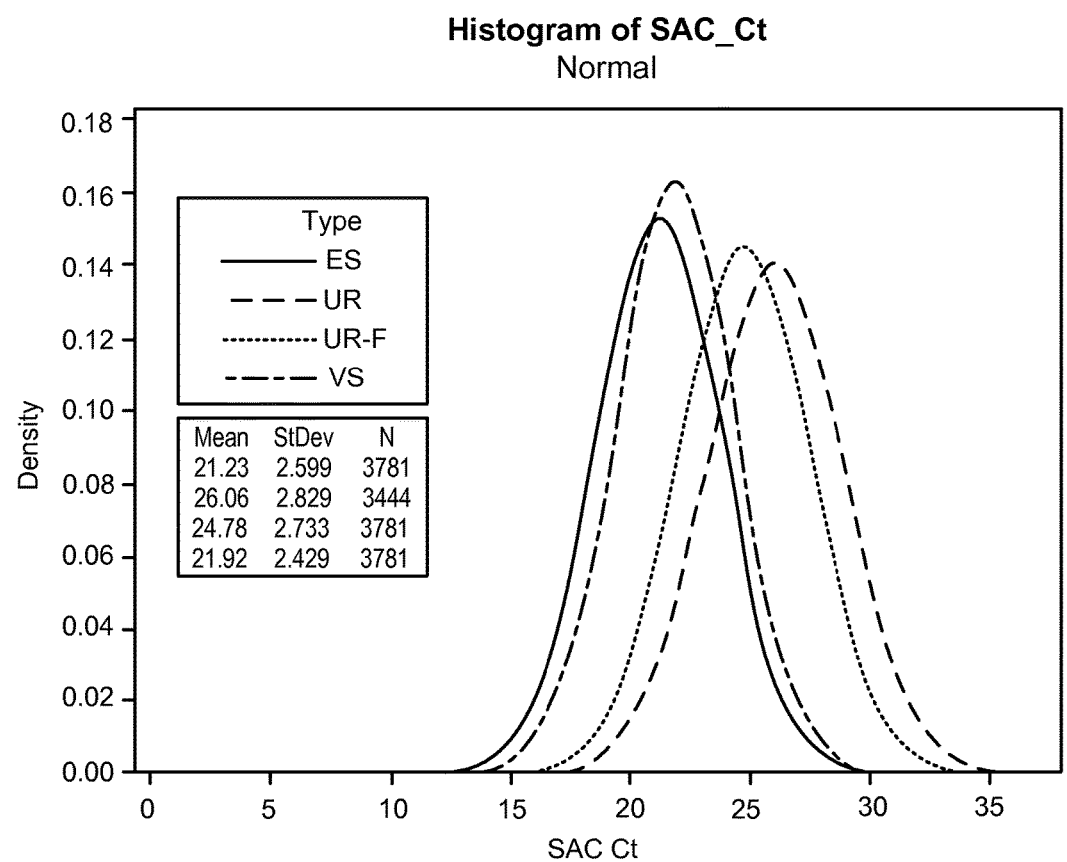

FIG. 5 shows that the genomic copy number level differs between sample types; endocervical sample (ES); male urine sample (UR); female urine sample (UR-F); and vaginal sample (VS). In particular, genomic copy number level was lower in urine than in vaginal or endocervical samples.

Figure 6A:
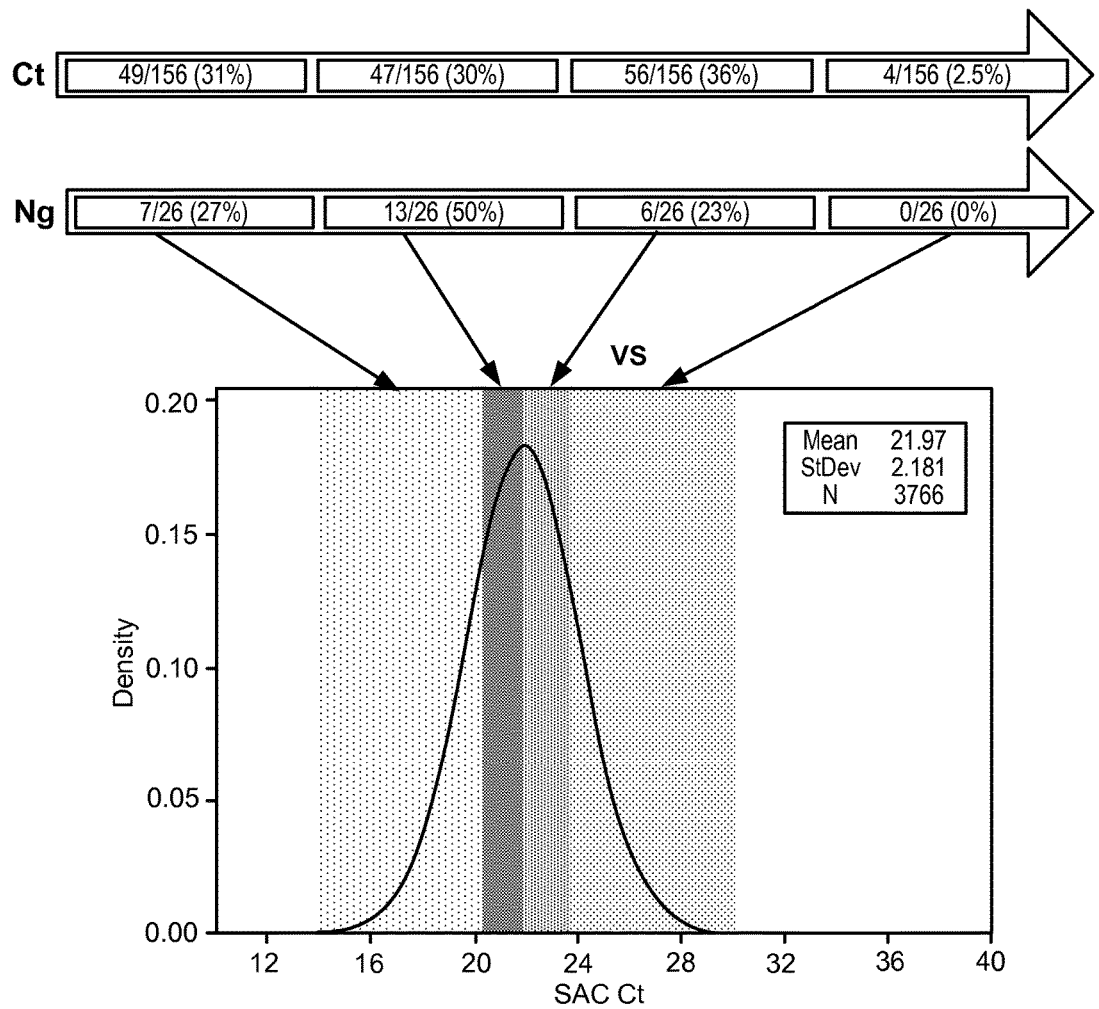
Figure 6B:
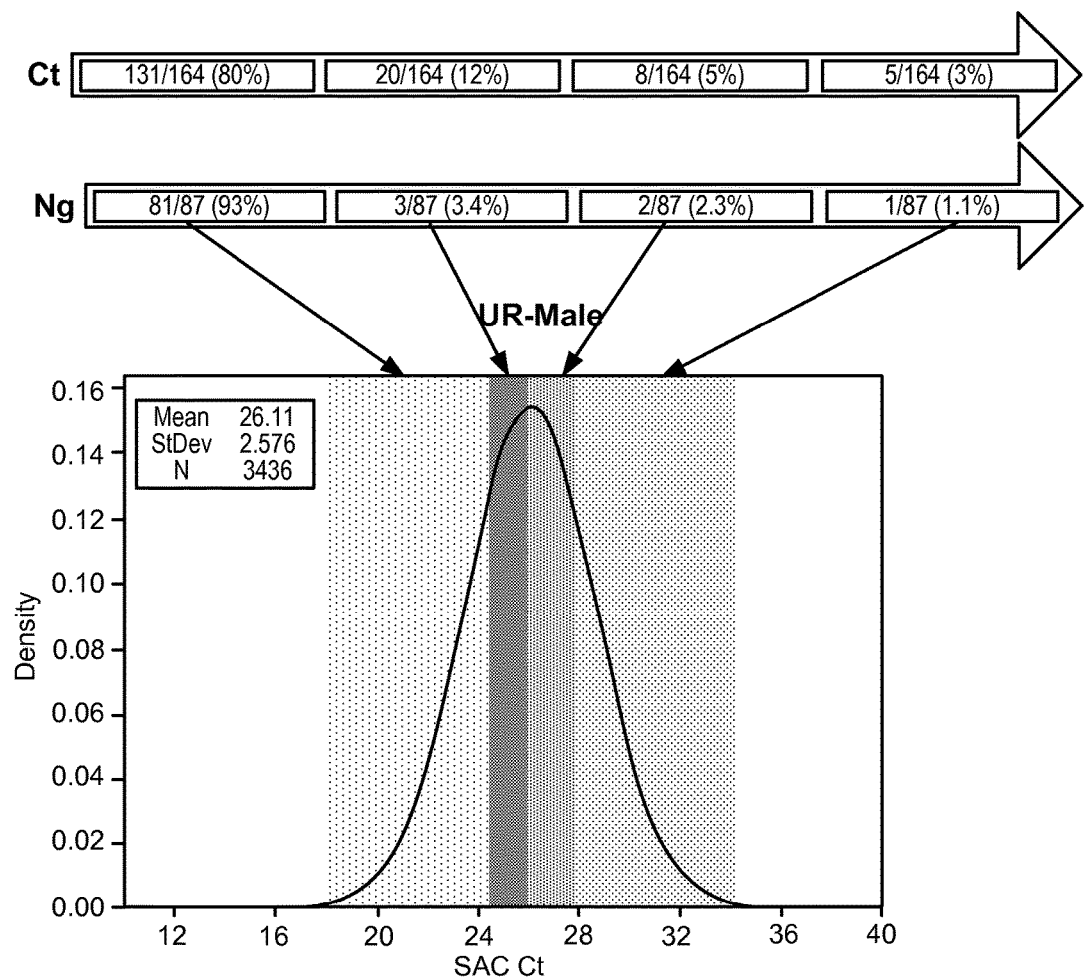
Figure 6C:
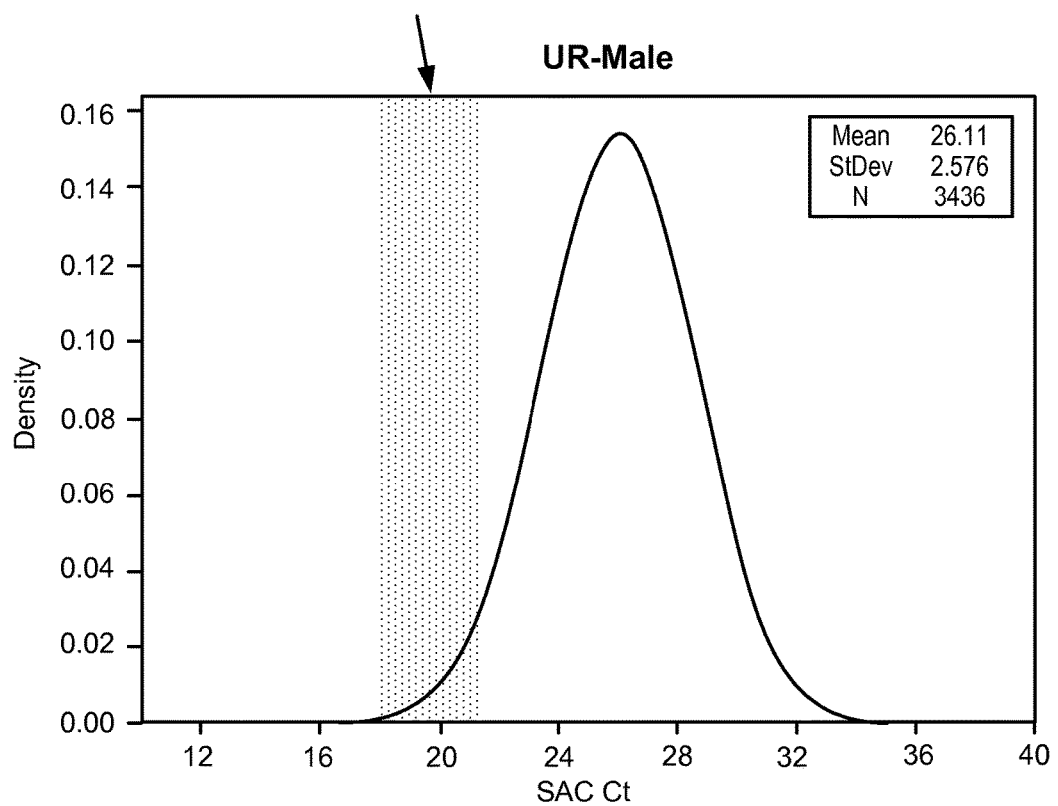

FIG. 6A-C shows genomic copy number in different sample types as a function of infection status. (A) self-collected vaginal samples: samples that were negative for CT and NG were characterized by a SAC Ct of about 24 or greater, whereas samples that were positive for infection tended to have a SAC Ct of about 20 or less; (B) male urine samples: samples that were negative for CT and NG were characterized by a SAC Ct of about 28 or greater, whereas samples that were positive for infection tended to have a SAC Ct of about 24 or less; (C) in male urine, of 32 CT/NG coinfections, all 32 occurred in the left-most decile of SAC values, i.e., all had SAC Cts of less than 24.

Figure 7:
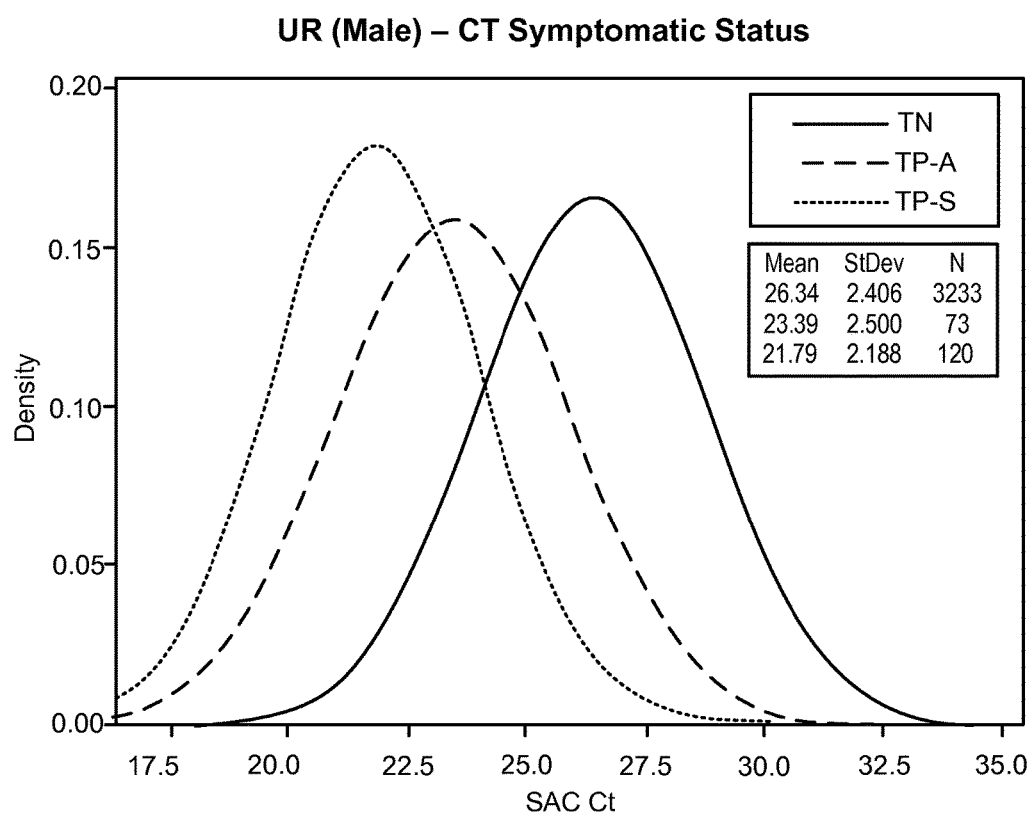

FIG. 7 shows genomic copy number values in male urine broken down by symptomatic status: true negative (TN); true positive-asymptomatic (TN-A); true positive-symptomatic (TP-S). SAC Ct values were lower for symptomatic subjects who were positive for CT/NG infection, intermediate for asymptomatic subjects who were positive for CT/NG infection, and higher for true negative subjects. CT/NG-negative subjects with SAC Ct values of less than about 24 may have a different urogenital infection and are candidates for further testing.

Figure 8:
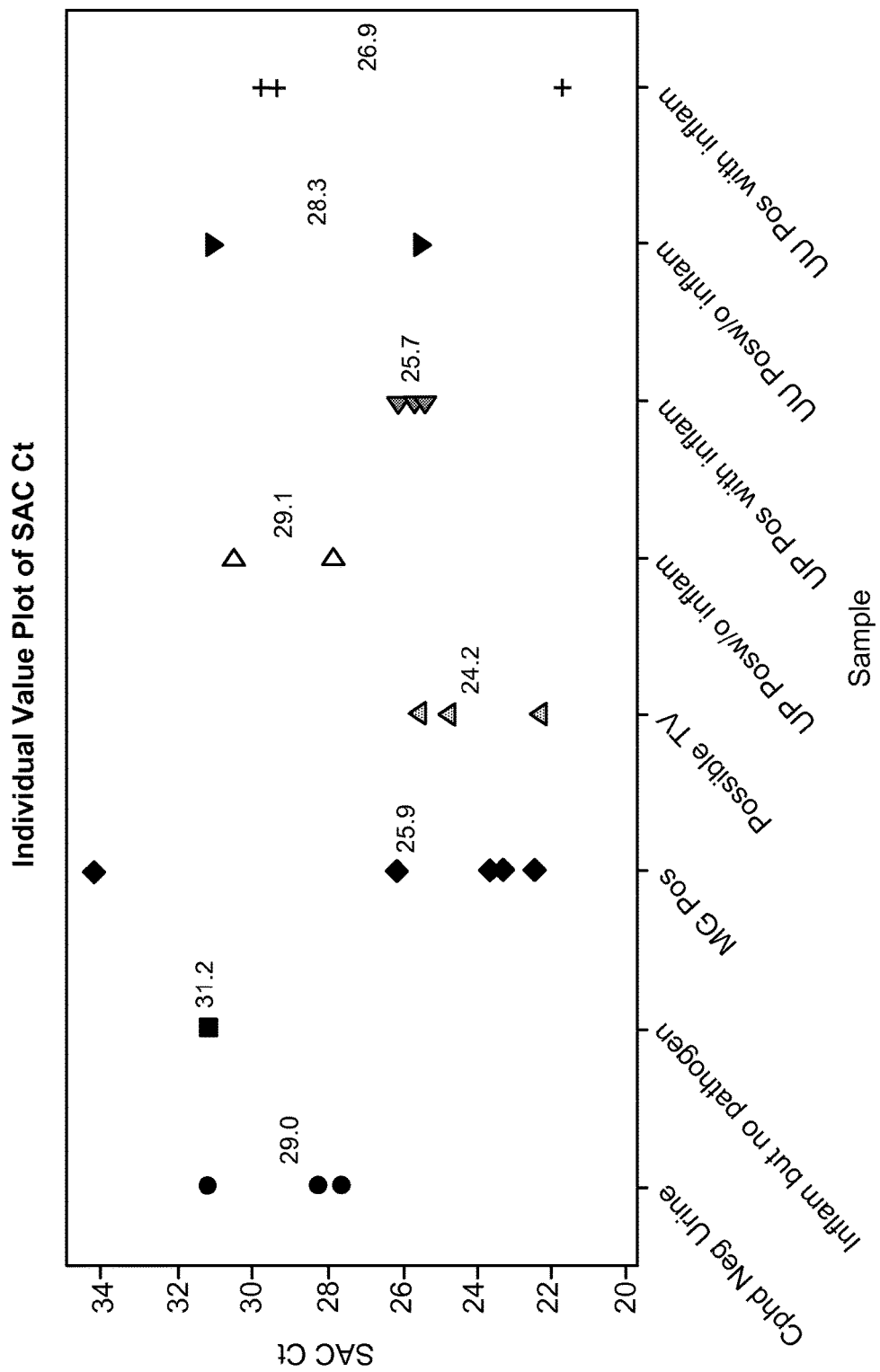

FIG. 8 shows urine genomic copy number (SAC Ct values) in various conditions (from left to right): negative control (urine from healthy subjects); inflammation, but no pathogen; *mycoplasma genitalium* positive; possible *trichomonas vaginalis; ureaplasma parvum* positive without inflammation; *ureaplasma parvum* positive with inflammation; *ureaplasma urealyticum* positive without inflammation; and *ureaplasma urealyticum* positive with inflammation.

Figure 9:
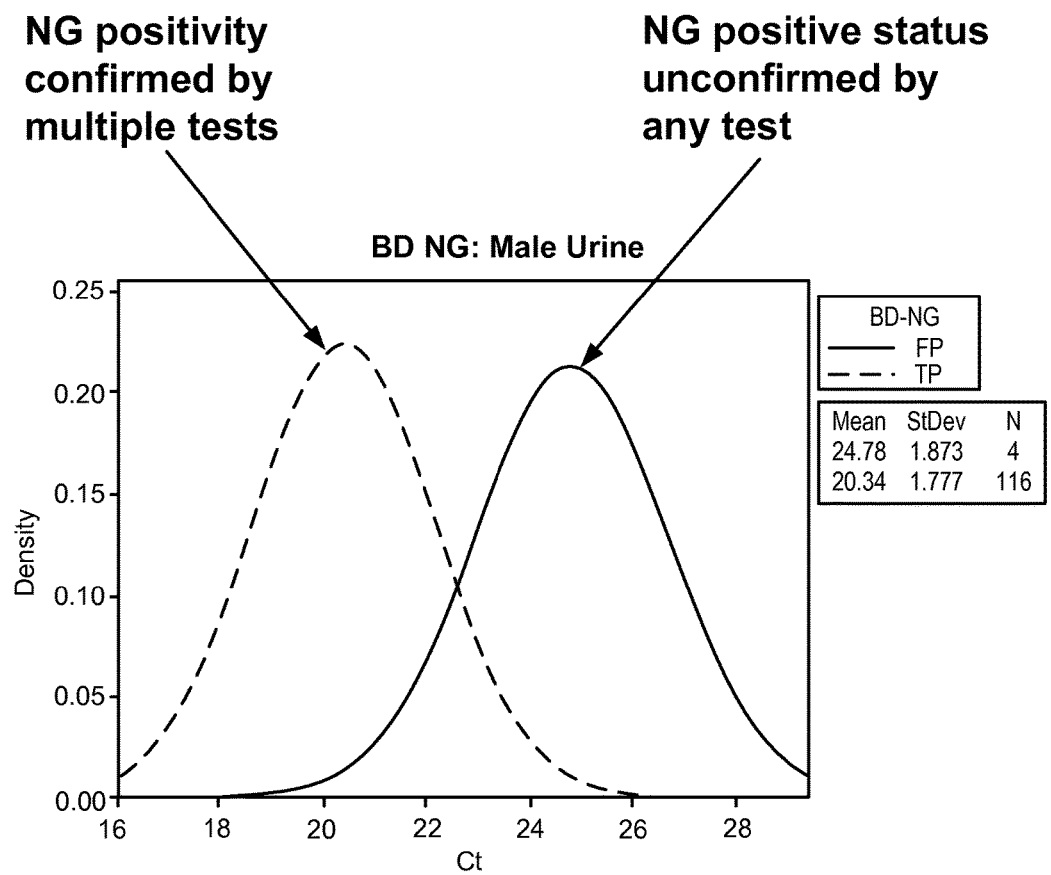

FIG. 9 shows that genomic copy number can be used to identify false positivity.

7. DETAILED DESCRIPTION

Compositions and methods for detecting *Chlamydia trachomatis* (CT) and *Neisseria gonorrhoeae* (NG) are provided. In particular, CT and NG markers and panels of markers useful in the detection of CT and NG are provided.

In addition, the present invention provides methods and kits for quantifying genomic copy number in a urogenital sample as a marker of infection and inflammation. Prior genomic copy number analyses derive information from gains or losses of entire chromosomes or amplifications or deletions at individual chromosomal loci that are known to be associated with disease. In contrast, the screening method described herein is based on assaying an indicator of the number of genomes (e.g., the total amount of genomic DNA) in a sample from an individual as a marker of infection and inflammation.

7.1. Definitions

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "detectably different" refers to a set of labels (such as dyes) that can be detected and distinguished simultaneously.

As used herein, the terms "patient" and "subject" are used interchangeably to refer to a human. In some embodiments, the methods described herein may be used on samples from non-human animals, e.g., canines, felines, primates, equines, and other non-human mammals.

As used herein, the terms "oligonucleotide," "polynucleotide," "nucleic acid molecule," and the like, refer to nucleic acid-containing molecules, including but not limited to, DNA. The terms encompass sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyladenine, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a single-stranded polynucleotide having fewer than 500 nucleotides. In some embodiments, an oligonucleotide is 8 to 200, 8 to 100, 12 to 200, 12 to 100, 12 to 75, or 12 to 50 nucleotides long. Oligonucleotides may be referred to by their length, for example, a 24 residue oligonucleotide may be referred to as a "24-mer."

As used herein, the term "complementary" to a target gene (or target region thereof), and the percentage of "complementarity" of the probe sequence to the target gene sequence is the percentage "identity" to the sequence of target gene or to the complement of the sequence of the target gene. In determining the degree of "complementarity" between probes used in the compositions described herein (or regions thereof) and a target gene, such as those disclosed herein, the degree of "complementarity" is expressed as the percentage identity between the sequence of the probe (or region thereof) and sequence of the target gene or the complement of the sequence of the target gene that best aligns therewith. The percentage is calculated by counting the number of aligned bases that are identical as between the 2 sequences, dividing by the total number of contiguous nucleotides in the probe, and multiplying by 100. When the term "complementary" is used, the subject oligonucleotide is at least 90% complementary to the target molecule, unless indicated otherwise. In some embodiments, the subject oligonucleotide is at least 91%, at least 92%, at least 93%, at least 94%, at least 95%, at least 96%, at least 97%, at least 98%, at least 99%, or 100% complementary to the target molecule.

A "primer" or "probe" as used herein, refers to an oligonucleotide that comprises a region that is complementary to a sequence of at least 8 contiguous nucleotides of a target nucleic acid molecule, such as a target gene. In some embodiments, a primer or probe comprises a region that is complementary to a sequence of at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a target molecule. When a primer or probe comprises a region that is "complementary to at least x contiguous nucleotides of a target molecule," the primer or probe is at least 95% complementary to at least x contiguous nucleotides of the target molecule. In some embodiments, the primer or probe is at least 96%, at least 97%, at least 98%, at least 99%, or 100% complementary to the target molecule.

The term "nucleic acid amplification," encompasses any means by which at least a part of at least one target nucleic acid is reproduced, typically in a template-dependent manner, including without limitation, a broad range of techniques for amplifying nucleic acid sequences, either linearly or exponentially. Exemplary means for performing an amplifying step include polymerase chain reaction (PCR), ligase chain reaction (LCR), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), digital amplification, and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8, Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

Unless otherwise indicated, the term "hybridize" is used herein refer to "specific hybridization" which is the binding, duplexing, or hybridizing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. A "stringent hybridization" and "stringent hybridization wash conditions" in the context of nucleic acid hybridization (e.g., as in array, Southern, or Northern hybridization) are sequence-dependent and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions for filter hybridizations are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. Dependency of hybridization stringency on buffer composition, temperature, and probe length are well known to those of skill in the art (see, e.g., Sambrook and Russell (2001) Molecular Cloning: A Laboratory Manual (3rd ed.) Vol. 1-3, Cold Spring Harbor Laboratory, Cold Spring Harbor Press, N.Y.).

A "sample," as used herein, includes urine samples (including samples derived from urine samples), endocervical swabs, vaginal swabs, urethral swabs, rectal swabs, eye swabs, throat swabs (oropharyngeal swabs), liquid cytology samples, and other types of human samples, such as blood, stool, and biopsy samples. The term sample also includes diluted and/or buffered forms of the above samples, for example, a buffer into which a swab sample has been placed, a urine sample to which a buffer has been added, and the like.

An "endogenous control," as used herein refers to a moiety that is naturally present in the sample to be used for detection. In some embodiments, an endogenous control is polynucleotide found in human cells in the sample. In some some embodiments, the endogenous control is a human DNA (such as a genomic DNA). Non-limiting exemplary endogenous controls include HMBS (hydroxymethylbilane synthase), GAPDH, beta-actin, and beta-globin. In some embodiments, an endogenous control is selected that can be detected in the same manner as the CT and NG markers are detected and, in some embodiments, simultaneously with the CT and NG markers.

An "exogenous control," as used herein, refers to a moiety that is added to a sample to be used for detection. An exogenous control is typically selected that is not expected to be present in the sample to be used for detection, or is present at very low levels in the sample such that the amount of the moiety naturally present in the sample is either undetectable or is detected at a much lower level than the amount added to the sample as an exogenous control. In some embodiments, an exogenous control comprises a nucleotide sequence that is not expected to be present in the sample type used for detection of the target genes. In some embodiments, an exogenous control comprises a nucleotide sequence that is not known to be present in the species from whom the sample is taken. In some embodiments, an exogenous control comprises a nucleotide sequence from a different species than the subject from whom the sample was taken. In some embodiments, an exogenous control comprises a nucleotide sequence that is not known to be present in any species. In some embodiments, an exogenous control is selected that can be detected in the same manner as the CT and NG markers are detected and, in some embodiments, simultaneously with the CT and NG markers. In some embodiments, an exogenous control is a bacterial DNA. In some some embodiments, the bacterium is a species not expected to be found in the sample type being tested.

In the present disclosure, "a sequence selected from" encompasses both "one sequence selected from" and "one or more sequences selected from." Thus, when "a sequence selected from" is used, it is to be understood that one, or more than one, of the listed sequences may be chosen.

In the present disclosure, a method that comprises detecting a "a set of CT and NG markers consisting of . . . " involves detection of only the CT and NG markers of the set, and not any further CT or NG markers. The method may comprise additional components or steps, however, such as detecting endogenous and/or exogenous controls. Similarly, a method or composition that comprises "a set of CT and NG marker primer pairs consisting of . . . " and/or "a set of CT and NG marker probes consisting of . . . " can include primer pairs and/or probes for only the CT and NG markers of the set, and not for any other CT or NG markers. The method or composition may comprise additional components, however, such as one or more endogenous control primer pairs and/or one or more exogenous control primer pairs.

As used herein, an "indicator of genomic copy number" refers to any biomarker than indicates the number of host genomes present in a sample. In this context, "host" refers to the individual from which the sample is derived. Thus, the biomarker is one that can be used to quantitate the level of host genomic DNA. If the DNA of other one or more other organisms is present in the sample, the biomarker is generally one that is not present in the contaminating DNA. Typical indicators of genomic copy number are nucleic acid sequences that have a known copy number that is expected to be relatively constant across different individual of the species from which the sample is derived. In some embodiments, for example, the indicator of genomic copy number for a mammal is a nucleic acid sequence that is expected to be present in the genome of a mammal in one or two copies. Nucleic acid sequence indicators of genomic copy number can DNA or RNA sequences.

The term "control genomic copy number level" is used to refer to level obtained when an indicator of genomic copy number is measured in a sample obtained from a region of an animal's body (e.g., a sample obtained from the urogenital tract of the mammal) that his not afflicted with any disease or disorder (e.g., infection and/or inflammation). The control genomic copy number level can be expressed as a specific value or as a range of values.

A "genomic copy number level that is higher than a control genomic copy number level" refers to a level that is above a specific value corresponding to the control genomic copy number level or above the upper end of a range that defines the control genomic copy number level.

As used herein, the phrase "is indicative of the presence of infection or inflammation" means that a particular result tends to indicate that infection and/or inflammation are likely present. This phrase does not imply a definitive determination that infection and/or inflammation is present. A definitive determination can be made based on further examination or testing that a medical practitioner deems appropriate. Furthermore, this phrase does not require that a determination be made as to which condition, infection or inflammation, may be present based only on the particular result. Rather, it is contemplated that a positive result will be considered in light of other examination or text results to arrive at a differential diagnosis.

7.2. Detection Methods

7.2.1. General Methods for Detecting CT and NG

The present inventors have developed an assay for detecting CT and NG in human samples, such as urine and swabs, with high sensitivity and specificity. The assay comprises detecting at least three markers selected from NG2, NG4, CT1, and CT2, which are shown below in Table 1. The presently described assays have several advantages over existing assays for CT and NG. For example, the present assays detect CT genomic sequences rather than plasmid sequences, which can be deleted or lost, leading to strains of CT that can evade detection. The present assays can also be run in under 2 hours using an automated system, for example, the GeneXpert® system, on an on-demand basis. Existing tests can require several days for a laboratory to complete a batch and send results.

Compositions and methods for detecting CT and NG are provided.

In some embodiments, a method of detecting CT and NG comprises detecting the presence of NG markers NG2 and NG4, and a CT marker selected from CT1 and CT2. In some embodiments, a method of detecting CT and NG comprises detecting NG2, NG4, and CT1. In some embodiments, a method of detecting CT and NG comprises detecting NG2, NG4, and CT1, and at least one endogenous control. In some embodiments, a method of detecting CT and NG comprises detecting NG2, NG4, and CT1, and at least one endogenous control and at least one exogenous control. In some embodiments, a method of detecting CT and NG comprises detecting NG2, NG4, and CT2. In some embodiments, a method of detecting CT and NG comprises detecting NG2, NG4, and CT2, and at least one exogenous control. In some embodiments, a method of detecting CT and NG comprises detecting NG2, NG4, and CT2, and at least one exogenous control.

In the present disclosure, the term "target gene" is used for convenience to refer to NG2, NG4, CT1, and CT2 genes and also to other target genes, such as exogenous and/or endogenous controls. Thus, it is to be understood that when a discussion is presented in terms of a target gene, that discussion is specifically intended to encompass NG2, NG4, CT1, and CT2 target genes, and/or other target genes.

In some embodiments, one or more target genes is detected in a urine sample. In some embodiments, one or more target genes is detected in a swab sample, such as an endocervical swab sample, a urethral swab sample, an oropharyngeal swab, or a vaginal swab sample (including a self-collected vaginal swab sample). In some embodiments, a buffer is added to the urine sample and/or a swab sample is placed in a buffer after collection.

In some embodiments, detection of NG2 and NG4 indicates the presence of NG in the sample, and therefore NG infection in the subject. In some embodiments, detection of only one of NG2 or NG4 indicates no NG in the sample, and therefore no NG infection in the subject. In some embodiments, detection of CT1 indicates the presence of CT in the sample, and therefore CT infection in the subject. In some embodiments, detection of CT2 indicates the presence of CT in the sample, and therefore CT infection in the subject. In some embodiments, failure to detect an endogenous control or an exogenous control in a sample in which none of the NG or CT marker genes are detected indicates a failure of the assay. In some embodiments, detecting a target gene comprises forming a complex comprising a polynucleotide and a nucleic acid selected from a target gene, a DNA amplicon of a target gene, and a complement of a target gene. In some embodiments, detecting a target gene comprises real-time PCR.

In some embodiments, the CT/NG assay is run on-demand to detect CT and NG in a subject's sample while the subject waits for the results. In some embodiments, the CT/NG assay is run while a female subject is in labor to determine whether she has CT or NG, which may pose a risk to the newborn. In some embodiments, the CT/NG assay is part of routine physical examinations, such as yearly or semi-yearly physical examinations. In some embodiments, for example, when the CT/NG assay is run on demand, a urine sample is analyzed without added buffer.

In some embodiments, less than 3 ml, less than 2 ml, or about 1 ml of urine or urine mixed with a buffer is used in the present methods. In some embodiments, less than 3 ml, less than 2 ml, or about 1 ml of the liquid phase from a swab sample in buffer is used in the present methods. In some embodiments, the sample is analyzed without a centrifugation step. Thus, in some embodiments, the present methods are carried out in the absence of centrifugation.

The clinical sample to be tested is, in some embodiments, fresh (i.e., never frozen). In some embodiments, the sample is a frozen specimen.

In some embodiments, the sample to be tested is obtained from an individual who has one or more risk factors and/or symptoms of CT and/or NG infection, such as multiple sexual partners, inconsistent or no condom use, history of sexually transmitted infection, presence of vaginal discharge, painful urination, lower abdominal pain, lower back pain, fever, pain during intercourse, bleeding between menstrual periods, rectal pain, rectal discharge, rectal bleeding, discharge from the penis, and painful or swollen testicles. In some embodiments, the sample to be tested is obtained from an individual who has a history of CT and/or NG infection.

In some embodiments, methods described herein can be used for routine screening of healthy individuals with no risk factors or symptoms. In some embodiments, methods described herein are used to screen asymptomatic individuals having one or more of the above-described risk factors.

In some embodiments, the methods described herein can be used to assess the efficacy of CT and/or NG treatment. For example, in some embodiments, the present assay is used to monitor treatment or is used to demonstrate the absence of infection following a full course of treatment.

In any of the embodiments described herein, two or more target genes may be detected concurrently or simultaneously in the same or separate assay reactions. In some embodiments, three target genes, such as NG2, NG4, and CT1, are detected in the same assay reaction. In some some embodiments, along with the three target genes, one or more controls are detected in the same assay reaction, such as an endogenous control and/or an exogenous control.

In some embodiments, a method of facilitating diagnosis of CT and/or NG infection in a subject is provided. Such methods comprise detecting NG2, NG4, and at least one of CT1 and CT2 in a sample from the subject. In some embodiments, the method comprises detecting NG2, NG4, and CT1. In some embodiments, the method comprises detecting NG2, NG4, and CT2. In some embodiments, information concerning the detection of NG2, NG4, and at least one of CT1 and CT2 in the sample from the subject is communicated to a medical practitioner. A "medical practitioner," as used herein, refers to an individual or entity that diagnoses and/or treats patients, such as a health maintenance organization, a hospital, a clinic, a physician's office, a physician, a nurse, or an agent of any of the aforementioned entities and individuals. In some embodiments, detecting NG2, NG4, and at least one of CT1 and CT2 is carried out at a laboratory that has received the subject's sample from the medical practitioner or agent of the medical practitioner. The laboratory carries out the detection by any method, including those described herein, and then communicates the results to the medical practitioner. A result is "communicated," as used herein, when it is provided by any means to the medical practitioner. In some embodiments, such communication may be oral or written, may be by telephone, in person, by e-mail, by mail or other courier, or may be made by directly depositing the information into, e.g., a database accessible by the medical practitioner, including databases not controlled by the medical practitioner. In some embodiments, the information is maintained in electronic form. In some embodiments, the information can be stored in a memory or other computer readable medium, such as RAM, ROM, EEPROM, flash memory, computer chips, digital video discs (DVD), compact discs (CDs), hard disk drives (HDD), magnetic tape, etc.

In some embodiments, methods of detecting the presence of CT and/or NG in a sample from a subject are provided. In some embodiments, the method comprises obtaining a sample from a subject and providing the sample to a laboratory for detection of NG2, NG4, and at least one of CT1 and CT2 in the sample. In some embodiments, the method further comprises receiving a communication from the laboratory that indicates whether or not NG and/or CT was detected in the sample. In some embodiments, NG is present if both NG2 and NG4 are detected in the sample. In some embodiments, CT is present if either CT1 or CT2 is detected in the sample. In some embodiments, a communication from the laboratory indicates whether or not each target gene was detected in the sample. In some embodiments, a communication from the laboratory indicates whether or not NG and/or CT was detected in the sample. A "laboratory," as used herein, is any facility that detects the CT and NG target genes in a sample by any method, including the methods described herein, and communicates the presence or absence of the CT and/or NG target genes to a medical practitioner. In some embodiments, a laboratory is under the control of a medical practitioner. In some embodiments, a laboratory is not under the control of the medical practitioner.

When a laboratory communicates the results of the assay to a medical practitioner, in some embodiments, the laboratory communicates the result for each pathogen (i.e., NG and CT), such as "NG detected, CT not detected," "NG not detected, CT detected," "NG not detected, CT not detected," or "NG detected, CT detected," or indicates that the assay failed, such as "invalid."

As used herein, when a method relates to detecting CT and/or NG, determining the presence of CT and/or NG, monitoring CT and/or NG treatment, and/or confirming the success of CT and/or NG treatment, the method includes activities in which the steps of the method are carried out, but the result is negative for the presence of CT and/or NG. That is, detecting, determining, and monitoring, etc., CT and/or NG include instances of carrying out the methods that result in either positive or negative results.

In some embodiments, more than one target gene is detected simultaneously in a single reaction. In some embodiments, NG2, NG4, and CT1 are detected simultaneously in a single reaction. In some embodiments, NG2, NG4, and CT2 are detected simultaneously in a single reaction. In some embodiments, NG2, NG4, and CT1 and at least one endogenous control and/or at least one exogenous control are detected simultaneously in a single reaction. In some embodiments, NG2, NG4, and CT2 and at least one endogenous control and/or at least one exogenous control are detected simultaneously in a single reaction. In some embodiments, NG2, NG4, and CT1 and an endogenous control and an exogenous control are detected simultaneously in a single reaction. In some embodiments, NG2, NG4, and CT2 and an endogenous control and an exogenous control are detected simultaneously in a single reaction.

7.2.1.1. Exemplary Controls

In some embodiments, a control is an endogenous control DNA. An endogenous control DNA may be any DNA suitable for the purpose, such as, for example, DNA from human cells expected to be present in the sample. Non-limiting exemplary endogenous control DNAs include HMBS, GAPDH, beta-actin, and beta-globin. An endogenous control, in some embodiments, is used to confirm that the sample integrity, that adequate sample was present in the reaction, and the like.

In some embodiments, a control is an exogenous control DNA. An exogenous control may, in some embodiments, be used to determine if the detection assay reaction has failed, and therefore the results are not meaningful. For example, if an exogenous control DNA is not amplified in the assay reaction, then a negative result for the target genes is likely not meaningful because the absence may reflect the reaction failing rather than the target genes (and therefore the target organisms) being absent. Reaction failure can occur for any number of reasons, including, but not limited to, the presence of a reaction inhibitor in the sample (an "inhibitory sample"), compromised reagents, etc. An exogenous control may be added at any stage of the sample collection and analysis. For example, in some embodiments, the exogenous control DNA is added to the sample at the time a buffer is added, is added to the sample when it is received by the diagnostic laboratory, is added to the sample immediately prior to analysis, or is added to the sample during analysis (as a non-limiting example, before or at the same time as addition of the amplification reagents).

In some embodiments, the level of an endogenous control and/or an exogenous control is determined contemporaneously, such as in the same assay or batch of assays, as detection of the target genes in a sample. In some embodiments, an assay comprises reagents for detecting NG2, NG4, and at least one of CT1 and CT2, and an endogenous control simultaneously in the same assay reaction. In some embodiments, an assay comprises reagents for detecting NG2, NG4, and at least one of CT1 and CT2, and an exogenous control simultaneously in the same assay reaction. In some embodiments, an assay comprises reagents for detecting NG2, NG4, and at least one of CT1 and CT2, an endogenous control, and an exogenous control simultaneously in the same assay reaction. In some some embodiments, for example, an assay reaction comprises primer sets for amplifying a portion of each of NG2, NG4, and at least one of CT1 and CT2, a primer set for amplifying an endogenous control and/or a primer set for amplifying an exogenous control, and detectably different labeled probes for detecting the amplification products (such as, for example, TaqMan® probes with detectably different dyes for each different amplicon to be detected).

7.2.2. General Methods of Screening a Mammal for Infection or Inflammation of the Urogenital Tract The invention also provides, in some embodiments, a method of screening a mammal for infection or inflammation of the urogenital tract. This method entails assaying a sample obtained from the urogenital tract of the mammal for an indicator of genomic copy number, wherein a genomic copy number level that is higher than a control genomic copy number level is indicative of the presence of infection or inflammation of the urogenital tract. In some embodiments, the method entails assaying the sample for a plurality of indicators of genomic copy number, which can increase the reliability of the assay.

Any indicator of genomic copy number can be employed in this screening method. In some embodiments, the indicator of genomic copy number is a nucleic acid sequence, which can be a DNA or RNA sequence. In some embodiments, a nucleic acid sequence that is expected to be present in the genome of the mammal in one or two copies. Examples of such nucleic acid sequences include, but are not limited to, a hydroxymethylbilane synthase (HMBS), glyceraldehyde 3-phosphate dehydrogenase (GAPDH), beta-actin, and beta-globin nucleic acid sequences. Detection of the human HBMS nucleic acid sequence as an indicator of genomic copy number is described in the Examples.

The screening method can use any means of determining genomic copy number. Where the indicator of genomic copy number is a nucleic acid sequence, the screening method can be based on assays that include one or more of nucleic acid amplification, nucleic acid hybridization, and/or nucleic acid sequencing. In some embodiments, amplification-based assays are used. Convenient amplification assays include PCR, e.g., real-time PCR or endpoint PCR. Considerations for carrying out these methods are described in detail herein, and those of skill in the art will readily appreciate that these considerations apply equally to the detection of CT/NG genes and to a nucleic acid sequence indicator of genomic copy number. In some embodiments that are useful for human screening, the indicator of genomic copy number is a human HBMS sequence, which is amplified, e.g., using primers including SEQ ID NO:113 and SEQ ID NO:114. Detection and quantitation of amplicons produced by nucleic acid amplification can be carried out using methods known in the art and/or described herein. For example, a probe, such as, e.g., a Taqman® probe, can be used to detect and/or quantify amplicons in a real-time PCR reaction. In some embodiments, where the indicator of genomic copy number is a human HBMS sequence that is amplified, e.g., using primers including SEQ ID NO:113 and SEQ ID NO:114, a suitable probe includes SEQ ID NO:115.

Probes may also be used for detection and quantitation in hybridization assays. Conditions for specifically hybridizing the probes and/or primers to their nucleic acid targets generally include the combinations of conditions that are employable in a given hybridization procedure to produce specific hybrids, which may easily be determined by one of skill in the art. Such conditions typically involve controlled temperature, liquid phase, and contact between a probe and a target. Hybridization conditions vary depending upon many factors including probe/primer concentration, target length, target and probe/primer G-C content, solvent composition, temperature, and duration of incubation. At least one denaturation step may precede contact of the probes/primers with the targets. Alternatively, both the probe/primer and nucleic acid target may be subjected to denaturing conditions together while in contact with one another, or with subsequent contact of the probe/primer with the biological sample. Hybridization may be achieved with subsequent incubation of the probe/primer/sample in, for example, a liquid phase that is compatible with subsequent steps of the assay. For example if no subsequent enzymatic amplification is required the liquid phase may comprise about a 50:50 volume ratio mixture of 2-4×SSC and formamide, at a temperature in the range of about 25 to about 55° C. Higher hybridization temperatures are typically employed if formamide is not included in the liquid. Temperatures are also adjusted based on the length of the complementary sequences that are participating in the hybridization. Hybridization times range from about several seconds for PCR primers to about 96 hours. Other conditions may be readily employed for specifically hybridizing the probes/primers to their nucleic acid targets present in the sample, as would be readily apparent to one of skill in the art.

Upon completion of a suitable incubation period, non-specific binding of probes to sample (or sample-derived) nucleic acid may be removed by one or a series of washes. Temperature, salt, and formamide, etc., concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes without formamide may be carried out for conventional nucleic acids at a temperature in the range of about 65 to about 80° C. with about 0.2× to about 4×SSC and about 0.1% to about 1% of a non-ionic detergent such as Nonidet P-40 (NP40). If lower stringency washes are required, the washes may be carried out at a lower temperature with an increased concentration of salt.

A wide variety of formats for hybridization-based assays are available and suitable for use in assaying an indicator of genomic copy number. In some embodiments, the probe(s) can be immobilized on a substrate. For example, where multiple indicators of genomic copy number are to be assayed simultaneously in one hybridization assay a plurality of probes can be immobilized on the substrate. This approach has been used, for example, in array comparative genomic hybridization (aCGH). In aCGH, the probes are not labeled, but rather are immobilized at distinct locations on a substrate, as described in WO 96/17958. In this context, the probes are often referred to as the "target nucleic acids." The sample nucleic acids are typically labeled to allow detection of hybridization complexes. The sample nucleic acids used in the hybridization may be detectably labeled prior to the hybridization reaction. Alternatively, a detectable label may be selected which binds to the hybridization product. In dual- or multi-color aCGH, the target nucleic acid array is hybridized to two or more collections of differently labeled nucleic acids, either simultaneously or serially. For example, sample nucleic acids and reference nucleic acids (e.g., from a control) are each labeled with a separate and distinguishable label. Differences in intensity of each signal at each target nucleic acid spot can be detected as an indication of a copy number difference. Although any suitable detectable label can be employed for aCGH, fluorescent labels are typically the most convenient. Array-based relative copy number determinations can be obtained using a commercial service, such as, e.g., the Affymetrix-authorized SeqWright.

Genomic copy number determinations can also be carried out by nucleic acid sequencing, e.g., high-throughput DNA sequencing. In some embodiments, amplification methods are employed to produce amplicons suitable for high-throughput (i.e., automated) DNA sequencing. Generally, amplification methods that provide substantially uniform amplification of target nucleotide sequences are employed in preparing DNA sequencing libraries having good coverage. In the context of automated DNA sequencing, the term "coverage" refers to the number of times the sequence is measured upon sequencing. The counts obtained are typically normalized relative to a reference sample or samples to determine relative copy number. Thus, upon performing automated sequencing of a plurality of target amplicons, the normalized number of times the sequence is measured reflects the number of target amplicons including that sequence, which, in turn, reflects the number of copies of the target sequence in the sample DNA.

Amplification for sequencing may involve emulsion PCR isolates in which individual DNA molecules along with primer-coated beads are present in aqueous droplets within an oil phase. Polymerase chain reaction (PCR) then coats each bead with clonal copies of the DNA molecule followed by immobilization for later sequencing. Emulsion PCR is used in the methods by Marguilis et al. (commercialized by 454 Life Sciences), Shendure and Porreca et al. (also known as "Polony sequencing") and SOLiD sequencing, (developed by Agencourt, now Applied Biosystems). Another method for in vitro clonal amplification for sequencing is bridge PCR, where fragments are amplified upon primers attached to a solid surface, as used in the Illumina Genome Analyzer. Some sequencing methods do not require amplification, for example the single-molecule method developed by the Quake laboratory (later commercialized by Helicos). This method uses bright fluorophores and laser excitation to detect pyrosequencing events from individual DNA molecules fixed to a surface. Pacific Biosciences has also developed a single molecule sequencing approach that does not require amplification.

After in vitro clonal amplification (if necessary), DNA molecules that are physically bound to a surface are sequenced. Sequencing by synthesis, like dye-termination electrophoretic sequencing, uses a DNA polymerase to determine the base sequence. Reversible terminator methods (used by Illumina and Helicos) use reversible versions of dye-terminators, adding one nucleotide at a time, and detect fluorescence at each position in real time, by repeated removal of the blocking group to allow polymerization of another nucleotide. Pyrosequencing (used by 454) also uses DNA polymerization, adding one nucleotide species at a time and detecting and quantifying the number of nucleotides added to a given location through the light emitted by the release of attached pyrophosphates.

Pacific Biosciences Single Molecule Real Time (SMRT™) sequencing relies on the processivity of DNA polymerase to sequence single molecules and uses phospho-linked nucleotides, each type labeled with a different colored fluorophore. As the nucleotides are incorporated into a complementary DNA strand, each is held by the DNA polymerase within a detection volume for a greater length of time than it takes a nucleotide to diffuse in and out of that detection volume. The DNA polymerase then cleaves the bond that previously held the fluorophore in place and the dye diffuses out of the detection volume so that fluorescence signal returns to background. The process repeats as polymerization proceeds.

Sequencing by ligation uses a DNA ligase to determine the target sequence. Used in the Polony method and in the SOLiD technology, this method employs a pool of all possible oligonucleotides of a fixed length, labeled according to the sequenced position. Oligonucleotides are annealed and ligated; the preferential ligation by DNA ligase for matching sequences results in a signal informative of the nucleotide at that position. Any of these DNA sequencing techniques may be employed in the methods described herein.

Any mammal can be screened for infection or inflammation of the urogenital tract as described herein. In some embodiments, the mammal is a human. The mammal can be male or female. In some embodiments, the individual mammal screened has one or more risk factors and/or symptoms of urogenital infection or inflammation, such as multiple sexual partners, inconsistent or no condom use, history of sexually transmitted infection, presence of vaginal discharge, painful urination, lower abdominal pain, lower back pain, fever, pain during intercourse, bleeding between menstrual periods, discharge from the penis, and painful or swollen testicles. In some embodiments, the individual screened is one that has been identified as having at least one clinical symptom of urogenital infection or inflammation. In some embodiments, the individual being screened is one that has been identified as having a symptom of, or as having, *Chlamydia trachomatis* (CT), *Neisseria gonorrhoeae* (NG), *Mycoplasma genitalium* (MG), *Ureaplasma, Trichomonas, Leptotrichia*, or *Sneathia* infection.

In some embodiments, methods described herein can be used for routine screening of healthy individuals with no risk factors or symptoms. In some embodiments, methods described herein are used to screen asymptomatic individuals having one or more of the above-described risk factors. In some embodiments, the individual mammal screened is one that has had a prior sexually transmitted disease.

In some embodiments, the method is carried out to help distinguish inflammation or infection from cancer. In some embodiments, the mammal is a human male who has previously been tested for prostate-specific antigen (PSA) as an indicator of prostate cancer and found to have a sufficiently elevated PSA level to be a candidate for a biopsy. PSA is typically measured by immunoassay of a blood sample. The risk of prostate cancer increases with increasing PSA levels. In 1994, a PSA level of 4 ng/mL was chosen as a decision level for biopsies in the clinical trial upon which the U.S. Food and Drug Administration based adding prostate cancer detection in men age 50 and over as an approved indication for the first commercially available PSA test. Other clinical trials have used 3 or 4 ng/mL as the biopsy decision level. The 2007 NCCN guideline used 2.5 ng/mL.

Biopsies, which are offered after a positive PSA test result, are painful and can lead to complications such as excessive bleeding and infection. For this reason, and because PSA levels can change for many reasons other than cancer, PSA screening remains controversial. Two common causes of high PSA levels are enlargement of the prostate (benign prostatic hypertrophy) and infection in the prostate (prostatis). Thus, after a positive PSA result, a subject can screened for infection or inflammation of the urogenital tract as described herein to determine whether the subject may have an elevated PSA due to infection, rather than cancer. A positive PSA result can be, e.g., a PSA level equal to, or greater than, 2.5 ng/mL PSA or any biopsy decision level employed in standard medical practice. This screening for elevated genomic copy number can be carried out, e.g., in men being screened for prostate cancer or being monitored for prostate cancer recurrence or progression.

In some embodiments, the screening methods described herein can entail identifying the subject as one in which the elevated PSA may be due to infection, rather than cancer if the genomic copy number level in the sample is higher than a control genomic copy number level. In such subjects, prostate biopsy can be deferred until after infection is either ruled out or resolved. In some embodiments, the screening method described herein additionally comprises performing one or more additional assay(s) (or causing one or more additional assay(s) to be performed) of the same, or a different, sample from the subject for a pathogen that may be contributing to the elevated PSA level. In some embodiments, the method can entail performing (or causing to be performed) one or more additional assays for elevated genomic copy number and/or one or more additional PSA tests before considering biopsy. In some embodiments, the method can entail treating the subject for infection and optionally re-assaying for elevated genomic copy number and/or PSA. Antibiotic treatments for prostatitis are well known and include, e.g., doxycycline. In some embodiments, if, in an initial screening assay of a subject positive for PSA, the genomic copy number level in the sample was higher than a control genomic copy number level, the subject could treated for infection or the putative infection permitted to resolve on its own. A second screening assay could then be performed, and if the genomic copy number level was found to be normal (i.e., at or below a control level or within a control range), the PSA test could be repeated. A positive PSA result after a negative result in the screen for elevated genomic copy number would indicate that the positive PSA result was not likely due to infection and therefore more likely to be due to cancer. Thus, the screen for elevated genomic copy number could help to ensure that unnecessary biopsies, with their attendant risks, are not performed.

The method of screening for infection or inflammation of the urogenital tract is carried out on a urogenital tract sample, which includes urine and a urethral swab sample or, for female subjects, a vaginal swab sample, and an endocervical swab sample. In some embodiments, samples may be obtained and processed as described herein with respect to CT/NG detection.

In some embodiments, the method of screening for infection or inflammation of the urogenital tract additionally includes assaying a sample from the mammal for the presence of a protein, peptide, or nucleic acid sequence that is indicative of a pathogen, e.g., a pathogen known to infect the urogenital tract. In some embodiments, the screening method includes assaying for *Chlamydia trachomatis* (CT) and *Neisseria gonorrhoeae* (NG), e.g., using the detection methods described herein. In some embodiments, the screening method includes assaying for *Mycoplasma genitalium* (MG), *Ureaplasma, Trichomonas, Leptotrichia*, or *Sneathia* infection, e.g., using any convenient detection method. The pathogen assay can, but need not, be carried out simultaneously with the genomic copy number assay described herein, in the same sample or in a different sample. The pathogen assay can also, but need not, be carried out in the same reaction mixture as the genomic copy number assay. For example, the pathogen assay and the genomic copy number assay can be carried out by multiplex PCR, e.g., multiplex real-time PCR.

In some embodiments, the method of screening for infection or inflammation of the urogenital tract additionally comprises assaying the same, or a different, sample from the mammal for the presence and/or level of a microRNA (miRNA) that is correlated with inflammation. mRNAs that are correlated with inflammation are known. Illustrative miRNAs and the pro- or anti-inflammatory genes that they regulate are shown below (miRNAs are listed first and separated by a colon from the genes that they regulate).

let-7a, let-7b, let-7c, let-7d, let-7e, let-7f, let-7g, let-7i, miR-98: Casp3, Ccr7, Fgf11, Fgf5, Gdf6, Il13, Masp1, Olr1, Osmr.

miR-106a, miR-106b, miR-17, miR-20a, miR-20b, miR-93: F3, Mgll, Mink1, Osm, Pdcd11g2, Ptger3, Stat3.

miR-1192, miR-495: Atrn, Bcl11a, Clcf1, Cyp26b1, Fgf7, Ptpra.

miR-126-5p: Ap3b1, Cast, Cntnap2, Fgf7, Gfra2, Hdac4, Hipk2, Il13, Il17a, Il1f5, Il7, Ptger3.

miR-128: Bmi1, Csf1, Hipk2, Lifr, Nfx1, Pik3r1.

miR-130a, miR-130b, miR-301a, miR-301b, miR-721: Cast, Cbfb, Chst1, Eda, Erbb2ip, Hprt1, Impdh1, Inhbb, Irf1, Plaa, Pparg, Tnf.
miR-140, miR-876-3p: Bmp2, Fgf9, Hdac4, Hdac7, Rac1, Spred1, Tnfsf8, Vegfa.
miR-144: Cxcl12, Eda, Gdf10, Lifr, Ptgs2, Tnfsf11, Ttn.
miR-155: Cebpb, Cyp26b1, Fgf7, Gdf6, Ms4a1, Sdcbp, Sp3.
miR-15a, miR-15b, miR-16, miR-195, miR-322, miR-497: Cd28, Eda, Fgf7, Ghr, Ifnk, Il10ra, Pik3r1, Spred1, Vegfa.
miR-181a, miR-181b, miR-181c, miR-181d: Cd4, Il1a, I17, Lif, Phf2011, Prkcd, Tnf, Tnfrsf11b, Txndc5.
miR-182: Bcl11a, Chst1, Fgf9, Gdf6, Hdac9, Ndrg1, Rac1, Sh2d1a, Sp3, Zfp36.
miR-186: Cast, Cntnap2, Cxcl13, Gdf6, Il13ra1, Pdgfc, Vegfa.
miR-19a, miR-19b: Cast, Cbfb, Chst1, Cntfr, Cxcl12, F3, Impdh1, Plaa, Tnf.
miR-200c, miR-429: Gpr68, Hmgb3, Il13, Ntf3, Prkca, Ripk2, Vegfa.
miR-221, miR-222: Cbfb, Cd4, Cxcl12, Fos, Hipk2, Lifr, Ntf3, Spred2.
miR-23a, miR-23b: Btla, Ccl7, Cxcl12, Erbb2ip, Fas, Grem1, Irf1, Prkca, Stat5b, Tnfaip6, Tpst1.
miR-26a, miR-26b: Cmtm4, Inhbb, Pawr, Ppp3cb, Prkcd, Prkcq, Ptgs2, Srgap1.
miR-27a, miR-27b: Bmi1, Bmp3, Cd28, Cntnap2, Csf1, Fgf1, Grem1, Hipk2, Irf4, Lifr, Mstn, Pparg, Rgs1.
miR-291a-3p, miR-294, miR-295, miR-302b, miR-302d: Bcl11a, Bcl6, Cdkn1a, Cyp26b1, Dock2, F3, Il28ra, Lefty1, Lefty2.
miR-297b-3p, miR-466b-3-3p, miR-466d-3p: Bmp3, Cebpb, Cmtm8, Cntnap2, Hdac4, Il12b, Il1a, Il3, Lyst, Pik3r1, Prkca, Sele, Sp3, Spred1, Spred2, Vegfa.
miR-29a, miR-29b, miR-29c: Atrn, Bcl11a, Hdac4, Il1rap, Lif, Pdgfc, Tnfrsf1a, Vegfa, Zfp36.
miR-30a, miR-30b, miR-30c, miR-30d, miR-30e, miR-384-5p: Cbfb, Chst1, Chst2, Hdac9, Hipk2, Ifnar2, Il1a, Irf4, Lepr, Lifr, Lyst, Pawr, Pik3cd.
miR-325: Akt1, Cd86, Cdkn1a, Cxcl13, Cxcr3, Ephx2, F2, Fcer1a, Grem1, Il1r1, Il22ra2, Il23a, Impdh2, Ntf3, Pik3r1.
miR-338-5p: Atrn, Cast, Cyp26b1, Hdac4, Hipk2, Hmgb3, Il19, Nfkb1, Ntf3, Ptx3, Sh2d1a, Sp3.
miR-340-5p: Bcl11a, Bmi1, Cast, Cmtm6, Cntnap2, Cyp26b1, Fgf7, Hdac4, Hipk2, Il10, Il4, Nfkb1, Osm.
miR-369-3p: Ccl22, Cebpb, Gfra2, Inhbb, Prkca, Sp3, Spred1.
miR-374: Akt1, Bmp2, Ccl22, Cebpb, Cyp26b1, Il10, Ntf3, Sp3.
miR-410: Csf2, F3, Fgf7, Il4, Nr3c1, Pdgfa, Sp3, Vegfa.
miR-466d-5p, miR-466k: Atrn, Bmp3, Bmp4, Cd40lg, Chst2, Gfra2, Il28ra, Inhba, Itgam, Muc4.
miR-466f-3p: Eda, Hipk2, Il1rap, Pik3r1, Ppp3cb, Spred1, Stat5b.
miR-590-3p: Btla, Ccl15, Cd28, Cx3cl1, Fcgr2b, Fgf5, Hipk2, Il17f, Sp3.
miR-669f: Atrn, Cdkn1a, Cmtm8, Cntfr, Cyp26b1, Eda, F3, Fgf4, Fgf7, Gdf6, Hipk2, Hmgb3, Ifngr1, Il16, Il7, Map2k3, Mink1, Ncf1, Nr3c1, Pik3r1, Prkcd, Ptpra, Spred1, Stat3, Ttn, Vegfa.
miR-669h-3p, miR-669k: Cd8a, Hdac7, Hipk2, Ntf3, Pparg, Ppp3cb, Sp3.
miR-692: Bcl11a, Bcl6, Cd86, Fcer1a, Hprt1, Pou2f2, Socs2, Sp3, Tnfsf12, Vegfa.
miR-694: Ccl8, Gdf6, Hipk2, Il1rap, Il7, Nr3c1, Prkca, Sh2d1a, Sp3.
miR-712: Bcl6, Cntnap2, Csf1, Il2ra, Inhba, Itgam, Lepr, Lif, Pou2f2, Stat5a, Vegfa.
miR-743a, miR-743b-3p: Cyp26b1, Fgf5, Hdac4, Hipk2, Il13ra1, Inhbb, Ppp3cb.
miR-9: Ap3b1, Cmtm6, Cxcl11, Hdac5, Inhbb, Pdgfc.

See also Ryan et al. (April 2012) "microRNA Regulation of Inflammatory Responses" Annual Review of Immunology 30: 295-312 (which is hereby incorporated by reference for its description of miRNAs that are correlated with inflammation). The miRNA assay can, but need not, be carried out simultaneously with the genomic copy number assay described herein. The miRNA assay can also, but need not, be carried out in the same reaction mixture as the genomic copy number assay. For example, the miRNA assay and the genomic copy number assay can be carried out by multiplex PCR, e.g., multiplex real-time PCR.

If the genomic copy number level in the sample is higher than a control genomic copy number level, the screening method can additionally include identifying the mammal as one who may have infection or inflammation of the urogenital tract. Genomic copy number levels can differ between sample types. Example 5 demonstrates that, using measurement of HMBS on the GeneXpert® as the indicator of genomic copy number, the genomic copy number level was lower in urine than in vaginal or endocervical samples. See FIG. 5. FIG. 6A-C shows genomic copy number in different sample types as a function of infection status. In self-collected vaginal samples (6A), samples that were negative for CT and NG were characterized by a SAC Ct of about 24 or greater, whereas samples that were positive for infection tended to have a SAC Ct of about 20 or less. Therefore, in such assays of self-collected vaginal samples, in some embodiments, a SAC Ct of less than or equal to 18, 19, 20, 21, or 22 can be used as an indicator of infection. In male urine (6B), samples that were negative for CT and NG were characterized by a SAC Ct of about 28 or greater, whereas samples that were positive for infection tended to have a SAC Ct of about 24 or less. In male urine, of 32 CT/NG coinfections, all 32 occurred in the left-most decile of SAC values, i.e., all had SAC Cts of less than 24 (6C). Therefore, in such assays of male urine, in some embodiments, a SAC Ct of less than 22, 23, 24, 25, or 26 can be used as an indicator of infection.

Genomic copy number also correlates with symptomatic status, as can be seen from FIG. 7. SAC Ct values in male urine were lower for symptomatic subjects who were positive for CT/NG infection, intermediate for asymptomatic subjects who were positive for CT/NG infection, and higher for true negative subjects.

If the sample is positive for a pathogen, such as *Chlamydia trachomatis* (CT) and/or *Neisseria gonorrhoeae* (NG), a positive result for elevated genomic copy number can, in some embodiments, confirm the presence of infection, providing greater confidence in identifying the mammal as one who may have infection or inflammation of the urogenital tract. However, if the sample is positive for the pathogen, but the genomic copy number level in the sample is not higher than a control genomic copy number level, this may indicate a false positive, in which case, it may be advisable to retest the mammal for the pathogen. Alternatively, if the sample is positive for the pathogen, but the genomic copy number level in the sample is not higher than a control genomic copy number level, the mammal may be an asymptomatic carrier of the pathogen. If the sample is negative for a pathogen, such as *Chlamydia trachomatis*

(CT) and/or *Neisseria gonorrhoeae* (NG), a positive result for elevated genomic copy number can, in some embodiments, lead to the identification of the mammal as one who may be infected with a different pathogen or may have inflammation of the urogenital tract that is not due to infection.

In some embodiments, the method of screening for infection or inflammation of the urogenital tract additionally entails communicating the assay result to a medical practitioner, as described above for CT/NG detection and/or recording the assay result, and/or a diagnosis based at least in part on the assay result, in a patient medical record. The medical record can be in paper form and/or can be maintained in a computer-readable medium. The medical record can be maintained by a laboratory, physician's office, a hospital, a health maintenance organization, an insurance company, and/or a personal medical record website. In some embodiments, the methods of the invention include informing the individual screened of the presence of an elevated genomic copy number and/or of a diagnosis based at least in part on this finding. The patient can be informed verbally, in writing, and/or electronically.

In some embodiments, the methods described herein can entail ordering and/or performing one or more additional assay(s) or examination(s) or causing one or more additional assay(s) or examination(s) to be performed. For example, if genomic copy number is determined to be elevated, an assay or examination for a pathogen can be performed. The pathogen assay can be a protein- or nucleic acid-based assay or a clinical assay. Illustrative pathogens to be assayed for include *Chlamydia trachomatis* (CT), *Neisseria gonorrhoeae* (NG), *mycoplasma* (e.g., *Mycoplasma genitalium* (MG)), *Ureaplasma, Trichomonas, Leptotrichia,* and *Sneathia*. In some embodiments, an initial assay may be performed for a first pathogen and genomic copy number determined (in the same, or a different, sample) that indicates an absence of infection with the first pathogen accompanied by an elevated genomic copy number level. In such cases, the method can entail ordering and/or performing one or more additional assays for a second, different pathogen or causing one or more such additional assay(s) to be performed. The second, different pathogen can be e.g. a bacterium, a fungus or a virus. In some embodiments, if genomic copy number is determined to be elevated, an assay or examination for a urogenital condition characterized by inflammation, such as, e.g., autoimmune urethritis, prostatitis, bladder cancer, prostate cancer, kidney cancer, may be ordered and/or performed or caused to be performed. Additional assays can be performed on the same sample as used to determine genomic copy number level or on a different sample, as appropriate or convenient.

In some embodiments, at least two additional assays are performed on the subject of the initial assay (or a sample therefrom) to monitor for any change in genomic copy number level over time. The additional assay can be a repeat of the initial assay or can have a different format and/or employ a different sample. In some embodiments, at least two or more clinical assays are performed to monitor for the appearance of, or any change in, on or more clinical symptoms over time. Such additional assays can be performed to assess the efficacy of treatment, to demonstrate the absence of infection and/or inflammation following a full course of treatment or to demonstrate relapse.

In some embodiments, the method of the invention includes treating a mammal determined to have infection or inflammation of the urogenital tract, wherein this determination is based, at least in part, on a determination of elevated genomic copy number. In some embodiments, the method entails receiving results from any of the screening methods described herein and initiating and/or altering therapy for the infection or inflammation of the urogenital tract or causing therapy to be initiated and/or altered (e.g., by prescription). If the mammal has not been previously diagnosed with an infection or inflammation of the urogenital tract, the method can entail initiating therapy (or causing it to be initiated). If the mammal has one or more symptoms of an infection or inflammation of the urogenital tract and has been treated accordingly, the method can entail altering therapy based on a more specific and/or definitive diagnosis (e.g., a differential diagnosis) based on elevated genomic copy number, optionally in combination with other assay and/or examination results. If the mammal has had one or more symptoms of an infection or inflammation of the urogenital tract and has been treated accordingly, but the genomic copy number is at or below a control level (or is at a significantly lower level than previously), this may indicate resolution of the infection or inflammation (or diminution in severity of the condition, e.g., in response to treatment). Accordingly, in some embodiments, the method entails ceasing or altering therapy upon determining that the genomic copy number is at or below a control level (or is at a significantly lower level) in a mammal that was being treated for infection or inflammation of the urogenital tract. In such a mammal, the method can entail, periodic monitoring, where the detection of genomic copy number at above a control level (or at a significantly higher level than previously) is indicative of relapse, in which case therapy could be resumed (if it had been ceased) or altered.

Exemplary Sample Preparation 7.2.2.1. Exemplary Buffers

In some embodiments, a buffer is added to a urine sample. In some embodiments, the buffer is added within one hour, two hours, three hours, or six hours of the time the urine sample was collected (e.g., voided). In some embodiments, a buffer is added to the urine sample within one hour, two hours, three hours, or six hours before the sample is analyzed by the methods described herein.

In some embodiments, a swab sample is placed in a buffer. In some embodiments, the swab sample is placed in the buffer within one hour, two hours, three hours, or six hours of the time the swab sample was collected. In some embodiments, the swab sample is placed in a buffer within one hour, two hours, three hours, or six hours before the sample is analyzed by the methods described herein.

Non-limiting exemplary commercial buffers include PreservCyt (Hologic, Bedford, Mass.), SurePath (BD, Franklin Lakes, N.J.), and CyMol (Copan Diagnostics, Murrietta, Calif.).

7.2.2.2. Exemplary DNA Preparation

Sample DNA can be prepared by any appropriate method. In some embodiments, target DNA is prepared by contacting a sample with a lysis buffer and binding DNA to a DNA binding substrate, such as a glass or silica substrate. The binding substrate may have any suitable form, such as a particulate, porous solid, or membrane form. For example, the support may comprise hydroxycellulose, glass fiber, cellulose, nitrocellulose, zirconium hydroxide, titanium (IV) oxide, silicon dioxide, zirconium silicate, or silica particles (e.g., see U.S. Pat. No. 5,234,809). Many such DNA binding substrates are known in the art.

In some embodiments, DNA is detected in a lysate without first isolating or separating the DNA. In some some embodiments, the sample is subject to a lysis step to release the DNA. Non-limiting exemplary lysis methods include sonication (for example, for 2-15 seconds, 8-18 µm at 36 kHz); chemical lysis, for example, using a detergent; and various commercially available lysis reagents. In some embodiments, DNA is detected are measured in a sample in which DNA has been isolated or separated from at least some other cellular components.

When the methods discussed herein indicate that a target gene is detected, such detection may be carried out on a complement of a target gene instead of, or in addition to, the target gene sequence shown herein. In some embodiments, when the complement of a target gene is detected, a polynucleotide for detection is used that is complementary to the complement of the target gene. In some some embodiments, a polynucleotide for detection comprises at least a portion that is identical in sequence to the target gene, although it may comprise modified nucleotides.

7.2.3. Exemplary Analytical Methods

As described above, methods are presented for detecting CT and/or NG in a sample from a subject. The methods comprise detecting NG2, NG4, and at least one of CT1 and CT2, and optionally detecting at least one endogenous control and/or at least one exogenous control. In some embodiments, detection of NG2 and NG4 indicates the presence of NG in the sample. In some embodiments, detection of CT1 or CT2 indicates the presence of CT in the sample. In some embodiments, the method comprises detecting NG2, NG4, and CT1. In some embodiments, the method comprises detecting NG2, NG4, and CT2.

Methods are also described above for detecting infection or inflammation of the urogenital tract by screening a sample from a mammal. These methods entail assaying a sample obtained from the urogenital tract of the mammal for an indicator of genomic copy number. In some embodiments, the indicator of genomic copy number comprises one or more nucleic acid sequence(s) that have a known copy number that is expected to be relatively constant across different individual of the species from which the sample is derived, e.g., HMBS, GAPDH, beta-actin, and beta-globin. Such nucleic acid sequences can be detected in the same manner as any target gene, including NG2, NG4, CT1, and CT2. Accordingly, those of skill will readily appreciate that the following discussion, which focuses on these target genes also applies to many indicators of genomic copy number.

Any analytical procedure capable of permitting specific detection of a target gene, such as NG2, NG4, CT1, and CT2, may be used in the methods herein presented. Such analytical procedures include, but are not limited to, PCR methods, and other methods known to those skilled in the art.

In some embodiments, the method of detecting a target gene, such as NG2, NG4, CT1, or CT2, comprises amplifying a region of the target gene. Such amplification can be accomplished by any method. Exemplary methods include, but are not limited to, real-time PCR and endpoint PCR.

When a target gene is amplified, in some embodiments, an amplicon of the target gene is formed. An amplicon may be single stranded or double-stranded. In some embodiments, when an amplicon is single-stranded, the sequence of the amplicon is related to the target gene in either the sense or antisense orientation. In some embodiments, an amplicon of a target gene is detected rather than the target gene itself. Thus, when the methods discussed herein indicate that a target gene is detected, such detection may be carried out on an amplicon of the target gene instead of, or in addition to, the target gene itself. In some embodiments, when the amplicon of the target gene is detected rather than the target gene, a polynucleotide for detection is used that is complementary to the complement of the target gene. In some embodiments, when the amplicon of the target gene is detected rather than the target gene, a polynucleotide for detection is used that is complementary to the target gene. Further, in some embodiments, multiple polynucleotides for detection may be used, and some polynucleotides may be complementary to the target gene and some polynucleotides may be complementary to the complement of the target gene.

In some embodiments, the method of detecting one or more target genes, such as NG2, NG4, CT1, or CT2, comprises PCR, as described below. In some embodiments, detecting one or more target genes comprises real-time monitoring of a PCR reaction, which can be accomplished by any method. Such methods include, but are not limited to, the use of TaqMan®, Molecular beacon, or Scorpion probes (i.e., energy transfer (ET) probes, such as FRET probes) and the use of intercalating dyes, such as SYBR green, EvaGreen, thiazole orange, YO-PRO, TO-PRO, etc.

Non-limiting exemplary conditions for amplifying a target gene, such as NG2, NG4, CT1, or CT2, include the double-denature methods described herein. In some embodiments, Taq polymerase is used for amplification. In some embodiments, the cycle is carried out at least 10 times, at least 15 times, at least 20 times, at least 25 times, at least 30 times, at least 35 times, or at least 45 times. In some some embodiments, Taq is used with a hot start function. In some embodiments, the amplification reaction occurs in a GeneXpert® cartridge, and amplification of at least three target genes occurs in the same reaction. In some embodiments, detection of the target genes occurs in less than 3 hours, less than 2.5 hours, less than 2 hours, less than 100 minutes, or less than 90 minutes from initial denaturation through the last extension.

In some embodiments, detection of a target gene comprises forming a complex comprising a polynucleotide that is complementary to a target gene or to a complement thereof, and a nucleic acid selected from the target gene, an amplicon of the target gene, and a complement of the target gene. Thus, in some embodiments, the polynucleotide forms a complex with a target gene. In some embodiments, the polynucleotide forms a complex with a complement of the target gene, such as the complementary strand of the target gene. In some embodiments, the polynucleotide forms a complex with an amplicon of the target gene. When a double-stranded target gene or amplicon is part of a complex, as used herein, the complex may comprise one or both strands of the target gene or amplicon. Thus, in some embodiments, a complex comprises only one strand of the target gene or amplicon. In some embodiments, a complex is a triplex and comprises the polynucleotide and both strands of the target gene or amplicon. In some embodiments, the complex is formed by hybridization between the polynucleotide and the target gene, complement of the target gene, or amplicon of the target gene. The polynucleotide, in some embodiments, is a primer or probe.

In some embodiments, a method comprises detecting the complex. In some embodiments, the complex does not have to be associated at the time of detection. That is, in some embodiments, a complex is formed, the complex is then dissociated or destroyed in some manner, and components from the complex are detected. An example of such a system is a TaqMan® assay. In some embodiments, when the polynucleotide is a primer, detection of the complex may comprise amplification of the target gene, a complement of the target gene, or an amplicon of a target gene.

In some embodiments the analytical method used for detecting at least one target gene in the methods set forth herein includes real-time PCR. In some embodiments, the analytical method used for detecting at least one target gene includes the use of a TaqMan® probe. The assay uses energy transfer ("ET"), such as fluorescence resonance energy transfer ("FRET"), to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that the dye signal (such as fluorescence) is detected. Signal (such as fluorescence) increases with each PCR cycle proportionally to the amount of probe that is cleaved.

In some embodiments, a target gene is considered to be detected if any signal is generated from the TaqMan probe during the PCR cycling. For example, in some embodiments, if the PCR includes 45 cycles, if a signal is generated at any cycle during the amplification, the target gene is considered to be present and detected. In some some embodiments, if no signal is generated by the end of the PCR cycling, the target gene is considered to be absent and not detected.

In addition to the TaqMan® assays, other real-time PCR chemistries useful for detecting PCR products in the methods presented herein include, but are not limited to, Molecular Beacons, Scorpion probes and intercalating dyes, such as SYBR Green, EvaGreen, thiazole orange, YO-PRO, TO-PRO, etc., which are discussed below.

In some embodiments, real-time PCR detection is utilized to detect, in a single multiplex reaction, three target genes, such as NG2, NG4, and CT1 (or CT2), and optionally, at least one endogenous control and/or at least one exogenous control. In some multiplex embodiments, a plurality of probes, such as TaqMan® probes, each specific for a different target gene, is used. In some embodiments, each target gene-specific probe is spectrally distinguishable from the other probes used in the same multiplex reaction.

In some embodiments, detection of real-time PCR products is accomplished using a dye that binds to double-stranded DNA products, such as SYBR Green, EvaGreen, thiazole orange, YO-PRO, TO-PRO, etc.

Real-time PCR is performed using any PCR instrumentation available in the art. Typically, instrumentation used in real-time PCR data collection and analysis comprises a thermal cycler, optics for fluorescence excitation and emission collection, and optionally a computer and data acquisition and analysis software.

7.2.4. Exemplary Automation and Systems

In some embodiments, a target gene is detected using an automated sample handling and/or analysis platform. In some embodiments, commercially available automated analysis platforms are utilized. For example, in some embodiments, the GeneXpert® system (Cepheid, Sunnyvale, Calif.) is utilized.

The present invention is illustrated for use with the GeneXpert system. Exemplary sample preparation and analysis methods are described below. However, the present invention is not limited to a particular detection method or analysis platform. One of skill in the art recognizes that any number of platforms and methods may be utilized.

The GeneXpert® utilizes a self-contained, single use cartridge. Sample extraction, amplification, and detection may all be carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety.)

Components of the cartridge include, but are not limited to, processing chambers containing reagents, filters, and capture technologies useful to extract, purify, and amplify target nucleic acids. A valve enables fluid transfer from chamber to chamber and contains nucleic acids lysis and filtration components. An optical window enables real-time optical detection. A reaction tube enables very rapid thermal cycling.

In some embodiments, the GenXpert® system includes a plurality of modules for scalability. Each module includes a plurality of cartridges, along with sample handling and analysis components.

After the sample is added to the cartridge, the sample is contacted with lysis buffer and released DNA is bound to a DNA-binding substrate such as a silica or glass substrate. The sample supernatant is then removed and the DNA eluted in an elution buffer such as a Tris/EDTA buffer. The eluate may then be processed in the cartridge to detect target genes as described herein. In some embodiments, the eluate is used to reconstitute at least some of the PCR reagents, which are present in the cartridge as lyophilized particles.

In some embodiments, PCR is used to amplify and detect the presence of the CT and/or NG target genes and/or target gene that indicates genomic copy number. In some embodiments, the PCR uses Taq polymerase with hot start function, such as AptaTaq (Roche).

In some embodiments, a double-denature method is used to amplify low copy number targets. A double-denature method comprises, in some embodiments, a first denaturation step followed by addition of primers and/or probes for detecting target genes. All or a substantial portion of the DNA-containing sample (such as a DNA eluate) is then denatured a second time before, in some instances, a portion of the sample is aliquotted for cycling and detection of the target genes. While not intending to be bound by any particular theory, the double-denature protocol may increase the chances that a low copy number target gene (or its complement) will be present in the aliquot selected for cycling and detection because the second denaturation effectively doubles the number of targets (i.e., it separates the target and its complement into two separate templates) before an aliquot is selected for cycling. In some embodiments, the first denaturation step comprises heating to a temperature of 90° C. to 100° C. for a total time of 30 seconds to 5 minutes. In some embodiments, the second denaturation step comprises heating to a temperature of 90° C. to 100° C. for a total time of 5 seconds to 3 minutes. In some embodiments, the first denaturation step and/or the second denaturation step is carried out by heating aliquots of the sample separately. In some embodiments, each aliquot may be heated for the times listed above. As a non-limiting example, a first denaturation step for a DNA-containing sample (such as a DNA eluate) may comprise heating at least one, at least two, at least three, or at least four aliquots of the sample separately (either sequentially or simultaneously) to a temperature of 90° C. to 100° C. for 60 seconds each. As a non-limiting example, a second denaturation step for a DNA-containing sample (such as a DNA eluate) containing enzyme, primers, and probes may comprise heating at least one, at least two, at least three, or at least four aliquots of the eluate separately (either sequentially or simultaneously) to a temperature of 90° C. to 100° C. for 5 seconds each. In some embodiments, an aliquot is the entire DNA-containing sample (such as a DNA eluate). In some embodiments, an aliquot is less than the entire DNA-containing sample (such as a DNA eluate).

In some embodiments, target genes in a DNA-containing sample, such as a DNA eluate, are detected using the following protocol: One to more aliquots of the DNA-containing sample are heated separately to 95° C. for 60 seconds each. The enzyme and primers and probes are added to the DNA-containing sample and one or more aliquots are heated separately to 95° C. for 5 seconds each. At least one aliquot of the DNA-containing sample containing enzyme, primers, and probes is then heated to 94° C. for 60 seconds. The aliquot is then cycled 45 times with the following 2-step cycle: (1) 94° C. for 5 seconds, (2) 66° C. for 30 seconds.

The present invention is not limited to particular primer and/or probe sequences. Exemplary amplification primers and detection probes are described in the Examples.

In some embodiments, an off-line centrifugation is used to improve assay results with samples with low cellular content. The sample, with or without the buffer added, is centrifuged and the supernatant removed. The pellet is then resuspended in a smaller volume of supernatant, buffer, or other liquid. The resuspended pellet is then added to a GeneXpert® cartridge as previously described.

7.2.5. Exemplary Data Analysis

In some embodiments, a computer-based analysis program is used to translate the raw data generated by the detection assays (e.g., detection of the NG and CT target genes described herein or of a target gene that indicates genomic copy number) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample or vaginal swab) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced, specific for the diagnostic or prognostic information desired for the subject.

The profile data is then prepared in a format suitable for interpretation by a treating clinician. For example, rather than providing raw data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

7.2.6. Exemplary Polynucleotides

In some embodiments, polynucleotides are provided. In some embodiments, synthetic polynucleotides are provided. Synthetic polynucleotides, as used herein, refer to polynucleotides that have been synthesized in vitro either chemically or enzymatically. Chemical synthesis of polynucleotides includes, but is not limited to, synthesis using polynucleotide synthesizers, such as OligoPilot (GE Healthcare), ABI 3900 DNA Synthesizer (Applied Biosystems), and the like. Enzymatic synthesis includes, but is not limited to, producing polynucleotides by enzymatic amplification, e.g., PCR. A polynucleotide may comprise one or more nucleotide analogs (i.e., modified nucleotides) discussed herein.

In some embodiments, a polynucleotide is provided that comprises a region that is identical to, or complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a sequence selected from NG2, NG4, CT1, and CT2 or from a target gene that indicates genomic copy number, such as e.g., HMBS, GAPDH, beta-actin, and beta-globin. In some embodiments, a polynucleotide is provided that comprises a region that is identical to, or complementary to, a span of 6 to 100, 8 to 100, 8 to 75, 8 to 50, 8 to 40, or 8 to 30 contiguous nucleotides of a sequence selected from NG2, NG4, CT1, CT2, HMBS, GAPDH, beta-actin, and beta-globin. Non-limiting exemplary polynucleotides are shown in Table 2.

In some embodiments, a polynucleotide comprises fewer than 500, fewer than 300, fewer than 200, fewer than 150, fewer than 100, fewer than 75, fewer than 50, fewer than 40, or fewer than 30 nucleotides. In some embodiments, a polynucleotide is between 6 and 200, between 8 and 200, between 8 and 150, between 8 and 100, between 8 and 75, between 8 and 50, between 8 and 40, or between 8 and 30 nucleotides long.

In some embodiments, the polynucleotide is a primer. In some embodiments, the primer is labeled with a detectable moiety. In some embodiments, a primer is not labeled. A primer, as used herein, is a polynucleotide that is capable of specifically hybridizing to a target gene or to an amplicon that has been amplified from a target gene (collectively referred to as "template"), and, in the presence of the template, a polymerase and suitable buffers and reagents, can be extended to form a primer extension product.

In some embodiments, the polynucleotide is a probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In some embodiments, a probe is extendable.

In some embodiments, the polynucleotide is a FRET probe that in some embodiments is labeled at the 5'-end with a fluorescent dye (donor) and at the 3'-end with a quencher (acceptor), a chemical group that absorbs (i.e., suppresses) fluorescence emission from the dye when the groups are in close proximity (i.e., attached to the same probe). In some embodiments, the dye and quencher are not at the ends of the FRET probe. Thus, in some embodiments, the emission spectrum of the dye should overlap considerably with the absorption spectrum of the quencher.

7.2.6.1. Exemplary Polynucleotide Modifications

In some embodiments, the methods of detecting at least one target DNA described herein employ one or more polynucleotides that have been modified, such as polynucleotides comprising one or more affinity-enhancing nucleotide analogs. Modified polynucleotides useful in the methods described herein include primers for reverse transcription, PCR amplification primers, and probes. In some embodiments, the incorporation of affinity-enhancing nucleotides increases the binding affinity and specificity of a polynucleotide for its target nucleic acid as compared to polynucleotides that contain only deoxyribonucleotides, and allows for the use of shorter polynucleotides or for shorter regions of complementarity between the polynucleotide and the target nucleic acid.

In some embodiments, affinity-enhancing nucleotide analogs include nucleotides comprising one or more base modifications, sugar modifications and/or backbone modifications.

In some embodiments, modified bases for use in affinity-enhancing nucleotide analogs include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing nucleotide analogs include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing nucleotide analogs include backbone modifications such as the use of peptide nucleic acids (PNA; e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, a polynucleotide includes at least one affinity-enhancing nucleotide analog that has a modified base, at least nucleotide (which may be the same nucleotide) that has a modified sugar, and/or at least one internucleotide linkage that is non-naturally occurring.

In some embodiments, an affinity-enhancing nucleotide analog contains a locked nucleic acid ("LNA") sugar, which is a bicyclic sugar. In some embodiments, a polynucleotide for use in the methods described herein comprises one or more nucleotides having an LNA sugar. In some embodiments, a polynucleotide contains one or more regions consisting of nucleotides with LNA sugars. In some embodiments, a polynucleotide contains nucleotides with LNA sugars interspersed with deoxyribonucleotides. See, e.g., Frieden, M. et al. (2008) Curr. Pharm. Des. 14(11):1138-1142.

7.2.6.2. Exemplary Primers

In some embodiments, a primer is provided. In some embodiments, a primer is identical to, or complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a sequence selected from NG2, NG4, CT1, or CT2 or from a target gene that indicates genomic copy number, such as e.g., HMBS, GAPDH, beta-actin, and beta-globin. In some embodiments, a primer is provided that comprises a region that is identical to, or complementary to, a span of 6 to 100, 8 to 100, 8 to 75, 8 to 50, 8 to 40, or 8 to 30 contiguous nucleotides of a sequence selected from NG2, NG4, CT1, and CT2 or form a target gene that indicates genomic copy number, such as e.g., HMBS, GAPDH, beta-actin, and beta-globin. Non-limiting exemplary primers are shown in Table 2. In some embodiments, a primer may also comprise portions or regions that are not identical or complementary to the target gene. In some embodiments, a region of a primer that is identical or complementary to a target gene is contiguous, such that any region of a primer that is not identical or complementary to the target gene does not disrupt the identical or complementary region.

As used herein, "selectively hybridize" means that a polynucleotide, such as a primer or probe, will hybridize to a particular nucleic acid in a sample with at least 5-fold greater affinity than it will hybridize to another nucleic acid present in the same sample that has a different nucleotide sequence in the hybridizing region. Exemplary hybridization conditions are discussed herein, for example, in the context of a reverse transcription reaction or a PCR amplification reaction. In some embodiments, a polynucleotide will hybridize to a particular nucleic acid in a sample with at least 10-fold greater affinity than it will hybridize to another nucleic acid present in the same sample that has a different nucleotide sequence in the hybridizing region.

In some embodiments, a primer is used to amplify a target DNA. In some embodiments, amplification is quantitative PCR, for example, as discussed herein. In some embodiments, a primer comprises a detectable moiety.

In some embodiments, primer pairs are provided. Such primer pairs are designed to amplify a portion of a target gene, such as NG2, NG4, CT1, or CT2; an endogenous control DNA; or an exogenous control DNA; or a target gene that indicates genomic copy number, such as e.g., HMBS, GAPDH, beta-actin, and beta-globin. In some embodiments, a primer pair is designed to produce an amplicon that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, or 50 to 100 nucleotides long. Non-limiting exemplary primer pairs are shown in Table 2.

7.2.6.3. Exemplary Probes

In some embodiments, methods of detecting the presence of CT and NG or methods of screening a mammal for infection or inflammation of the urogenital tract comprise hybridizing nucleic acids of, or derived from, a sample with a probe. In some embodiments, the probe comprises a portion that is complementary to a target gene, such as NG2, NG4, CT1, or CT2, or a target gene that indicates genomic copy number, such as e.g., HMBS, GAPDH, beta-actin, and beta-globin. In some embodiments, the probe comprises a portion that is identically present in the target gene. In some some embodiments, a probe that is complementary to a target gene is complementary to a sufficient portion of the target gene such that it selectively hybridizes to the target gene under the conditions of the particular assay being used. In some embodiments, a probe that is complementary to a target gene comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the target gene, such as NG2, NG4, CT1, or CT2. Non-limiting exemplary probes are shown in Table 2. A probe that is complementary to a target gene may also comprise portions or regions that are not complementary to the target gene. In some embodiments, a region of a probe that is complementary to a target gene is contiguous, such that any region of a probe that is not complementary to the target gene does not disrupt the complementary region.

As described above, in some embodiments, real-time PCR detection may be performed using a FRET probe, which includes, but is not limited to, a TaqMan® probe, a Molecular beacon probe and a Scorpion probe. In some embodiments, the real-time RT-PCR detection and quantification is performed with a TaqMan® probe, i.e., a linear probe that typically has a fluorescent dye covalently bound at one end of the DNA and a quencher molecule covalently bound at the other end of the DNA. The FRET probe comprises a sequence that is complementary to a region of the target gene such that, when the FRET probe is hybridized to the target gene or an amplicon of the target gene, the dye fluorescence is quenched, and when the probe is digested during amplification of the target gene or amplicon of the target gene, the dye is released from the probe and produces a fluorescence signal. In some embodiments, the presence of the target gene in the sample is detected.

The TaqMan® probe typically comprises a region of contiguous nucleotides having a sequence that is identically present in or complementary to a region of a target gene such that the probe is specifically hybridizable to the resulting PCR amplicon. In some embodiments, the probe comprises a region of at least 6 contiguous nucleotides having a sequence that is fully complementary to or identically present in a region of a target gene, such as comprising a region of at least 8 contiguous nucleotides, at least 10 contiguous nucleotides, at least 12 contiguous nucleotides, at least 14 contiguous nucleotides, or at least 16 contiguous nucleotides having a sequence that is complementary to or identically present in a region of a target gene to be detected.

In some embodiments, the region of the DNA amplicon that has a sequence that is complementary to the TaqMan0 probe sequence is at or near the center of the DNA amplicon. In some embodiments, there are independently at least 2 nucleotides, such as at least 3 nucleotides, such as at least 4 nucleotides, such as at least 5 nucleotides of the DNA amplicon at the 5'-end and at the 3'-end of the region of complementarity.

In some embodiments, Molecular Beacons can be used to detect and quantitate PCR products. Like TaqMan® probes, Molecular Beacons use FRET to detect and quantitate a PCR product via a probe having a fluorescent dye and a quencher attached at the ends of the probe. Unlike TaqMan® probes, Molecular Beacons remain intact during the PCR cycles. Molecular Beacon probes form a stem-loop structure when free in solution, thereby allowing the dye and quencher to be in close enough proximity to cause fluorescence quenching. When the Molecular Beacon hybridizes to a target, the stem-loop structure is abolished so that the dye and the quencher become separated in space and the dye fluoresces. Molecular Beacons are available, e.g., from Gene Link™ (see www.genelink.com/newsite/products/mbintro.asp).

In some embodiments, Scorpion probes can be used as both sequence-specific primers and for PCR product detection and quantitation. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent dye molecule is attached to the 5'-end of the Scorpion probe, and a quencher is attached to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the dye on the 5'-end to fluoresce and generate a signal. Scorpion probes are available from, e.g, Premier Biosoft International (see www.premierbiosoft.com/tech_notes/Scorpion.html).

In some embodiments, labels that can be used on the FRET probes include colorimetric and fluorescent dyes such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Examples of dye/quencher pairs (i.e., donor/acceptor pairs) include, but are not limited to, fluorescein/tetramethylrhodamine; IAEDANS/fluorescein; EDANS/dabcyl; fluorescein/fluorescein; BODIPY FL/BODIPY FL; fluorescein/QSY 7 or QSY 9 dyes. When the donor and acceptor are the same, FRET may be detected, in some embodiments, by fluorescence depolarization. Certain specific examples of dye/quencher pairs (i.e., donor/acceptor pairs) include, but are not limited to, Alexa Fluor 350/Alexa Fluor488; Alexa Fluor 488/Alexa Fluor 546; Alexa Fluor 488/Alexa Fluor 555; Alexa Fluor 488/Alexa Fluor 568; Alexa Fluor 488/ Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/ Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY9; Alexa Fluor 568/QSY 7 or QSY 9; Alexa Fluor 568/QSY 21; Alexa Fluor 594/QSY 21; and Alexa Fluor 647/QSY 21. In some embodiments, the same quencher may be used for multiple dyes, for example, a broad spectrum quencher, such as an Iowa Black® quencher (Integrated DNA Technologies, Coralville, Iowa) or a Black Hole Quencher™ (BHQ™; Sigma-Aldrich, St. Louis, Mo.).

In some embodiments, for example, in a multiplex reaction in which two or more moieties (such as amplicons) are detected simultaneously, each probe comprises a detectably different dye such that the dyes may be distinguished when detected simultaneously in the same reaction. One skilled in the art can select a set of detectably different dyes for use in a multiplex reaction.

Specific examples of fluorescently labeled ribonucleotides useful in the preparation of real-time PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of real-time PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, dyes and other moieties, such as quenchers, are introduced into polynucleotide used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In some embodiments, the modified nucleotide includes one or more reactive groups that can react with a dye or quencher before, during, or after incorporation of the modified nucleotide into the nucleic acid. In some embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In some embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

Exemplary detectable moieties also include, but are not limited to, members of binding pairs. In some some embodiments, a first member of a binding pair is linked to a polynucleotide. The second member of the binding pair is linked to a detectable label, such as a fluorescent label. When the polynucleotide linked to the first member of the binding pair is incubated with the second member of the binding pair linked to the detectable label, the first and second members of the binding pair associate and the polynucleotide can be detected. Exemplary binding pairs include, but are not limited to, biotin and streptavidin, antibodies and antigens, etc.

In some embodiments, multiple target genes are detected in a single multiplex reaction. In some some embodiments, each probe that is targeted to a different gene is spectrally distinguishable when released from the probe. Thus, each target gene is detected by a unique fluorescence signal.

One skilled in the art can select a suitable detection method for a selected assay, e.g., a real-time PCR assay. The selected detection method need not be a method described above, and may be any method.

7.3. Exemplary Compositions and Kits

In another aspect, compositions are provided. In some embodiments, compositions are provided for use in the methods described herein.

7.3.1. Compositions and Kits for Detecting CT and NG

In some embodiments, compositions are provided that comprise at least one target gene-specific primer. The term "target gene-specific primer" encompasses primers that have a region of contiguous nucleotides having a sequence that is (i) identically present in a target gene, such as NG2, NG4, CT1, or CT2, or (ii) complementary to the sequence of a region of contiguous nucleotides found in a target gene, such as NG2, NG4, CT1, or CT2. In some embodiments, a composition is provided that comprises at least one pair of target gene-specific primers. The term "pair of target gene-specific primers" encompasses pairs of primers that are suitable for amplifying a defined region of a target gene, such as NG2, NG4, CT1, or CT2. A pair of target gene-specific primers typically comprises a first primer that comprises a sequence that is identical to the sequence of a region of a target gene and a second primer that comprises a sequence that is complementary to a region of a target gene (i.e., is identical to the complementary strand of the target gene). A pair of primers is typically suitable for amplifying a region of a target gene that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, or 50 to 100 nucleotides long. Non-limiting exemplary primers, and pairs of primers, are shown in Table 2.

In some embodiments, a composition comprises three pairs of target gene-specific primers, one pair for amplifying each of NG2, NG4, and CT1. In some embodiments, a composition comprises three pairs of target gene-specific primers, one pair for amplifying each of NG2, NG4, and CT2. In some embodiments, a composition additionally comprises a pair of target-specific primers for amplifying an endogenous control DNA and/or one pair of target-specific primers for amplifying an exogenous control DNA.

In some embodiments, a composition comprises at least one target gene-specific probe. The term "target gene-specific probe" encompasses probes that have a region of contiguous nucleotides having a sequence that is (i) identically present in a target gene, such as such as NG2, NG4, CT1, or CT2, or (ii) complementary to the sequence of a region of contiguous nucleotides found in a target gene, such as such as NG2, NG4, CT1, or CT2. Non-limiting exemplary target-specific probes are shown in Table 2.

In some embodiments, a composition comprises three pairs of target gene-specific primers, one pair for amplifying each of NG2, NG4, and CT1. In some embodiments, a composition comprises three pairs of target gene-specific primers, one pair for amplifying each of NG2, NG4, and CT2. In some embodiments, a composition additionally comprises a probe for detecting an endogenous control DNA and/or a probe for detecting an exogenous control DNA.

In some embodiments, a composition is an aqueous composition. In some embodiments, the aqueous composition comprises a buffering component, such as phosphate, tris, HEPES, etc., and/or additional components, as discussed below. In some embodiments, a composition is dry, for example, lyophilized, and suitable for reconstitution by addition of fluid. A dry composition may include one or more buffering components and/or additional components.

In some embodiments, a composition further comprises one or more additional components. Additional components include, but are not limited to, salts, such as NaCl, KCl, and MgCl$_2$; polymerases, including thermostable polymerases such as Taq; dNTPs; bovine serum albumin (BSA) and the like; reducing agents, such as β-mercaptoethanol; EDTA and the like; etc. One skilled in the art can select suitable composition components depending on the intended use of the composition.

In some embodiments, compositions are provided that comprise at least one polynucleotide for detecting at least one target gene. In some embodiments, the polynucleotide is used as a primer for amplification. In some embodiments, the polynucleotide is used as a primer for real-time PCR. In some embodiments, the polynucleotide is used as a probe for detecting at least one target gene. In some embodiments, the polynucleotide is detectably labeled. In some embodiments, the polynucleotide is a FRET probe. In some embodiments, the polynucleotide is a TaqMan® probe, a Molecular Beacon, or a Scorpion probe.

In some embodiments, a composition comprises at least one FRET probe having a sequence that is identically present in, or complementary to a region of, NG2, NG4, CT1, or CT2. In some embodiments, a FRET probe is labeled with a donor/acceptor pair such that when the probe is digested during the PCR reaction, it produces a unique fluorescence emission that is associated with a specific target gene or a target gene amplicon. In some embodiments, when a composition comprises multiple FRET probes, each probe is labeled with a different donor/acceptor pair such that when the probe is digested during the PCR reaction, each one produces a unique fluorescence emission that is associated with a specific probe sequence and/or target gene. In some embodiments, the sequence of the FRET probe is complementary to a target region of a target gene. In some embodiments, the FRET probe has a sequence that comprises one or more base mismatches when compared to the sequence of the best-aligned target region of a target gene.

In some embodiments, a composition comprises a FRET probe consisting of at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides, wherein at least a portion of the sequence is identically present in, or complementary to a region of, NG2, NG4, CT1, or CT2. In some embodiments, at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides of the FRET probe are identically present in, or complementary to a region of, NG2, NG4, CT1, or CT2. In some embodiments, the FRET probe has a sequence with one, two or three base mismatches when compared to the sequence or complement of NG2, NG4, CT1, or CT2.

In some embodiments, a kit comprises a polynucleotide discussed above. In some embodiments, a kit comprises at least one primer and/or probe discussed above. In some embodiments, a kit comprises at least one polymerase, such as a thermostable polymerase. In some embodiments, a kit comprises dNTPs. In some embodiments, kits for use in the real-time PCR methods described herein comprise one or more target gene-specific FRET probes and/or one or more primers for amplification of target genes.

In some embodiments, one or more of the primers and/or probes is "linear". A "linear" primer refers to a polynucleotide that is a single stranded molecule, and typically does not comprise a short region of, for example, at least 3, 4 or 5 contiguous nucleotides, which are complementary to another region within the same polynucleotide such that the primer forms an internal duplex. In some embodiments, the primers for use in reverse transcription comprise a region of at least 4, such as at least 5, such as at least 6, such as at least 7 or more contiguous nucleotides at the 3'-end that has a sequence that is complementary to region of at least 4, such as at least 5, such as at least 6, such as at least 7 or more contiguous nucleotides at the 5'-end of a target gene.

In some embodiments, a kit comprises one or more pairs of linear primers (a "forward primer" and a "reverse primer") for amplification of a target gene, such as NG2, NG4, CT1, or CT2. Accordingly, in some embodiments, a first primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is identical to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a first location in the gene. Furthermore, in some embodiments, a second primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is complementary to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a second location in the gene, such that a PCR reaction using the two primers results in an amplicon extending from the first location of the target gene to the second location of the target gene.

In some embodiments, the kit comprises at least two, at least three, or at least four sets of primers, each of which is for amplification of a different target gene, such as NG2, NG4, CT1, or CT2. In some embodiments, the kit further comprises at least one set of primers for amplifying a control DNA, such as an endogenous control and/or an exogenous control.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the kits for use in real-time PCR methods described herein further comprise reagents for use in the amplification reactions. In some embodiments, the kits comprise enzymes such as heat stable DNA polymerase, such as Taq polymerase. In some embodiments, the kits further comprise deoxyribonucleotide triphosphates (dNTP) for use in amplification. In some embodiments, the kits comprise buffers optimized for specific hybridization of the probes and primers.

7.3.2. Kits for Screening a Mammal for Infection or Inflammation of the Urogenital Tract The invention also provides a kit for screening a mammal for infection or inflammation of the urogenital tract. Such kits include one or more reagents useful for practicing any of the screening methods described herein. A kit generally includes a package with one or more containers holding the reagents, as one or more separate compositions or, optionally, as an admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits preferably include instructions for carrying out one or more of the screening methods described herein. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

In some embodiments, a kit for performing a method of screening for elevated genomic copy number and a pathogen includes at least one primer and/or probe for detecting or sequencing an indicator of genomic copy number and at least one primer and/or probe for detecting or sequencing a nucleic acid sequence that is indicative of a pathogen that infects the urogenital tract and/or a miRNA correlated with inflammation. In variations of these embodiments, the indicator of genomic copy number includes at least one nucleic acid sequence that is expected to be present in the genome of the mammal in one or two copies. Examples of such nucleic acid sequences include, but are not limited to, a hydroxymethylbilane synthase (HMBS), glyceraldehyde 3-phosphate dehydrogenase (GAPDH), beta-actin, and beta-globin nucleic acid sequences. In some embodiments, the kit may include at least one primer and/or a probe for detecting or sequencing each of a plurality of indicators of genomic copy number. Where the pathogen to be detected is *Chlamydia trachomatis* (CT) and *Neisseria gonorrhoeae* (NG), any of the primers and/or probes described here for this purpose can be included in the kit. Other primers and probes for detecting or sequencing other pathogens that infect the urogenital tract are known, or can readily be designed, and can be included in the kit. Similarly, primers and probes for detecting or sequencing miRNAs correlated with inflammation, including those described herein, are known, or can readily be designed, and can be included in the kit.

In some embodiments that are useful for human screening, the indicator of genomic copy number is a human HBMS sequence, and the kit includes one or more of primers including SEQ ID NO:113 and SEQ ID NO:114, which are useful for amplifying HBMS. In some embodiments, the kit can include a probe including SEQ ID NO:115. This probe is useful for detecting the human HBMS sequence that is amplified, e.g., using primers including SEQ ID NO:113 and SEQ ID NO:114. The probe can be labeled to facilitate detection, e.g., in a real-time PCR reaction. In some embodiments, the probe is a Taqman® probe.

In some embodiments, the kit can comprise the reagents described above provided in one or more GeneXpert® Sample cartridge(s). These cartridges permit extraction, amplification, and detection to be be carried out within this self-contained "laboratory in a cartridge." (See e.g., U.S.

Pat. Nos. 5,958,349, 6,403,037, 6,440,725, 6,783,736, 6,818,185; each of which is herein incorporated by reference in its entirety.) Reagents for measuring genomic copy number level and detecting a pathogen could be provided in separate cartridges within a kit or these reagents (adapted for multiplex detection) could be provide in a single cartridge.

In some embodiments, which are useful, e.g., for assaying for a plurality of indicators of genomic copy number, the kit can include probes immobilized on a substrate, e.g., a DNA array.

Any of the kits described here can include, in some embodiments, a receptacle for a urine sample or a swab for collecting a urethral swab sample, a vaginal swab sample, or an endocervical swab sample.

The following examples are for illustration purposes only, and are not meant to be limiting in any way.

8. EXAMPLES

8.1. Example 1: CT and NG Target Genes, and Probes and Primers for Detecting the Target Genes Candidate NG target regions were selected and confirmed to be present in about 125 different commercially available strains of *Neisseria gonorrhoeae* and candidate CT target regions were selected and confirmed to be present in 14 commercially available serovars of *Chlamydia trachomatis*. The 12 target genes selected for development of a specific and sensitive CT/NG diagnostic test are shown in Table 1.

TABLE 1

CT/NG target genes

| Target | Length | Sequence | SEQ ID NO |
|---|---|---|---|
| NG1 | 600 bp | AGTGTCCATT CTTTTCGGGC AGTCTGAATC CGTCTGGCTG ATTAAGGGTA AAACTTATTC AAATCGGCAA CCAATTTGGT TAACTCTTCC TGATTCGGCT TATTCATGCC CCGGTAAACT TTGACGTAGC CTTTGTCGTT TTTCATATTC ACGACATAGA TGACGAAACG TGTGCCGTTG AATCCTTTTT CCGCATCGCA GGTGTAGTAC GTCACACCCC CGCTTTCCGC TTTTTCCAGT ACGCAGTCGT TTTTGCGGTA ACCTTGCTCC TTCGCTATCC AATCCCGCGC AAATGAAGCC CTGTACGCGT CCGGCACGCG GACTTGGTCG ACCAATAAAT CATGATCGGG ATTTTGGGAA TAACCGTAAT GGAAAACGGC GTTTGAACCG TTCAATTGCG CCTCCGGCAT TTGATAACGC CGGTTTTGGA AAAACGCATC GTTCGGGTTC ATGCAGGCAG TTAAAAGAAA AGTCAGGAGT GCGGCTGTGT ATTTCATAGT TTGTTCACTC GGGCGGTTAA AGGAAAAGTC AGGAATACGG TTGTGTATTT TATGGTTTAT TCTCTTATAA ACAGTTATAA ACGGTTTCAA GGCGGCTTGC | 1 |
| NG2 | 400 bp | TCAAGCAAAA TCTCCAAAAC CCGAACAGGC TATGGGTTTT TTGCCAAAAT GATTTTTGCA AGCCGTTGGC TGCAAGTGCC GATTTATGCG GGGCTGACTG TTGTACGGGC GATTTGTGCC TATAAGTTTT TGAAATCGTT GAAGCATCTG GTCATGAATT TGGATGTGTC GGACGAAAAC GCCATCATGC TCGCTGTTTT AAATCTGATT GATGTGGTTA TGATTGCGAA TTTGCTGACC ATGGTGCAGA TTGGCGGGTA TGAGTCGTTC GTATCCCGGT TGCGTATCGA CGACCATCCT GACCGGCCCG AGTGGTTGAG CCATGTGAAT GCACCGGTAT TGAAGGTAAG GCTGTCGATG TCGATTATCG GTATTCATCC ATCCATTTGC TCCAAACATT | 2 |
| NG3 | 200 bp | AGTGCGTCGG GTTTGCGCAA TACCTCAACT TCAACCTCGG CAACGCCTTC AAATACATCT GGCGGCACAA GGAAAAAGGC GGGCGCGAAG ACTTGGAAAA AGCCCTGCGG TACTTGGAAC GCCAACGCGC CGGCGCGCCG AAGTTCAAGA AACTCAAACA CCGCCGCTAT GAAAAAATGT ACGCCGGTCT GAAAGATTGC | 3 |
| NG4 | 778 bp | TGCTGGTGTT TCTTGCCGTC GGCATGCTGG CGGGCGAGGA AGGCGTTGGC GGCATTGCCT TCAATAATGT CGTGATGGCG AATTTCATCA GCCAGCTTGC TTTGGCGGTT ATTCTGCTCG ACGGCGGTTT GCGGACGCAG CTTTCCAGTT TTCGGATTGC GTTGAAGCCC GCGTCGGTAC TCGCTTCGTG GGGCGTGTTT GCCACTGTGC TTCCGCTGGG ACTGTTTGCA ACTTTTTATC TCGGTTTGGA TTGGAAGTTC GGCGTGCTGA TGGCGGCGAT TGTCGGTTCG ACCGATGCCG GCGCGGTATT CAGCCTTTTG CGCAACAGCG GCGTGCGTTT GAACGAACGG GTGCAGGCGA CTTTGGAAAT CGAATCGGGT GCGAACGACC CGATGGCGGT TTTTTTGGTT ACGGCACTGA TTACCATGAT TATGCAGCCG GCGGAATCGG GTGCGGCAGC GTTTGTCCGG ATGCTTGCGC TGCAAATCGG TTTCGGTCTG CTGACGGGTT GGGCGGGCGG AAAGATATTG GCAAAGCTGG TACGCCGTCT GAATCTTGCG GAAGGTCGT ACGCGCTGAT GATTGTGTCG GGCGGGCTGC TTGTGTTTGC GTTTACCAAT ACCATAGGCG GCAGCGGCTT TTTGGCGGTT TACCTTGCCG GCATCATTGT CGGTAACCAG CGCAACCGTG CGACGGAACA CGTTTTGCGT GTGATGGACG GTTTGGCTTG GCTGGCGCAG GCAACTTTGT TCGTCATGCT CGGTCTGCTG GTTTCTCC | 4 |
| NG5 | 492 bp | CCTGCATCTA AACCACATTT TAATATAAGA GACTCCAATT TAGATACAGG ACATGTCGAT GGTACTCACG GACACTATAA TTTTTAGTAA GAAATATGAA TATAATAGAA ATAATAAGTA GGAATCGTTT TCTAAAACAA ATATATCCTA GTGGCATAAT GGATATTTCA CTAGTCTCTT TTTCAACTGA CTTGTCTAAT TGTATTTTAA CTATCCGAAC AAGTACAAAG CCTTCTGTAG AAATCGAAAA ATGGGGCTG TGGCTAAAAG ATTATGATAC AGTTGA7ATT GAATTAAGAA ATAGCTTTAT TAAAGGAATG AAATGTCAAA ATTGGTCGCA TAACAATAGA AATATATGCC AAGTAGAAAT AAAGAACCAA GAAGATGGTC TAAAAATAAT AAGATTTTAC GACAATAATT CAAATTGGTT ATTGGAACTA GAAGTTTATG GATTAGTTTT CCAAGGGTGT AAGACTTATA TGAAAGAGGG TT | 5 |

TABLE 1-continued

CT/NG target genes

| Target | Length | Sequence | SEQ ID NO |
|---|---|---|---|
| NG6 | 750 bp | TCAAAGAAAT GTTGGATATG TTGGCAGAAG GTGGCACAGG CATTGCCATT ATTCCAGTCA GTTGCGTGAT TGCACCAAGC AAAGCCAAAA GCGAAATTGT GAAATATCAT CGCTTAAAAG CCGTGATGTC TATGCCGAGC GAACTGTTTT ACCCAGTTGG CACGGTAACG TGCATTGTCG TATTTGAAGC CCATAAACCG CATTTTCAGA CAGTCGTGAT TGACCCGGAC ACACAAGAAG AAATCAGCAC GAAAAAAGCC TGTCGCAAAA CGTGGTTTGG CTACTGGCGT GATGACGGTT TTGAAAAAAC CAAACACTTG GGACGCATTG ATTTATACGA CCGCTGGCAG GGCATTAAAG CGCGCTGGTT GGAACATTAT TTAAACAACG AAGTTCACAC AGGAGAATCG GTAACGCAT TTGTAACTGA TAACGATGAA TGGGTTGCCG AAGCCTATTT GGAAACTGAT TATTCCAAAA TTACCCGAGC AGATTTTGAG CAAGTCGTGC GTGAATTTGC TTTATTTCAA CTACTGGGAG CGGAAGTAGG GCCGACTGAA AATTTGGATA ATGAAAGCTA TGAAGACGAT GACAATAACG ACTTCGGAGA CGATGAATAA TGGTTGAATT GCAAGAGATT TTTGATGTGA GTTACGGTTC AAAATTAGAT TTGAATAAAA TGAGCAGCTT CAATCCAACA ATCAACTTTG TAGGCAGGTC AGGCAAAAAT AATGGTGTAA CAGCATCTGT | 6 |
| CT1 | 450 bp | TTGTAGAGAG GCAAACACCT CAACGCCTGT TAGTATATGC TCTTTGGTGT GAGAGTTTAG GACTGCCGAA CTGCTTTCCT TAGTTTTAAT TCCATCTTTT CGCAAAGGTA GATCCGATAT CAGCAAAAGT GCTCCTAAAG AAGATTCCT TCGGTATCCT GCAGCAAATA AGGTGGCACA CTCCATCTCG ACAGTTTGAG CTTTATTTTC ATATAGTTTT CGACGGAACT CTTTATTAAA CTCCCAAAAC CGAATGTTAG TCGTGTGGGT GATGCCTATA TGGTAAGGGA GGTTTTTGGC TTCGAGAATA TTGGTGATCA TTTTTTGTAC GACAAAATTA GCTAATGCAG GGACCTCTGG GGGGAAGTAT GCATCTGATG TTCCATCTTT TCGGATGCTA GCAACAGGGA CAAAATAATC TCCTATTTGG TAGTGGGATC TTAAGCCTCC | 7 |
| CT2 | 480 bp | TTAAGACAGG GGTTTATTTA ATTGGTTAAC TGTGCTTCCC ACGGAGTTCA ATGTTTTGAT GAAGGAGGAG TTCTGTTGAG CGATTTGCTG CATAATGTTG ATGTTTGTAG ATGCGTGAGA GAGGATAATC TGTCCATTTT GTCGGGCAGT TACTAATTGG TCTTGGATAT TTGAGCGTTG TGCAGAATAG TTTTGGTTCT GGTTTTGTAC TCGTGTGATT TCGTCTTCTT TAGCTCCAGA GCCAACGACA GCGTATTTGA TTTGATTCGT TTCTTGGTTT AATTGCTGTT GGATATTAGT ATTGTCGTTT AGCTGCTTAG ATTGCGTGAG AATCGTCTCT TGACGTATTT CTACAGCTTC TAAAAGAAGA GAGTAAATGC TGAACAAGAG TTCTGCTATT GGAGGCGTTC CCAAAGGCTC TAAAGGAGGT AGCGAGGAGA CGTATTGTGT GTCTCCTACC TGTGAGGTTG CTGCTGACAT | 8 |
| CT3 | 939 bp | TTACTGCTGT TCTGCTGATG TGGAAGCATT CTCTTCGTCT TGAGTAGAAG AAGAGGTTTG CTTAGGGTCT GTTATGGATT TTTTTCTCTT CTCATGTAAC TGAATCAGCT CTTTAGTCAT CAATCTACTG TTTGTTTCTA TATATGCCCA AATCTCGTTA TAGCATTCGA GTTGTGTCTC TGTAAGCGGA TTGATAATCA AGAACTCTTC CAGATTTAAT GTAAGACCTC CTCTACTCCA GTTGACGGAT CCTATAATGA GTGTCGAGCT ATTAATACAG CAGACTTTGG TATGCAGAAT GCCTTCGCAT GTACGTTCTC GTAGGACAAT GCCGTTAGCC TCGAGGATAG CTTTGACGCA CAAGTCTCTT CGTATTTGAC TTAGCGAATA GTAGGATACT TGTTGCGAGC CTACTCGCAC CTCCTCGA TCGTGTCGGA AAGCCCAGCG ATATAGGTGT TCACTAAATA TTTTAGCCGT TAAGTTCACA TCTTTTTCAA GAGAGGCCTC TGTATAGTTT GCTGTTCCCG TAACGACAAT ATTATTGTCT ATAAGAAGGG TTTTTCTATG TAAAAGAAA CACCCTCTTC GAGGTCTAAA CTGCACATTT CCTTCAGTAC AGTGTTTTGA AAAAGGCCCC ATTTGATAGT GTACGGAGAC AGGCGCTCTA TTAGAAGCCT CAGCTAAGGC TGCAAGAATT CTGGGGGATC CGATATTA7A TACTTTTAAT AGAACGCTGC GCTTAGCTTG TAGAATTGTT TCACAAATCA TTTTCACAGG TTCGTTATTT CTTTGCTGAT GAGCAGAGTA GAGTTGGATC AGTTCGTGAT GCTGTAAGAG TCTAGGTACG ACTTGGCTCG AAGAAGATCG GGCTCGTTTA GAGGAGGAAG AAGAAGTGTC TTCGGGAGTC TTGTGTTTTC TCTTGGAGCC GGCGAGCAT | 9 |
| CT4 | 528 bp | ATGTTTGTGT CGTTCGATAA ATCCCGTTGC AGAGCGGATG TCCCCGATTT TTTTGAAAGG ACAGGAAACT TTCTTCTCCA TTGTGTGGCA AGAGGGATCA ATGTTTTATA TCGTGTGAAA CAAATCCCTA ACTATCCTTC ATGCTATTTC TCACATAAAG AGATTTCGTG TTGTCGTCGT ATTGCAAACA TTGTGATCTG TATTCTCACA GGGCCTCTGA TGTTATTGGC CACTGTGTTA GGATTATTAG CGTATAGGTT TCTTCTACT TACCAGACTT CTTTACAAGA ACGCTTTCGT TATAAATATG AACAAAAGCA AGCTTTAGAT GAATACCGTG ATAGGGAAGA AAAAGTCATT ACGCTTCAGA AGTTTTGTAG AGGATTTCTA GTTAGAAATC ATTTGCTCAA CCAAGAAACT TTAACAACGT GTAAGCAATG GGGGCAAAAA CTATTAGAAG GAGAAAAATT CCAAGGGTCC CAGAAGGACG GTCTCTTGTA TATATTTCAA AACAGTTTTC TTCTTTAG | 10 |
| CT5 | 902 bp | GAGGGGAGAA TTCTAAGAAA AGAAAATAAT GTAGCATATA TTTATGAAAT GTTGTAATAT TATAGCATTA CAAAAAGGTG CGATATGAAA AATCAAGAGG AGTCTGGCTG GCAAGCTTTT CTGACATTAT GCTCTAAAAT GCAAAAAGAA AAGTTTTTAC AAGACCTTTT TTCGCTGTTT TTGTCTTTA GCGAACGTAA AGATGTCGCT TCTCGCTATC ATATCATTCG AGCTCTTTTA GAAGGGGAGC | 11 |

TABLE 1-continued

CT/NG target genes

| Target | Length | Sequence | SEQ ID NO |
|---|---|---|---|
| | | TCACTCAAAG AGAGATAGCA GAGAAATACG GAGTCAGTAT CGCACAAATT ACCAGAGGAT CTAATGCCCT TAAAGGATTA GATCCTCAAT TTAAAGAGTT TTTACAAAAA GAGATCTGAT CTTCTTTTGT AAAATACAAA TAAGATTAAA AGTATTTGTA TGCATGCGTT GTTAATGAAC AAATATTCTG TTTTAGCAGT TTTGGTACAT AAGTATAGCT GCAGCATGCC ATGCAAATCA GCTTTTCAAG CTGATTGCTT CCAAGATATT CAAAAATTCA TCCTCTTACA GCGTGCCTGG CTTTCTTTTG AAAGCTGGCG CTTATCTACT TGGCGATAGG CCTAATTAAG AAGCCTTTTA TTTGATTAAG AGATGTTCTT ATAGAAGTAA GAGCGTCTTT TTTGCGCAGG ATTATTCTGT CGCCAGTTTT TTCTATGATT TTAACACTAT AATTTTATGG AGAAAAGATG TTCAAACATA AACATCCTTT TGGGGGAGCG TTCCTTCCCG AAGAACTATT AGCCCCTATA CAGAATCTAA AAGCGGAATG GGAGATTCTC AAAACTCAGC AAAGTTTTTT ATCTGAACTA GATTGTATTT TGAAAAACTA TGCGGGGAGA CAAACTCCTC TGACTGAAGT TAAGAATTTT GC | |
| CT6 | 963 bp | GCGTTACGAG CTTTTTTCCT GCTTACTAGA AACGAGGGGA TTATTCCTGC ATTGGAGTCT TCACATGCTC TCGCACATTT AGTTTCGATT GCTCCTTCTC TACCAAAGGA ACAAATCGTC ATCGTTAACT TATCTGGAAG AAGTGATAAG GATCTTTCAC AAATCATCCG CAGAAACAGA GGAATTTATG AGTAAATTAA CCCAAGTTTT TAAACAAACT AAGCCATGTA TTGGCTATCT AACCGCTGGT GATGGCGGTA CTAGTTATAC TATTGAGGCG GCAAAAGCTC TGATTCAAGG AGGTGTCGAT ATTCTGGAAC TAGGATTTCC TTTTTCTGAT CCTGTTGCAG ATAATCCAGA AATTCAAGTA TCTCATGATC GGGCTTTAGC AGAAAATCTG ACGTCAGAAA CTTTGTTAGA GATCGTAGAA GGTATCCGAG CTTTTAATCA AGAAGTCCCA TTGATCTTAT ATAGCTACTA CAATCCGCTT CTACAAAGGG ACTTAGATTA TCTACGCAGA CTAAAAGACG CGGGAATAAA TGGTGTGTGC GTTATAGATC TTCCAGCACC TTTATCACAC GGAGAAAAAT CTCCTTTTGA AGATCTTTTA GCTGTAGGAT TGGATCCTAT TTTGCTTATT TCTGCAGGGA CAACGCCGGA GCGGATGTCT TTAATACAAG AACACGCAAG AGGCCTTCTG TATTATATCC CATACAAGCT ACGAGAGATT CTGAAGTAGG TATCAAAGAA GAATTTCGAA AAGTCAGAGA ACATTTTGAT CTTCCAATTG TAGATAGAAG AGATATTTGT GATAAAAAAG AAGCTGCACA TGTGCTGAAT TATTCAGATG GTTTCATTGT GAAAACAGCG TTTGTTCATC AGACAACAAT GGATTCTTCG GTAGAGACTC TGACTGCACT TGCACAAACA GTTATTCCTG GATAATTTAT GAATATGAAG CCC | 12 |

Table 2 shows the sequences of exemplary primers and probes that may be used to detect each of the target genes in a real-time PCR reaction, and exemplary primers and probes that may be used to detect an endogenous control, HMBS.

TABLE 2

Primer and probe sequences

| Oligo name | Sequence | Amplicon size (region) | SEQ ID NO |
|---|---|---|---|
| NG1a forward | GTCTGAATCCGTCTGGCTGATT | 151 bp (22-172) | 13 |
| NG1a reverse | CACGTTTCGTCATCTATGTCGTGA | | 14 |
| NG1a probe | TCGGCTTATTCATGCCCCGGTAAAC | | 15 |
| NG1b forward | GGCGTTTGAACCGTTCAATTG | 72 bp (378-449) | 16 |
| NG1b reverse | AACCCGAACGATGCGTTTT | | 17 |
| NG1b probe | CCTCCGGCATTTGATAACGCC | | 18 |
| NG2a forward | CGGGCGATTTGTGCCTATAAG | 75 bp (106-180) | 19 |
| NG2a reverse | GTTTTCGTCCGACACATCCAA | | 20 |
| NG2a probe | TTTTGAAATCGTTGAAGCATCTGGTCATGAA | | 21 |
| NG2b forward | CGTTGAAGCATCTGGTCATGAA | (137-211) | 22 |
| NG2b reverse | CAATCAGATTTAAAACAGCGAGCAT | | 23 |

TABLE 2-continued

Primer and probe sequences

| Oligo name | Sequence | Amplicon size (region) | SEQ ID NO |
|---|---|---|---|
| NG2b probe | TGGATGTGTCGGACGAAAACGCCA | | 24 |
| NG2c forward | AATTTGGATGTGTCGGACGAAA | (157-233) | 25 |
| NG2c reverse | AAATTCGCAATCATAACCACATCA | | 26 |
| NG2c probe | CGCCATCATGCTCGCTGTTTTAAATCTGA | | 27 |
| NG2d forward | TGAGTCGTTCGTATCCCGGTT | (261-353) | 28 |
| NG2d reverse | AGCCTTACCTTCAATACCGGTG | | 29 |
| NG2d probe1 | CTGACCGGCCCGAGTGGTTGA | | 30 |
| NG2d probe2 | CGGCCCGAGTGGTTGAGCCA | | 31 |
| NG2e forward | CGATTTGTGCCTATAAGTTTTGAA | | 32 |
| NG2e reverse | GCAATCATAACCACATCAATCAGAT | | 33 |
| NG2e probe | CTGGTCATGAATTTGGATGTGTCGGACG | | 34 |
| NG3 forward | TCTGGCGGCACAAGGAAA | | 35 |
| NG3 reverse | CCAAGTACCGCAGGGCTTTT | | 36 |
| NG3 probe | AGGCGGGCGCGAAGACTTGG | | 37 |
| NG4a forward | GGACGCAGCTTTCCAGTTTTC | | 38 |
| NG4a reverse | CGCCCCACGAAGCGAGTA | | 39 |
| NG4a probe | ATTGCGTTGAAGCCCGCGTCG | | 40 |
| NG4b forward | CAGGCGACTTTGGAAATCGA | | 41 |
| NG4b reverse | CAGTGCCGTAACCAAAAAAACC | | 42 |
| NG4b probe | CGGGTGCGAACGACCCGATG | | 43 |
| NG4c forward | CGCTGCAAATCGGTTTCG | | 44 |
| NG4c reverse | ACCAGCTTTGCCAATATCTTTCC | | 45 |
| NG4c probe | TCTGCTGACGGGTTGGGCGG | | 46 |
| NG4d forward | AAAGCTGGTACGCCGTCTGAA | | 47 |
| NG4d reverse | TGCCGCCTATGGTATTGGTAA | | 48 |
| NG4d probe | TGTCGGGCGGGCTGCTTGTGTTT | | 49 |
| NG5a forward | CGACCAATTTTGACATTTCATTCC | | 50 |
| NG5a reverse | CCGAACAAGTACAAAGCCTTCTGT | | 51 |
| NG5a probe | TCTTTTAGCCACAGCCCCCATT | | 52 |
| NG5b forward | AGAGACTCCAATTTAGATACAGGACATGT | | 53 |
| NG5b reverse | CCATTATGCCACTAGGATATATTTGTTTT | | 54 |
| NG5b probe | ATGGTACTCACGGACACTATA | | 55 |
| NG6a forward | TGGCACAGGCATTGCCATTA | | 56 |
| NG6a reverse | CAATTTCGCTTTTGGCTTTGC | | 57 |
| NG6a probe | TCCAGTCAGTTGCGTGATTGCACCA | | 58 |
| NG6b forward | CCGCTGGCAGGGCATTA | | 59 |
| NG6b reverse | TTACCGATTCTCCTGTGTGAACTTC | | 60 |

TABLE 2-continued

Primer and probe sequences

| Oligo name | Sequence | Amplicon size (region) | SEQ ID NO |
|---|---|---|---|
| NG6b probe | AGCGCGCTGGTTGGAACATTATTTAAACAA | | 61 |
| NG6c forward | TTTTGATGTGAGTTACGGTTCAAAA | | 62 |
| NG6c reverse | TTGCCTGACCTGCCTACAAAG | | 63 |
| NG6c probe | TGAATAAAATGAGCAGCTTCAATCCAACAATCA | | 64 |
| CT1a forward | ACTGCCGAACTGCTTTCCTTAG | | 65 |
| CT1a reverse | GCCACCTTATTTGCTGCAGGAT | | 66 |
| CT1a probe | CGCAAAGGTAGATCCGATATCAGCAAAAGTG | | 67 |
| CT1b forward | CTGCCGAACTGCTTTCCTTAGT | | 68 |
| CT1b reverse | TCAAACTGTCGAGATGGAGTGTG | | 69 |
| CT1b probe | CGCAAAGGTAGATCCGATATCAGCAAAAGTG | | 70 |
| CT1c forward | TTTTCGCAAAGGTAGATCCGATA | | 71 |
| CT1c reverse | GTTCCGTCGAAAACTATATGAAAATAAA | | 72 |
| CT1c probe | TGCAGCAAATAAGGTGGCACACTCCATC | | 73 |
| CT2a forward | GTTAACTGTGCTTCCCACGGAG | | 74 |
| CT2a reverse | AACTATTCTGCACAACGCTCAAAT | | 75 |
| CT2a probe | AGGAGGAGTTCTGTTGAGCGATTTG | | 76 |
| CT2b forward | GGAGGAGTTCTGTTGAGCGATT | | 77 |
| CT2b reverse | GCCCGACAAAATGGACAGATT | | 78 |
| CT2b probe | CTGCATAATGTTGATGTTTGTAGATGCGTG | | 79 |
| CT2c forward | AGGAGGAGTTCTGTTGAGCGATT | | 80 |
| CT2c reverse | GCCCGACAAAATGGACAGATT | | 81 |
| CT2c probe | CTGCATAATGTTGATGTTTGTAGATGCGTG | | 82 |
| CT3a forward | TGACTTAGCGAATAGTAGGATACTTGTTG | | 83 |
| CT3a reverse | ACCTATATCGCTGGGCTTTCC | | 84 |
| CT3a probe | CCTACTCGCACCTCTCCTCGATCGTGT | | 85 |
| CT3b forward | GTCTAGGTACGACTTGGCTCGAA | | 86 |
| CT3b reverse | AACACAAGACTCCCGAAGACACTT | | 87 |
| CT3b probe | AAGATCGGGCTCGTTTAGAGGAGGAAGAA | | 88 |
| CT4a forward | CCGTTGCAGAGCGGATGTC | | 89 |
| CT4a reverse | TGATCCCTCTTGCCACACAA | | 90 |
| CT4a probe | CCGATTTTTTTGAAAGGACAGGAAACTTTCTTCTCC | | 91 |
| CT4b forward | TCTCACAGGGCCTCTGATGTT | | 92 |
| CT4b reverse | CGTTCTTGTAAAGAAGTCTGGTAAGTAGA | | 93 |
| CT4b probe | TTGGCCACTGTGTTAGGATTATTAGCGTATAGGTTT | | 94 |
| CT5a forward | GACCTTTTTTCGCTGTTTTTGTC | | 95 |
| CT5a reverse | CCCCTTCTAAAAGAGCTCGAATG | | 96 |

TABLE 2-continued

Primer and probe sequences

| Oligo name | Sequence | Amplicon size (region) | SEQ ID NO |
|---|---|---|---|
| CT5a probe | CGAACGTAAAGATGTCGCTTCTCGCTATCA | | 97 |
| CT5b forward | GGCCTAATTAAGAAGCCTTTTATTTG | | 98 |
| CT5b reverse | TCATAGAAAAAACTGGCGACAGAA | | 99 |
| CT5b probe | AGAAGTAAGAGCGTCTTTTTTGCGCAGGAT | | 100 |
| CT6a forward | CCTGCATTGGAGTCTTCACATG | | 101 |
| CT6a reverse | CGATGACGATTTGTTCCTTTGG | | 102 |
| CT6a probe | TCTCGCACATTTAGTTTCGATTGCTCCTTCTC | | 103 |
| CT6b forward | CAAAGGGACTTAGATTATCTACGCAGACTA | | 104 |
| CT6b reverse | CCGTGTGATAAAGGTGCTGGAA | | 105 |
| CT6b probe | AAGACGCGGGAATAAATGGTGTGTGCGTT | | 106 |
| CT6c forward | TCCAATTGTAGATAGAAGAGATATTTGTGA | | 107 |
| CT6c reverse | TGTCTGATGAACAAACGCTGTTT | | 108 |
| CT6c probe | ACATGTGCTGAATTATTCAGATGGTTTCATTGTG | | 109 |
| CT6d forward | TCCAATTGTAGATAGAAGAGATATTTGTGA | | 110 |
| CT6d reverse | TGTTTGATGAACAAACGCTGTTT | | 111 |
| CT6d probe | ACATGTGCTGAATTATTCAGATGGTTTCATTGTG | | 112 |
| HMBS forward | AGATTCTTGATACTGCACTCTCTAAGGT | | 113 |
| HMBS reverse | GGCATGTTCAAGCTCCTTGGTA | | 114 |
| HMBS probe | CCTCCCCAGTTCTTGTCCCC | | 115 |

The HMBS forward and reverse primers amplify a region of the HMBS gene. For a particular set of genes for detection, each probe for the set comprises a detectably different dye, i.e., that can be detected and distinguished simultaneously in a multiplex reaction. Each probe will also comprises a quenchers (one or more of the quenchers may be the same, as discussed herein). For example, if four genes are detected in a CT/NG diagnostic assay, one set of primers for each gene may be used, along with one probe for each gene. Each probe in the assay will comprise a detectably different dye and a quencher. Nonlimiting exemplary detectably different dyes and quenchers are discussed herein. In some embodiments, the dye is on the 5' end of the probe and the quencher is on the 3' end of the probe.

In addition, in some embodiments, an exogenous DNA control derived from an unrelated bacterial DNA is used, along with forward and reverse primers, and a probe for detecting the exogenous control (the probe includes a dye that is detectably different from the other probes in the reaction).

8.2. Example 2: Double-Denature Method for Detecting CT and NG Using Real-Time PCR One of the potential drawbacks of using the more stable genomic target genes for detecting CT and NG is that they are not present at high copy number, like the plasmid targets used in some other diagnostic tests. As a result, a double denaturing step was developed to increase the sensitivity of target detection. In the double denaturing step, the samples are denatured a first time, and then the primers and probes are added and the sample is denatured a second time prior to the start of thermocycling. Without intending to be bound by any particular theory, the initial denaturation step may effectively double the number of templates (and therefore the concentration of template) in the reaction before the primers and probes are added.

To test the effect of a double denaturing step, three different reactions were carried out for each target gene, NG2, NG4, CT1, and CT2. The final reaction components were the same in each case and included: 50-100 mM KCl, 4-9 mM $MgCl_2$, 200-500 μM dNTPs, 50 mM Tris, pH 8.6, 1 mM EDTA. AptaTaq (0.25 units/μl; Roche) was used for amplification. In this experiment, the NG2e primers and probe (each at 200 nM), the NG4d primers and probe (each at 200 nM), the CT1c primers and probe (primers at 400 nM, probe at 200 nM), and the CT2a primers and probe (primers at 400 nM, probe at 200 nM) were used. In addition, the primers and probe for detecting HMBS (each at 200 nM) and a set of primers and a probe for detecting an exogenous control DNA were included. Each probe comprised a detectably different dye on the 5' end and a quencher on the 3' end. See Table 2 for primer and probe sequences.

One mL of sample was loaded into a GeneXpert® cartridge (Cephied, Sunnyvale, Calif.) and placed in a GeneXpert® system for analysis. In the cartridge, 100 μl aliquots of the sample are mixed with 200 μl of a guanidinium thiocyanate lysis reagent (containing 3-5M guanadinium thiocyanate, 100-150 mM sodium citrate, 0.1%-0.5% w/v N-lauroylsarcosine, and 0.5%-3% w/v N-acetyl-L-cysteine). 200 μl of DNA-binding reagent (70-100% polyethylene oxide 200) is then added to the aliquot and DNA is bound to glass fiber. The cycle is repeated 10 times and then the total DNA is eluted into ~85 μl Tris/EDTA buffer (50 mM Tris, 1 mM EDTA). Following elution of the DNA, one of the three reaction conditions was applied.

In the control reaction, the real time PCR protocol was as follows: the enzyme, primers, and probes for detecting NG2, NG4, CT1, CT2, endogenous control (HMBS), and a bacterial DNA exogenous control were added to the DNA eluate. A 25 μl aliquot is heated to 94° C. for 60 seconds. The aliquot is then cycled 45 times with the following 2-step cycle: (1) 94° C. for 5 seconds, (2) 66° C. for 30 seconds.

In the pre-denature reaction, the real time PCR protocol was as follows: a 25 μL aliquot of eluate is heated for 60 seconds at 95° C., and then two 20 μl aliquots of eluate are heated sequentially to 95° C. for 60 seconds. The enzyme and primers and probes for detecting NG2, NG4, CT1, CT2, endogenous control (HMBS), and a bacterial DNA exogenous control are added to the eluate. A 25 μl aliquot of the DNA eluate containing enzyme, primers, and probes is then heated to 94° C. for 60 seconds. The aliquot is then cycled 45 times with the following 2-step cycle: (1) 94° C. for 5 seconds, (2) 66° C. for 30 seconds.

In the double-denature method, the real time PCR protocol was as follows: a 25 μL aliquot of eluate is heated for 60 seconds at 95° C., and then two 20 μl aliquots of eluate are heated sequentially to 95° C. for 60 seconds. The enzyme and primers and probes for detecting NG2, NG4, CT1, CT2, endogenous control (HMBS), and a bacterial DNA exogenous control are added to the eluate. Six aliquots of 15-25 μl each are heated sequentially to 95° C. for 5 seconds. A 25 μl aliquot of the DNA eluate containing enzyme, primers, and probes is then heated to 94° C. for 60 seconds. The aliquot is then cycled 45 times with the following 2-step cycle: (1) 94° C. for 5 seconds, (2) 66° C. for 30 seconds. The time to result was about 87 minutes.

The results of that experiment are shown in FIG. 1. For target NG2, three samples detected with the control protocol and two samples detected with the pre-denature protocol failed to amplify, while only one sample detected with the double-denature protocol failed to amplify. For NG4, five samples detected with the control protocol and one sample detected with the pre-denature protocol failed to amplify, and only one sample detected with the double-denature protocol failed to amplify. For CT1, two samples detected with the control protocol and one sample detected with the pre-denature protocol failed to amplify, while no samples detected with the double-denature protocol failed to amplify. For CT2, all of the samples amplified using all three reaction conditions. Thus, for three of the four target genes, the number of samples that failed to amplify the target decreased when the double-denature protocol was used. In addition, for all four targets, positive signals appeared at earlier cycle times in the double-denature protocol than in the control or pre-denature protocol.

8.3. Example 3: Inclusivity and Exclusivity of CT/NG Diagnostic Test

To confirm the specificity and sensitivity of a diagnostic test that detects target genes NG2, NG4, and CT1, the following CT and NG strains, and sample types were analyzed:
1. Fifteen serovars of CT;
2. Thirty clinical specimens known to contain CT;
3. Eleven clinical specimens known to contain the Swedish variant nvCT;
4. Fifty geographically diverse NG strains from the U.S., U.K., and Sweden; and
5. One hundred and one non-CT/non-NG pathogens and organisms that frequently colonize the genital tract. See Table 3.

TABLE 3

| Microorganisms tested for cross-reactivity |
|---|
| *Acinetobacter calcoaceticus* |
| *Acinetobacter lwoffi* |
| *Aerococcus viridans* |
| *Aeromonas hydrophila* |
| *Alcaligenes faecalis* |
| *Arcanobacterium pyogenes* |
| *Bacteriodes fragilis* |
| *Bifidobacterium adolescentis* |
| *Branhamella catarrhalis* |
| *Brevibacterium linens* |
| *Candida albicans* |
| *Candida glabrata* |
| *Candida parapsilosis* |
| *Candida tropicalis* |
| *Chlamydia pneumoniae* |
| *Chromobacterium violaceum* |
| *Citrobacter freundii* |
| *Clostridium perfringens* |
| *Corynebacterium genitalium* |
| *Corynebacterium xerosis* |
| *Cryptococcus neoformans* |
| Cytomegalovirus[1] |
| *Eikenella corrodens* |
| *Entercoccus avium* |
| *Entercoccus faecalis* |
| *Entercoccus faecium* |
| *Enterobacter aerogenes* |
| *Enterobacter cloacae* |
| *Erysipelothrix rhusiopathiae* |
| *Escherichia coli* |
| *Elizabethkingia meningoseptica*[3] |
| *Fusobacterium nucleatum* |
| *Gardnerella vaginalis* |
| *Gemella haemolysans*[2] |
| *Haemophilus influenzae* |
| Herpes simplex virus I[1] |
| Herpes simplex virus II[1] |
| Human papilloma virus 16[1] |
| *Kingella dentrificans* |
| *Kingella kingae* |
| *Klebsiella oxytoca* |
| *Klebsiella pneumoniae* |
| *Lactobacillus acidophilus* |
| *Lactobacillus brevis* |
| *Lactobacillus jensonii* |
| *Lactobacillus lactis* |
| *Legionella pneumophila* |
| *Leuconostoc paramensenteroides* |
| *Listeria monocytogenes* |
| *Micrococcus luteus* |
| *Moraxella lacunata* |
| *Moraxella osloensis* |
| *Morganella morganii* |
| *Mycobacterium smegmatis* |
| *N. meningiditis* |
| *N. meningitidis* Serogroup A |
| *N. meningitidis* Serogroup B |

TABLE 3-continued

Microorganisms tested for cross-reactivity

*N. meningitidis* Serogroup C
*N. meningitidis* Serogroup D
*N. meningitidis* Serogroup W135
*N. meningitidis* Serogroup Y
*Neisseria cinerea*
*Neisseria dentrificans*
*Neisseria elongata* (3)
*Neisseria flava*
*Neisseria flavescens* (2)
*Neisseria lactamica* (5)
*Neisseria mucosa* (3)
*Neisseria perflava*
*Neisseria polysaccharea*
*Neisseria sicca* (3)
*Neisseria subflava* (2)
*Paracoccus denitrificans*
*Peptostreptococcus anaerobius*
*Plesiomonas shigelloides*
*Propionibacterium acnes*
*Proteus mirabilis*
*Proteus vulgaris*
*Providencia stuartii*
*Pseudomonas aeruginosa*
*Pseudomonas fluorescens*
*Pseudomonas putida*
*Rahnella aquatilis*
*Saccharomyces cerevisiae*
*Salmonella minnesota*
*Salmonella typhimurium*
*Serratia marcescens*
*Staphylococcus aureus*
*Staphylococcus epidermidis*
*Staphylococcus saprophyticus*
*Streptococcus agalactiae*
*Streptococcus bovis*
*Streptococcus mitis*
*Streptococcus mutans*
*Streptococcus pneumoniae*
*Streptococcus pyogenes*
*Streptococcus salivarius*
*Streptococcus sanguis*
*Streptomyces griseinus*
*Vibrio parahaemolyticus*
*Yersinia enterocolitica*

(n) number of strains tested
[1] Tested at $1 \times 10^5$ genome copies/mL
[2] Tested at $5 \times 10^6$ cfu/mL
[3] Previously known as *Flavobacterium meningosepticum*

In this experiment, the NG2e primers and probe (each at 200 nM), the NG4d primers and probe (each at 200 nM), and the CT1c primers and probe (primers at 400 nM, probe at 200 nM) were used. In addition, the primers and probe for detecting HMBS (each at 200 nM) and a set of primers and a probe for detecting an exogenous control DNA were included. Each probe comprised a detectably different dye on the 5' end and a quencher on the 3' end. See Table 2 for primer and probe sequences. Table 4 shows the results key for the diagnostic test that detects NG2, NG4, and CT1.

TABLE 4

Results key

| Result | NG2 | NG4 | CT1 | Endogenous control | Exogenous control |
|---|---|---|---|---|---|
| NG detected, CT detected | + | + | + | +/− | +/− |
| NG not detected, CT detected | + | − | + | +/− | +/− |
| NG not detected, CT detected | − | + | + | +/− | +/− |

TABLE 4-continued

Results key

| Result | NG2 | NG4 | CT1 | Endogenous control | Exogenous control |
|---|---|---|---|---|---|
| NG detected, CT not detected | + | + | − | +/− | +/− |
| NG not detected, CT not detected | − | + | − | +/− | +/− |
| NG not detected, CT not detected | − | − | − | + | + |
| Invalid | − | − | − | − | +/− |
| Invalid | − | − | − | +/− | − |

As indicated in Table 4, if both NG2 and NG4 are detected, NG is detected in the sample, while detection of only one of them means NG has not been detected. Further, the endogenous and exogenous control results are ignored if any of the CT or NG markers are detected.

The diagnostic test was able to detect all strains in (1) through (4), above, and there was no cross-reactivity with any of the non-CT/non-NG pathogens and organisms in (5) (see Table 3), which were tested at a concentration of $10^6$ CFU/mL, except where indicated. In addition, the test was accurate in the presence of the following concentrations of substances that may be present in urogenital speciments: <1% v/v blood for swabs, <0.8% w/v mucin for swabs, <0.3% v/v blood for urine, <0.2% w/v mucin for urine, <0.3 mg/ml bilirubin for urine, <0.2% Vagisil® powder for urine.

8.4. Example 4: Detection of CT and NG in Patient Samples

For testing on the GeneXpert®, a urine sample was collected for each male patient. For female patients, a urine sample, an endocervical swab sample, and a vaginal swab sample was collected. A buffer was added to the urine samples, and the swabs were placed in buffer, prior to use. In this experiment, the NG2e primers and probe (each at 200 nM), the NG4d primers and probe (each at 200 nM), and the CT1c primers and probe (primers at 400 nM, probe at 200 nM) were used. In addition, the primers and probe for detecting HMBS (each at 200 nM) and a set of primers and a probe for detecting an exogenous control DNA were included. Each probe comprised a detectably different dye on the 5' end and a quencher on the 3' end. See Table 2 for primer and probe sequences.

One mL of sample was loaded into a GeneXpert® cartridge (Cepheid, Sunnyvale, Calif.) and placed in a GeneXpert® system for analysis. In the cartridge, 100 µl aliquots of the sample are mixed with 200 µl of a guanidinium thiocyanate lysis reagent (containing 3-5M guanadinium thiocyanate, 100-150 mM sodium citrate, 0.1%-0.5% w/v N-lauroylsarcosine, and 0.5%-3% w/v N-acetyl-L-cysteine). 200 µl of DNA-binding reagent (70-100% polyethylene oxide 200) is then added to the aliquot and DNA is bound to glass fiber. The cycle is repeated 10 times and then the total DNA is eluted into ~85 µl Tris/EDTA buffer (50 mM Tris, 1 mM EDTA).

Following elution of the DNA, the double-denature protocol described above is used to detect CT and NG targets, as follows. A 25 µl aliquot of eluate is heated for 60 seconds at 95° C., and then two 20 µl aliquots of eluate are heated sequentially to 95° C. for 60 seconds. The enzyme and primers and probes for detecting NG2, NG4, CT1, endogenous control (HMBS), and a bacterial DNA exogenous control are added to the eluate. Six aliquots of 15-25 µl each are heated sequentially to 95° C. for 5 seconds. A 25 μl aliquot of the DNA eluate containing enzyme, primers, and probes is then heated to 94° C. for 60 seconds. The aliquot is then cycled 45 times with the following 2-step cycle: (1) 94° C. for 5 seconds, (2) 66° C. for 30 seconds. The time to result was about 87 minutes. A positive signal at any time before the end of the 45 cycles is considered a positive result for all of the target genes.

In order to determine the sensitivity and specificity of the test, the patient infected status was determined by analyzing each sample with the GenProbe APTIMA Combo 2® Assay, which detects ribosomal RNA from both CT and NG, and with the BD ProbeTec™ ET *Chlamydia trachomatis* and *Neisseria gonorrhoeae* Amplified DNA Assay, which detects CT cryptic plasmid DNA and NG genomic DNA. Each test was used to analyze a urine sample and an endocervical swab sample from each female patient and a urine sample and urethral swab sample from each male patient. FIG. 2 shows the patient infected status grid according to the results from each test. In that figure, EQ=equivocal (i.e., if the result falls within the assay's grey zone); I=infected; and NI=not infected. Since the combination of the two tests was used to determine patient infected status, however, the overall patient infected status accuracy was higher than would have been obtained with either of the two tests alone.

6,550 samples were tested using the CT/NG test described herein. 97.1% (6,360/6,550) of the samples were correctly identified as infected or not infected on the first attempt. Of the 190 samples that failed on the first attempt (due to system error (159), invalid result (17), or no result (14)), 185 were retested. 164 of the retested samples were correctly identified as infected or not infected on the second attempt. Thus, the overall success rate of the assay was 99.6% (6,524/6,550).

The overall sensitivity and specificity of the present assay (referred to as "Xpert CT/NG Assay") and five different CT/NG assays that are currently available are shown in FIG. 3. As shown in FIG. 3A, the present assay had higher sensitivity for detecting CT than the five currently available assays for all four sample types. As shown in FIG. 3B, the present assay had over 99% specificity for detecting CT, which was comparable to or higher than the five currently available assays for the four sample types. As shown in FIG. 3C, the present assay had 100% sensitivity for detecting NG in both types of swab samples, which was higher than three of the four currently available assays, and had higher sensitivity than two of the three currently available tests for female urine samples. As shown in FIG. 3D, the present assay had 99.9% to 100% specificity for detecting NG in all four sample types.

8.5. Example 5: Screening of Patient Samples for Elevated Genomic Copy Number Patient samples were screened for elevated genomic copy number on the GeneXpert® essentially as described in Example 4, using HMBS as the indicator of genomic copy number. Primers and probes are listed in Table 2. A statistical analysis of the results is shown in Table 5.

TABLE 5

CT/NG SAC Ct statistical summary

A: ES = Endocervical Swabs; VS = Vaginal Swabs

| Disease Type | test | ES TP | ES TN | n_ES test TP | n_ES test TN | VS TP | VS TN |
|---|---|---|---|---|---|---|---|
| CT | Mean | 20.4 | 21.4 | 193 | 3540 | 20.7 | 22 |
| CT | Standard Error | 0.13 | 0.03 | 193 | 3540 | 0.16 | 0.04 |
| CT | Median | 20.2 | 21.3 | 193 | 3540 | 20.6 | 22.3 |
| CT | Mode | 18.5 | 21.2 | 193 | 3540 | 21.9 | 23.1 |
| CT | Standard Deviation | 1.87 | 2.03 | 193 | 3540 | 2.27 | 2.15 |
| CT | Sample Variance | 3.482 | 4.101 | 193 | 3540 | 5.171 | 4.644 |
| CT | Range | 9.1 | 20.6 | 193 | 3540 | 15.8 | 17.3 |
| CT | Minimum | 17.2 | 16.6 | 193 | 3540 | 16.3 | 16.1 |
| CT | Maximum | 26.3 | 37.2 | 193 | 3540 | 32.1 | 33.4 |
| CT | Count | 193 | 3540 | 193 | 3540 | 200 | 3534 |
| CT | Confidence Level(95.0%) | 0.265 | 0.067 | 193 | 3540 | 0.317 | 0.071 |
| NG | Mean | 20.8 | 21.4 | 52 | 3704 | 21.1 | 22 |
| NG | Standard Error | 0.29 | 0.03 | 52 | 3704 | 0.32 | 0.04 |
| NG | Median | 20.4 | 21.3 | 52 | 3704 | 21.1 | 22.2 |
| NG | Mode | 20.4 | 21.2 | 52 | 3704 | 22.7 | 23.1 |
| NG | Standard Deviation | 2.09 | 2.03 | 52 | 3704 | 2.28 | 2.18 |
| NG | Sample Variance | 4.387 | 4.116 | 52 | 3704 | 5.186 | 4.74 |
| NG | Range | 8.3 | 20.6 | 52 | 3704 | 9 | 17.3 |
| NG | Minimum | 17.8 | 16.6 | 52 | 3704 | 17.1 | 16.1 |
| NG | Maximum | 26.1 | 37.2 | 52 | 3704 | 26.1 | 33.4 |
| NG | Count | 52 | 3704 | 52 | 3704 | 52 | 3711 |
| NG | Confidence Level(95.0%) | 0.583 | 0.065 | 52 | 3704 | 0.634 | 0.07 |

B: UR(F) = Urine Female; UR(M) = Urine Male

| Disease Type | test | UR(F) TP | UR(F) TN | UR(M) TP | UR(M) TN | Conf Int Check |
|---|---|---|---|---|---|---|
| CT | Mean | 23.6 | 24.9 | 22.4 | 26.3 | . |
| CT | Standard Error | 0.17 | 0.04 | 0.18 | 0.04 | −0.256411544 |
| CT | Median | 23.4 | 25.1 | 22.2 | 26.6 | . |
| CT | Mode | 23.1 | 25.1 | 20.4 | 27.1 | . |
| CT | Standard Deviation | 2.43 | 2.25 | 2.43 | 2.41 | . |
| CT | Sample Variance | 5.903 | 5.067 | 5.919 | 5.79 | . |
| CT | Range | 15.6 | 17.8 | 12.9 | 17.6 | . |

TABLE 5-continued

| CT/NG SAC Ct statistical summary | | | | | | |
|---|---|---|---|---|---|---|
| CT | Minimum | 17.3 | 16.9 | 17.2 | 17.5 | . |
| CT | Maximum | 32.9 | 34.7 | 30.1 | 35.1 | . |
| CT | Count | 207 | 3550 | 193 | 3233 | . |
| CT | Confidence Level(95.0%) | 0.333 | 0.074 | 0.345 | 0.083 | . |
| NG | Mean | 23.3 | 24.9 | 20.4 | 26.3 | . |
| NG | Standard Error | 0.34 | 0.04 | 0.17 | 0.04 | −0.582199293 |
| NG | Median | 23.1 | 25.1 | 20.1 | 26.6 | . |
| NG | Mode | 22.3 | 25.1 | 20.1 | 27.1 | . |
| NG | Standard Deviation | 2.43 | 2.31 | 1.87 | 2.36 | . |
| NG | Sample Variance | 5.919 | 5.332 | 3.508 | 5.564 | . |
| NG | Range | 9.1 | 34.7 | 9.7 | 17.9 | . |
| NG | Minimum | 18.6 | 0 | 17.3 | 17.2 | . |
| NG | Maximum | 27.7 | 34.7 | 27 | 35.1 | . |
| NG | Count | 51 | 3712 | 117 | 3314 | . |
| NG | Confidence Level(95.0%) | 0.684 | 0.074 | 0.343 | 0.08 | . |

TP = True Positives,
TN = True Negatives

Plots of these results are shown in FIG. 4 (the term "SAC" is used to refer to HMBS). These results demonstrate the clinical utility of quantifying human genome copy number as a marker of infection and inflammation. The means for all groups are non-overlapping, but very large differences are seen in the male urine specimens. In fact, for NG infection, the peak separation is so stark that one would be able to predict the presence or absence of infection based on the SAC value alone in the majority of cases.

These results likely reflect an inflammatory response in the urogenital tract. The signal observed is likely due, at least in part, to DNA in infiltrating cells. However, at least some of the signal could be from free DNA in the urine; this could have arisen as a function of apoptosis or cytotoxic immune responses in the urethral tract.

Notably, genomic copy number level differs between sample types. In particular, genomic copy number level was lower in urine than in vaginal or endocervical samples. See FIG. 5. FIG. 6A-C shows genomic copy number in different sample types as a function of infection status. In self-collected vaginal samples (6A), samples that were negative for CT and NG were characterized by a SAC Ct of about 24 or greater, whereas samples that were positive for infection tended to have a SAC Ct of about 20 or less. In male urine (6B), samples that were negative for CT and NG were characterized by a SAC Ct of about 28 or greater, whereas samples that were positive for infection tended to have a SAC Ct of about 24 or less. In male urine, of 32 CT/NG coinfections, all 32 occurred in the left-most decile of SAC values, i.e., all had SAC Cts of less than 24 (6C).

Genomic copy number also correlates with symptomatic status, as can be seen from FIG. 7. SAC Ct values were lower for symptomatic subjects who were positive for CT/NG infection, intermediate for asymptomatic subjects who were positive for CT/NG infection, and higher for true negative subjects. CT/NG-negative subjects with SAC Ct values of less than about 24 may have a different urogenital infection and are candidates for further testing.

FIG. 8 shows genomic copy number (SAC Ct values) in various conditions (from left to right): negative (control) urine; inflammation, but no pathogen; *mycoplasma genitalium* positive; possible *trichomonas vaginalis; ureaplasma parvum* positive without inflammation; *ureaplasma parvum* positive with inflammation; *ureaplasma urealyticum* positive without inflammation; and *ureaplasma urealyticum* positive with inflammation.

The interpretation of HMBS signal adds to the confidence in the interpretation of CT or NG results e.g., confirming true positives and identifying possible false positives (see FIG. 9). Moreover, it can potentially be used as an indirect indicator, in patients negative for both pathogens, of another potential infectious (infection with *mycoplasma, ureaplasma, trichomonas*, or other organisms still to be described) or non-infectious (autoimmune urethritis, prostatitis, bladder cancer, prostate cancer, kidney cancer) process.

All publications, patents, patent applications and other documents cited in this application are hereby incorporated by reference in their entireties for all purposes to the same extent as if each individual publication, patent, patent application or other document were individually indicated to be incorporated by reference for all purposes.

While various exemplary embodiments have been illustrated and described in some detail for clarity of understanding and by way of example, it will be appreciated that changes can be made without departing from the spirit and scope of the invention(s).

What is claimed is:

1. A method of treating a human male for infection or inflammation of the urogenital tract, wherein the human male is one who has been tested for prostate-specific antigen (PSA) as an indicator of prostate cancer and found to have a sufficiently elevated PSA level to be a candidate for a biopsy and the method comprises:
   determining that the human male has an infection or inflammation of the urogenital tract by:
      obtaining or having obtained a sample from the urogenital tract of the human male;
      performing or having performed an assay on the sample for an indicator of genomic copy number; and
      determining that the human male has a genomic copy number level that is higher than a control genomic copy number level, which is indicative of the presence of infection or inflammation of the urogenital tract; and
   treating the human male determined to have infection or inflammation of the urogenital tract with an antibiotic or an anti-inflammatory agent, respectively.

2. The method of claim 1, wherein the indicator of genomic copy number comprises a nucleic acid sequence that is expected to be present in the genome of the human male in one or two copies.

3. The method of claim 1, wherein the indicator of genomic copy number comprises a nucleic acid sequence selected from the group consisting of a hydroxymethylbilane synthase (HMBS), glyceraldehyde 3-phosphate dehydrogenase (GAPDH), beta-actin, and beta-globin nucleic acid sequence.

4. The method of claim 3, wherein the indicator of genomic copy number comprises a HBMS nucleic acid sequence.

5. The method of claim 1, wherein said assay for an indicator of genomic copy number comprises real-time PCR.

6. The method of claim 5, wherein the indicator of genomic copy number comprises an HBMS sequence, which is amplified using primers comprising SEQ ID NO:113 and SEQ ID NO:114.

7. The method of claim 6, wherein an amplicon amplified by the primers is detected using a probe, and the probe comprises SEQ ID NO:115.

8. The method of claim 1, wherein the human male has been identified as having at least one clinical symptom of urogenital infection or inflammation.

9. The method of claim 1, wherein the human male is one who has had a prior sexually transmitted disease.

10. The method of claim 1, wherein the method additionally comprises deferring biopsy until after infection is ruled out or resolved.

11. The method of claim 10, wherein the method additionally comprises performing one or more additional assay(s) of the same, or a different, sample from the human male for a pathogen or causing one or more additional assay(s) for the pathogen to be performed.

12. The method of claim 10, wherein the method additionally comprises performing a second assay of a sample obtained from the urogenital tract of the human male for an indicator of genomic copy number or causing the second assay to be performed.

13. The method of claim 11, wherein said assaying for a pathogen comprises assaying the sample from the human male for the presence of a nucleic acid sequence that is indicative of the pathogen.

14. The method of claim 13, wherein the pathogen comprises a pathogen selected from the group consisting of *Chlamydia trachomatis* (CT), *Neisseria gonorrhoeae* (NG), *Mycoplasma genitalium* (MG), *Ureaplasma*, *Trichomonas*, *Leptotrichia*, and *Sneathia*.

15. The method of claim 1, wherein the method additionally comprises assaying the same, or a different sample from the human male for the presence and/or level of a microRNA (miRNA) that is correlated with inflammation.

\* \* \* \* \*

SEQUENCE LISTING

<160> NUMBER OF SEQ ID NOS: 115

<210> SEQ ID NO 1
<211> LENGTH: 600
<212> TYPE: DNA
<213> ORGANISM: Neisseria gonorrhoeae

<400> SEQUENCE: 1
agtgtccatt cttttcgggc agtctgaatc cgtctggctg attaagggta aaacttattc    60

```
aaatcggcaa ccaatttggt taactcttcc tgattcggct tattcatgcc ccggtaaact    120
ttgacgtagc ctttgtcgtt tttcatattc acgacataga tgacgaaacg tgtgccgttg    180
aatccttttt ccgcatcgca ggtgtagtac gtcacacccc cgctttccgc ttttccagt    240 acgcagtcgt ttttgcggta accttgctcc ttcgctatcc aatcccgcgc aaatgaagcc    300
ctgtacgcgt ccggcacgcg gacttggtcg accaataaat catgatcggg attttgggaa    360
taaccgtaat ggaaaacggc gtttgaaccg ttcaattgcg cctccggcat ttgataacgc    420
cggttttgga aaacgcatc gttcgggttc atgcaggcag ttaaaagaaa agtcaggagt    480
gcggctgtgt atttcatagt tgttcactc gggcggttaa aggaaaagtc aggaatacgg    540
ttgtgtattt tatggtttat tctcttataa acagttataa acggtttcaa ggcggcttgc    600

<210> SEQ ID NO 2
<211> LENGTH: 400
<212> TYPE: DNA
<213> ORGANISM: Neisseria gonorrhoeae

<400> SEQUENCE: 2
tcaagcaaaa tctccaaaac ccgaacaggc tatgggtttt ttgccaaaat gatttttgca     60
agccgttggc tgcaagtgcc gatttatgcg gggctgactg ttgtacgggc gatttgtgcc    120 tataagttt tgaaatcgtt gaagcatctg gtcatgaatt tggatgtgtc ggacgaaaac    180
gccatcatgc tcgctgtttt aaatctgatt gatgtggtta tgattgcgaa tttgctgacc    240
atggtgcaga ttggcgggta tgagtcgttc gtatcccggt tgcgtatcga cgaccatcct    300
gaccggcccg agtggttgag ccatgtgaat gcaccggtat tgaaggtaag gctgtcgatg    360
tcgattatcg gtattcatcc atccatttgc tccaaacatt                          400

<210> SEQ ID NO 3
<211> LENGTH: 200
<212> TYPE: DNA
<213> ORGANISM: Neisseria gonorrhoeae

<400> SEQUENCE: 3
agtgcgtcgg gtttgcgcaa tacctcaact tcaacctcgg caacgccttc aaatacatct     60
ggcggcacaa ggaaaaaggc gggcgcgaag acttggaaaa agccctgcgg tacttggaac    120
gccaacgcgc cggcgcgccg aagttcaaga aactcaaaca ccgccgctat gaaaaaatgt    180
acgccggtct gaaagattgc                                                200

<210> SEQ ID NO 4
<211> LENGTH: 778
<212> TYPE: DNA
<213> ORGANISM: Neisseria gonorrhoeae

<400> SEQUENCE: 4
tgctggtgtt tcttgccgtc ggcatgctgg cgggcgagga aggcgttggc ggcattgcct     60
tcaataatgt cgtgatggcg aatttcatca gccagcttgc tttggcggtt attctgctcg    120
acggcggttt gcggacgcag ctttccagtt ttcggattgc gttgaagccc gcgtcggtac    180
tcgcttcgtg gggcgtgttt gccactgtgc ttccgctggg actgtttgca acttttttatc    240 tcggtttgga ttggaagttc ggcgtgctga tggcggcgat tgtcggttcg accgatgccg    300
gcgcggtatt cagcctttg cgcaacagcg gcgtgcgttt gaacgaacgg gtgcaggcga    360
ctttggaaat cgaatcgggt gcgaacgacc cgatggcggt tttttggtt acggcactga    420 ttaccatgat tatgcagccg gcggaatcgg gtgcggcagc gtttgtccgg atgcttgcgc    480
```

```
tgcaaatcgg tttcggtctg ctgacgggtt gggcgggcgg aaagatattg gcaaagctgg    540
tacgccgtct gaatcttgcg gaaggtctgt acgcgctgat gattgtgtcg ggcgggctgc    600
ttgtgtttgc gtttaccaat accataggcg gcagcggctt tttggcggtt taccttgccg    660
gcatcattgt cggtaaccag cgcaaccgtg cgacggaaca cgttttgcgt gtgatggacg    720
gtttggcttg gctggcgcag gcaactttgt tcgtcatgct cggtctgctg gtttctcc     778

<210> SEQ ID NO 5
<211> LENGTH: 492
<212> TYPE: DNA
<213> ORGANISM: Neisseria gonorrhoeae

<400> SEQUENCE: 5
cctgcatcta aaccacattt taatataaga gactccaatt tagatacagg acatgtcgat     60
ggtactcacg gacactataa tttttagtaa gaaatatgaa tataatagaa ataataagta    120
ggaatcgttt tctaaaacaa atatatccta gtggcataat ggatatttca ctagtctctt    180
tttcaactga cttgtctaat tgtatttttaa ctatccgaac aagtacaaag ccttctgtag    240
aaatcgaaaa atgggggctg tggctaaaag attatgatac agttgaaatt gaattaagaa    300
atagctttat taaggaatg aaatgtcaaa attggtcgca taacaataga aatatatgcc    360
aagtagaaat aaagaaccaa gaagatggtc taaaaataat aagattttac gacaataatt    420
caaattggtt attggaacta gaagtttatg gattagtttt ccaagggtgt aagacttata    480
tgaaagaggg tt                                                        492

<210> SEQ ID NO 6
<211> LENGTH: 750
<212> TYPE: DNA
<213> ORGANISM: Neisseria gonorrhoeae

<400> SEQUENCE: 6
tcaaagaaat gttggatatg ttggcagaag gtggcacagg cattgccatt attccagtca     60
gttgcgtgat tgcaccaagc aaagccaaaa gcgaaattgt gaaatatcat cgcttaaaag    120
ccgtgatgtc tatgccgagc gaactgtttt acccagttgg cacggtaacg tgcattgtcg    180
tatttgaagc ccataaaccg catttttcaga cagtcgtgat tgacccggac acacaagaag    240
aaatcagcac gaaaaaagcc tgtcgcaaaa cgtggtttgg ctactggcgt gatgacggtt    300
ttgaaaaaac caaacacttg ggacgcattg atttatacga ccgctggcag ggcattaaag    360
cgcgctggtt ggaacattat ttaaacaacg aagttcacac aggagaatcg gtaacagcat    420
ttgtaactga taacgatgaa tgggttgccg aagcctattt ggaaactgat tattccaaaa    480
ttacccgagc agattttgag caagtcgtgc gtgaatttgc tttatttcaa ctactgggag    540
cggaagtagg gccgactgaa aatttggata tgaaagcta tgaagacgat gacaataacg    600
acttcggaga cgatgaataa tggttgaatt gcaagagatt tttgatgtga gttacggttc    660
aaaattagat ttgaataaaa tgagcagctt caatccaaca atcaactttg taggcaggtc    720
aggcaaaaat aatggtgtaa cagcatctgt                                    750

<210> SEQ ID NO 7
<211> LENGTH: 450
<212> TYPE: DNA
<213> ORGANISM: Chlamydia trachomatis

<400> SEQUENCE: 7
```

```
ttgtagagag gcaaacacct caacgcctgt tagtatatgc tctttggtgt gagagtttag    60
gactgccgaa ctgctttcct tagttttaat tccatctttt cgcaaaggta gatccgatat   120
cagcaaaagt gctcctaaag gaagattcct tcggtatcct gcagcaaata aggtggcaca   180
ctccatctcg acagtttgag ctttattttc atatagtttt cgacggaact ctttattaaa   240
ctcccaaaac cgaatgttag tcgtgtgggt gatgcctata tggtaaggga ggttttggc    300 ttcgagaata ttggtgatca ttttttgtac gacaaaatta gctaatgcag ggacctctgg   360
ggggaagtat gcatctgatg ttccatcttt tcggatgcta gcaacaggga caaaataatc   420
tcctatttgg tagtgggatc ttaagcctcc                                    450

<210> SEQ ID NO 8
<211> LENGTH: 480
<212> TYPE: DNA
<213> ORGANISM: Chlamydia trachomatis

<400> SEQUENCE: 8
ttaagacagg ggtttatttta attggttaac tgtgcttccc acggagttca atgttttgat    60
gaaggaggag ttctgttgag cgatttgctg cataatgttg atgtttgtag atgcgtgaga   120
gaggataatc tgtccatttt gtcgggcagt tactaattgg tcttggatat ttgagcgttg   180
tgcagaatag ttttggttct ggttttgtac tcgtgtgatt tcgtcttctt agctccaga    240 gccaacgaca gcgtatttga tttgattcgt ttccttggtt aattgctgtt ggatattagt   300
attgtcgttt agctgcttag attgcgtgag aatcgtctct tgacgtattt ctacagcttc   360
taaaagaaga gagtaaatgc tgaacaagag ttctgctatt ggaggcgttc ccaaaggctc   420
taaaggaggt agcgaggaga cgtattgtgt gtctcctacc tgtgaggttg ctgctgacat   480

<210> SEQ ID NO 9
<211> LENGTH: 939
<212> TYPE: DNA
<213> ORGANISM: Chlamydia trachomatis

<400> SEQUENCE: 9
ttactgctgt tctgctgatg tggaagcatt ctcttcgtct tgagtagaag aagaggtttg    60
cttagggtct gttatggatt ttttttctctt ctcatgtaac tgaatcagct ctttagtcat   120
caatctactg tttgtttcta tatatgccca aatctcgtta tagcattcga gttgtgtctc   180
tgtaagcgga ttgataatca agaactcttc cagatttaat gtaagacctc ctctactcca   240
gttgacggat cctataatga gtgtcgagct attaatacag cagactttgg tatgcagaat   300
gccttcgcat gtacgttctc gtaggacaat gccgttagcc tcgaggatag ctttgacgca   360
caagtctctt cgtatttgac ttagcgaata gtaggatact tgttgcgagc ctactcgcac   420
ctctcctcga tcgtgtcgga aagcccagcg atataggtgt tcactaaata ttttagccgt   480
taagttcaca tcttttcaa gagaggcctc tgtatagttt gctgttcccg taacgacaat    540
attattgtct ataagaaggg ttttctatg taaaagagaa caccctcttc gaggtctaaa    600
ctgcacattt ccttcagtac agtgttttga aaaaggcccc atttgatagt gtacggagac   660
aggcgctcta ttagaagcct cagctaaggc tgcaagaatt ctgggggatc cgatattaaa   720
tacttttaat agaacgctgc gcttagcttg tagaattgtt tcacaaatca ttttcacagg   780
ttcgttattt ctttgctgat gagcagagta gagttggatc agttcgtgat gctgtaagag   840
tctaggtacg acttggctcg aagaagatcg ggctcgttta gaggaggaag aagaagtgtc   900
ttcgggagtc ttgtgttttc tcttggagcc ggcgagcat                          939
```

<210> SEQ ID NO 10
<211> LENGTH: 528
<212> TYPE: DNA
<213> ORGANISM: Chlamydia trachomatis

<400> SEQUENCE: 10

```
atgtttgtgt cgttcgataa atcccgttgc agagcggatg tccccgattt ttttgaaagg    60
acaggaaact ttcttctcca ttgtgtggca agagggatca atgttttata tcgtgtgaaa   120
caaatcccta actatccttc atgctatttc tcacataaag agatttcgtg ttgtcgtcgt   180
attgcaaaca ttgtgatctg tattctcaca gggcctctga tgttattggc cactgtgtta   240
ggattattag cgtataggtt ttcttctact taccagactt ctttacaaga acgctttcgt   300
tataaatatg aacaaaagca agctttagat gaataccgtg atagggaaga aaaagtcatt   360
acgcttcaga gttttgtag aggatttcta gttagaaatc atttgctcaa ccaagaaact   420
ttaacaacgt gtaagcaatg ggggcaaaaa ctattagaag gagaaaaatt ccaagggtcc   480
cagaaggacg gtctcttgta tatatttcaa aacagttttc ttctttag                528
```

<210> SEQ ID NO 11
<211> LENGTH: 902
<212> TYPE: DNA
<213> ORGANISM: Chlamydia trachomatis

<400> SEQUENCE: 11

```
gaggggagaa ttctaagaaa agaaaataat gtagcatata tttatgaaat gttgtaatat    60
tatagcatta caaaaggtg cgatatgaaa atcaagagg agtctggctg caagcttttt   120
ctgacattat gctctaaaat gcaaaaagaa aagttttac aagaccttt ttcgctgttt   180
ttgtctttta gcgaacgtaa agatgtcgct tctcgctatc atatcattcg agctctttta   240
gaaggggagc tcactcaaag agagatagca gagaaatacg gagtcagtat cgcacaaatt   300
accagaggat ctaatgccct taaggatta gatcctcaat ttaaagagtt tttacaaaaa   360
gagatctgat cttctttgt aaaatacaaa taagattaaa agtatttgta tgcatgcgtt   420
gttaatgaac aaatattctg ttttagcagt tttggtacat aagtatagct gcagcatgcc   480
atgcaaatca gcttttcaag ctgattgctt ccaagatatt caaaaattca tcctcttaca   540
gcgtgcctgg ctttcttttg aaagctggcg cttatctact tggcgatagg cctaattaag   600
aagcctttta tttgattaag agatgttctt atagaagtaa gagcgtcttt tttgcgcagg   660
attattctgt cgccagtttt ttctatgatt ttaacactat aatttatgg agaaaagatg   720
ttcaaacata acatcccttt tgggggagcg ttccttcccg aagaactatt agccctata    780
cagaatctaa aagcggaatg ggagattctc aaaactcagc aaagtttttt atctgaacta   840
gattgtattt tgaaaaacta tgcggggaga caaactcctc tgactgaagt taagaatttt   900
gc                                                                  902
```

<210> SEQ ID NO 12
<211> LENGTH: 963
<212> TYPE: DNA
<213> ORGANISM: Chlamydia trachomatis

<400> SEQUENCE: 12

```
gcgttacgag cttttttcct gcttactaga aacgagggga ttattcctgc attggagtct    60
tcacatgctc tcgcacattt agtttcgatt gctccttctc taccaaagga acaaatcgtc   120
```

-continued

```
atcgttaact tatctggaag aagtgataag gatctttcac aaatcatccg cagaaacaga      180
ggaatttatg agtaaattaa cccaagtttt taaacaaact aagccatgta ttggctatct      240
aaccgctggt gatggcggta ctagttatac tattgaggcg gcaaaagctc tgattcaagg      300
aggtgtcgat attctggaac taggatttcc tttttctgat cctgttgcag ataatccaga      360
aattcaagta tctcatgatc gggctttagc agaaaatctg acgtcagaaa ctttgttaga      420
gatcgtagaa ggtatccgag cttttaatca agaagtccca ttgatcttat atagctacta      480
caatccgctt ctacaaaggg acttagatta tctacgcaga ctaaaagacg cgggaataaa      540
tggtgtgtgc gttatagatc ttccagcacc tttatcacac ggagaaaaat ctccttttga      600
agatctttta gctgtaggat tggatcctat tttgcttatt tctgcaggga caacgccgga      660
gcggatgtct ttaatacaag aacacgcaag aggccttctg tattatatcc catacaagct      720
acgagagatt ctgaagtagg tatcaaagaa gaatttcgaa aagtcagaga acattttgat      780
cttccaattg tagatagaag agatatttgt gataaaaaag aagctgcaca tgtgctgaat      840
tattcagatg gtttcattgt gaaaacagcg tttgttcatc agacaacaat ggattcttcg      900
gtagagactc tgactgcact tgcacaaaca gttattcctg gataatttat gaatatgaag      960
ccc                                                                   963
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtctgaatcc gtctggctga tt                                               22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacgtttcgt catctatgtc gtga                                             24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tcggcttatt catgccccgg taaac                                            25

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcgtttgaa ccgttcaatt g    21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aacccgaacg atgcgtttt    19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
cctccggcat ttgataacgc c    21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgggcgattt gtgcctataa g    21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttttcgtcc gacacatcca a    21

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ttttgaaatc gttgaagcat ctggtcatga a    31

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgttgaagca tctggtcatg aa                                          22

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caatcagatt taaaacagcg agcat                                       25

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tggatgtgtc ggacgaaaac gcca                                        24

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatttggatg tgtcggacga aa                                          22

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaattcgcaa tcataaccac atca                                        24

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cgccatcatg ctcgctgttt taaatctga                                   29

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgagtcgttc gtatcccggt t                                           21

```
<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agccttacct tcaataccgg tg                                              22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ctgaccggcc cgagtggttg a                                               21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
cggcccgagt ggttgagcca                                                 20

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgatttgtgc ctataagttt ttgaa                                           25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcaatcataa ccacatcaat cagat                                           25

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
ctggtcatga atttggatgt gtcggacg                                        28
```

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tctggcggca caaggaaa                                                   18

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccaagtaccg cagggctttt                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
aggcgggcgc gaagacttgg                                                 20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggacgcagct ttccagtttt c                                               21

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgccccacga agcgagta                                                   18

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
attgcgttga agcccgcgtc g                                               21

-continued

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caggcgactt tggaaatcga                                              20

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cagtgccgta accaaaaaaa cc                                           22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
cgggtgcgaa cgacccgatg                                              20

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgctgcaaat cggtttcg                                                18

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
accagctttg ccaatatctt tcc                                          23

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tctgctgacg ggttgggcgg                                              20

<210> SEQ ID NO 47

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaagctggta cgccgtctga a                                            21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgccgcctat ggtattggta a                                            21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
tgtcgggcgg gctgcttgtg ttt                                          23

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgaccaattt tgacatttca ttcc                                         24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccgaacaagt acaaagcctt ctgt                                         24

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
tcttttagcc acagccccca tt                                           22

<210> SEQ ID NO 53
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agagactcca atttagatac aggacatgt                                    29

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccattatgcc actaggatat atttgtttt                                    29

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
atggtactca cggacactat a                                            21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tggcacaggc attgccatta                                              20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caatttcgct tttggctttg c                                            21

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
tccagtcagt tgcgtgattg cacca                                        25

<210> SEQ ID NO 59
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 59
ccgctggcag ggcatta                                                       17

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttaccgattc tcctgtgtga acttc                                              25

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
agcgcgctgg ttggaacatt atttaaacaa                                         30

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ttttgatgtg agttacggtt caaaa                                              25

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttgcctgacc tgcctacaaa g                                                  21

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
tgaataaaat gagcagcttc aatccaacaa tca                                     33

<210> SEQ ID NO 65
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 65
actgccgaac tgctttcctt ag                                               22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gccaccttat ttgctgcagg at                                               22

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
cgcaaaggta gatccgatat cagcaaaagt g                                     31

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctgccgaact gctttcctta gt                                               22

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tcaaactgtc gagatggagt gtg                                              23

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
cgcaaaggta gatccgatat cagcaaaagt g                                     31

<210> SEQ ID NO 71
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 71
ttttcgcaaa ggtagatccg ata                                           23

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gttccgtcga aaactatatg aaaataaa                                      28

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
tgcagcaaat aaggtggcac actccatc                                      28

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gttaactgtg cttcccacgg ag                                            22

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aactattctg cacaacgctc aaat                                          24

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
aggaggagtt ctgttgagcg atttg                                         25

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 77
ggaggagttc tgttgagcga tt                                              22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gcccgacaaa atggacagat t                                               21

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
ctgcataatg ttgatgtttg tagatgcgtg                                      30

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aggaggagtt ctgttgagcg att                                             23

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcccgacaaa atggacagat t                                               21

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
ctgcataatg ttgatgtttg tagatgcgtg                                      30

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgacttagcg aatagtagga tacttgttg					29

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acctatatcg ctgggctttc c					21

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
cctactcgca cctctcctcg atcgtgt					27

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gtctaggtac gacttggctc gaa					23

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
aacacaagac tcccgaagac actt					24

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
aagatcgggc tcgtttagag gaggaagaa					29

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 89
ccgttgcaga gcggatgtc                                                19

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tgatccctct tgccacacaa                                               20

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
ccgatttttt tgaaaggaca ggaaactttc ttctcc                             36

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tctcacaggg cctctgatgt t                                             21

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cgttcttgta aagaagtctg gtaagtaga                                     29

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
ttggccactg tgttaggatt attagcgtat aggttt                             36

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
``` gaccttttt cgctgttttt gtc                                              23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ccccttctaa aagagctcga atg                                             23

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
cgaacgtaaa gatgtcgctt ctcgctatca                                      30

<210> SEQ ID NO 98
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ggcctaatta agaagccttt tatttg                                          26

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tcatagaaaa aactggcgac agaa                                            24

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
agaagtaaga gcgtcttttt tgcgcaggat                                      30

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cctgcattgg agtcttcaca tg                                              22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cgatgacgat ttgttccttt gg                                              22

<210> SEQ ID NO 103
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
tctcgcacat ttagtttcga ttgctccttc tc                                   32

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
caaagggact tagattatct acgcagacta                                      30

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccgtgtgata aaggtgctgg aa                                              22

<210> SEQ ID NO 106
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
aagacgcggg aataaatggt gtgtgcgtt                                       29

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tccaattgta gatagaagag atatttgtga                                      30

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 108
tgtctgatga acaaacgctg ttt                                           23

<210> SEQ ID NO 109
<211> LENGTH: 34
<212> TYPE: DNA
<213> ORGANISM: Artificial Sequence
<220> FEATURE:
<223> OTHER INFORMATION: Description of Artificial Sequence: Synthetic
probe

<400> SEQUENCE: 109
acatgtgctg aattattcag atggtttcat tgtg                               34

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 110
tccaattgta gatagaagag atatttgtga                                    30

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 111
tgtttgatga acaaacgctg ttt                                           23

<210> SEQ ID NO 112
<211> LENGTH: 34
<212> TYPE: DNA
<213> ORGANISM: Artificial Sequence
<220> FEATURE:
<223> OTHER INFORMATION: Description of Artificial Sequence: Synthetic
probe

<400> SEQUENCE: 112
acatgtgctg aattattcag atggtttcat tgtg                               34

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 113
agattcttga tactgcactc tctaaggt                                      28

```
<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ggcatgttca agctccttgg ta                                              22

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
cctccccagt tcttgtcccc                                                 20
```